(12) United States Patent
Ito et al.

(10) Patent No.: US 9,985,213 B2
(45) Date of Patent: *May 29, 2018

(54) COMPOUND, MATERIAL FOR ORGANIC ELECTROLUMINESCENCE ELEMENT, ORGANIC ELECTROLUMINESCENCE ELEMENT, AND ELECTRONIC APPARATUS

(71) Applicant: IDEMITSU KOSAN CO., LTD., Tokyo (JP)

(72) Inventors: Hirokatsu Ito, Sodegaura (JP); Tomohiro Nagao, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/658,092

(22) Filed: Jul. 24, 2017

(65) Prior Publication Data
US 2017/0324039 A1    Nov. 9, 2017

Related U.S. Application Data

(63) Continuation of application No. 14/902,248, filed as application No. PCT/JP2014/067588 on Jul. 1, 2014, now Pat. No. 9,748,494.

(30) Foreign Application Priority Data

Jul. 1, 2013   (JP) ................................ 2013-138438

(51) Int. Cl.
*H01L 51/00* (2006.01)
*C07C 211/61* (2006.01)
(Continued)

(52) U.S. Cl.
CPC .......... *H01L 51/006* (2013.01); *C07C 211/61* (2013.01); *C07D 307/91* (2013.01);
(Continued)

(58) Field of Classification Search
CPC combination set(s) only.
See application file for complete search history.

(56) References Cited

U.S. PATENT DOCUMENTS 6,436,558 B1 * 8/2002 Sato ................... H01L 51/0036
313/504
2009/0261717 A1    10/2009 Buesing et al.
(Continued)

FOREIGN PATENT DOCUMENTS

CN        101142170 A        3/2008
CN        101490207 A        7/2009
(Continued)

OTHER PUBLICATIONS

International Search Report issued in PCT/JP2014/067588 dated Oct. 7, 2014.
(Continued)

*Primary Examiner* — Mamadou Diallo
(74) *Attorney, Agent, or Firm* — Foley & Lardner LLP

(57) ABSTRACT

A compound is represented by a formula (1) below.
In the formula (1), n is 1 or 2. $Ar^1$ is represented by a formula (2) below. $Ar^2$ represents a substituted or unsubstituted aromatic hydrocarbon group having 6 to 30 carbon atoms, or a substituted or unsubstituted heterocyclic group having 1 to 20 ring atoms. $Ar^3$ is represented by a formula (3) below.

(1)

(Continued)

-continued

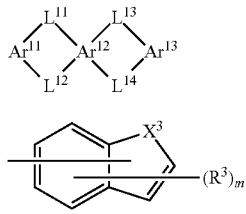
(2)

(3)

42 Claims, 1 Drawing Sheet

(51) Int. Cl.
C09K 11/02 (2006.01)
C09K 11/06 (2006.01)
C07D 307/91 (2006.01)
H01L 51/50 (2006.01)

(52) U.S. Cl.
CPC ........... *C09K 11/025* (2013.01); *C09K 11/06* (2013.01); *H01L 51/0056* (2013.01); *H01L 51/0058* (2013.01); *H01L 51/0061* (2013.01); *H01L 51/0073* (2013.01); *C07C 2603/54* (2017.05); *C07C 2603/68* (2017.05); *C09K 2211/1007* (2013.01); *C09K 2211/1011* (2013.01); *C09K 2211/1014* (2013.01); *C09K 2211/1088* (2013.01); *H01L 51/0094* (2013.01); *H01L 51/5012* (2013.01)

(56) References Cited

U.S. PATENT DOCUMENTS

2010/0219397 A1* 9/2010 Watanabe ............ C07D 233/58 257/40
2014/0021451 A1* 1/2014 Yokoyama ........... C07D 471/04 257/40
2015/0045529 A1* 2/2015 Stoessel ............... C07D 493/10 528/220

FOREIGN PATENT DOCUMENTS

| CN | 102356060 A | 2/2012 |
|---|---|---|
| CN | 103119125 A | 5/2013 |
| CN | 104684886 A | 6/2015 |
| EP | 2 038 370 A1 | 3/2009 |
| JP | 4358884 B2 | 11/2009 |
| JP | 2009-542735 A | 12/2009 |
| JP | 2013-538793 A | 10/2013 |
| JP | 2015-534543 A | 12/2015 |
| KR | 10-2008-0109000 A | 12/2008 |
| KR | 20110117548 A | 10/2011 |
| KR | 10-2012-0009761 | 2/2012 |
| KR | 20120009984 A | 2/2012 |
| WO | WO-2008/006449 A1 | 1/2008 |
| WO | WO-2012/011756 A1 | 1/2012 |
| WO | WO-2014/037077 A1 | 3/2014 |

OTHER PUBLICATIONS

Written Opinion of the International Searching Authority issued in PCT/JP2014/067588 dated Oct. 7, 2014.
English translation of International Preliminary Report on Patentability issued in PCT/JP2014/067588 dated Jan. 5, 2016.
Office Action issued in Chinese Patent Application No. 201480035355.2 dated Aug. 23, 2016.
Office Action dated Mar. 7, 2017 in corresponding Japanese Patent Application No. 2015-525244.
Office Action dated May 2, 2017 in Chinese Patent Application No. 201480035355.2.
Non-Final Office Action for U.S. Appl. No. 14/902,248 dated Dec. 1, 2016.
Notice of Allowance for U.S. Appl. No. 14/902,248 dated Apr. 25, 2017.
Corrected Notice of Allowability for U.S. Appl. No. 14/902,248 dated May 18, 2017.

* cited by examiner

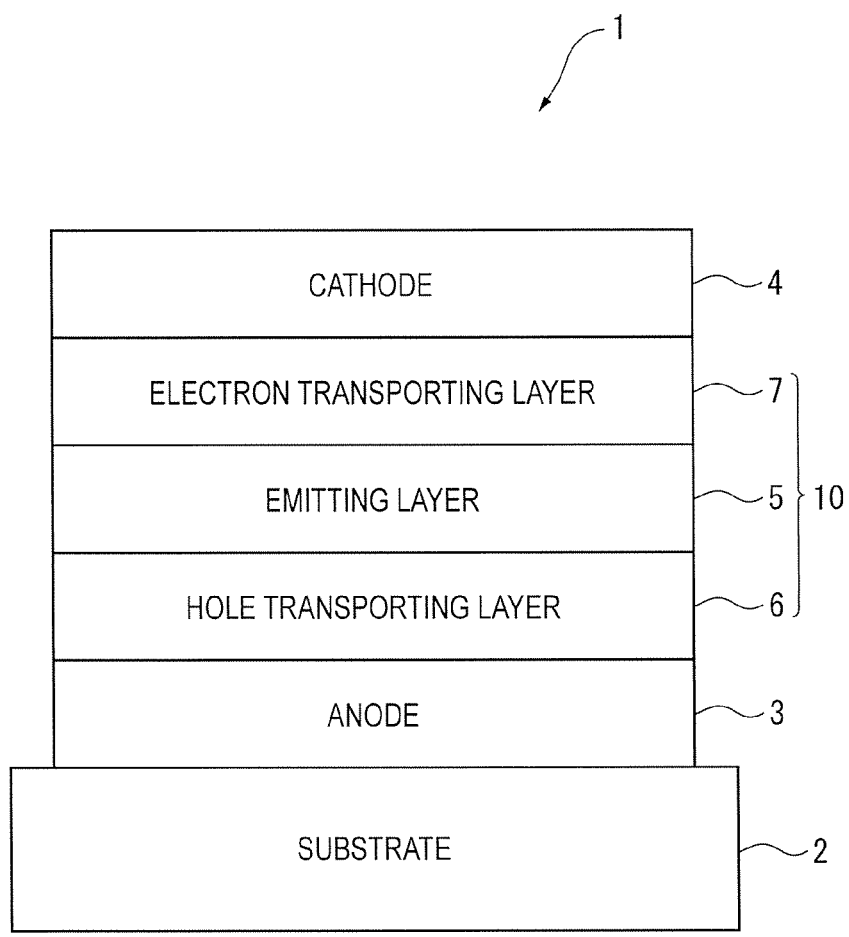

COMPOUND, MATERIAL FOR ORGANIC ELECTROLUMINESCENCE ELEMENT, ORGANIC ELECTROLUMINESCENCE ELEMENT, AND ELECTRONIC APPARATUS

CROSS-REFERENCE TO RELATED APPLICATIONS

This application is a continuation of U.S. patent application Ser. No. 14/902,248, filed on Dec. 30, 2015, which is a National Stage Entry of International Application No. PCT/JP2014/067588, filed on Jul. 1, 2014, which claim priority to Japanese Patent Application No. 2013-138438, filed on Jul. 1, 2013, the disclosures of which are hereby incorporated by reference in their entireties.

TECHNICAL FIELD

The present invention relates to a compound, an organic electroluminescence device material, an organic electroluminescence device, and an electronic apparatus.

BACKGROUND ART

An organic electroluminescence device (hereinafter, occasionally abbreviated as organic EL device) using an organic substance is highly expected to be used as an inexpensive solid-emitting full-color display device having a large area, and has been variously developed. In general, an organic EL device includes a pair of opposing electrodes and an emitting layer between the pair of electrodes. When an electrical field is applied to the opposing electrodes, electrons are injected from a cathode, and holes are injected from an anode. The electrons are then recombined with the holes in the emitting layer to yield an excited state, and energy generated when the excited state returns to a ground state is discharged as light.

As compared with an inorganic light-emitting diode, a typical organic EL device requires a high drive voltage, and the luminescence intensity and luminous efficiency thereof are low. Moreover, since the typical organic EL device is to undergo considerable performance degradation, it has not been in practical use.

Patent Literature 1 discloses a compound having a phenylene group at the center thereof, the phenylene group being bonded to a naphthyl group, an anthryl group or a phenanthrenyl group at one bond while being bonded to a phenyl group at the other bond. The compound has at least one bridge between the phenylene group at the center and the adjacent groups. Patent Literature 1 also discloses an organic EL device using the compound or a heterocyclic derivative of the compound.

CITATION LIST

Patent Literature(s)

Patent Literature 1: WO 2008/006449

SUMMARY OF THE INVENTION

Problems to be Solved by the Invention

However, the organic EL device cannot be in practical use unless the color purity thereof is improved and the lifetime thereof is increased.

An object of the invention is to provide a long-life organic electroluminescence device with a high color purity, a compound usable in the organic electroluminescence device, an organic electroluminescence device material containing the compound, and an electronic apparatus provided with the organic electroluminescence device.

Means for Solving the Problems

A compound according to an aspect of the invention is represented by a formula (1) below.

[Formula 1]

(1)

In the formula (1): n in the formula (1) is 1 or 2; and $Ar^1$ is represented by a formula (2) below.

[Formula 2]

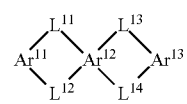
(2)

In the formula (2): $Ar^{11}$, $Ar^{12}$ and $Ar^{13}$ each independently represent a substituted or unsubstituted aromatic hydrocarbon group having 6 to 30 ring carbon atoms; one of $L^{11}$ and $L^{12}$ represents a single bond for bonding $Ar^{11}$ and $Ar^{12}$, and the other one thereof represents a linking group represented by any one of formulae (2a) to (2e) below; and one of $L^{13}$ and $L^{14}$ represents a single bond for bonding $Ar^{12}$ and $Ar^{13}$, and the other one thereof represents a linking group represented by any one of the formulae (2a) to (2e) below.

[Formula 3]

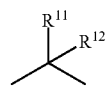
(2a)

(2b)

(2c)

(2d)

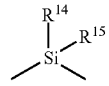
(2e)

In the formulae (2a) to (2e), $R^{11}$ to $R^{15}$ each independently represent a hydrogen atom, a substituted or unsubstituted alkyl group having 1 to 30 carbon atoms, a substituted or unsubstituted aromatic hydrocarbon group having 6 to 30 ring carbon atoms, or a substituted or unsubstituted heterocyclic group having 5 to 30 ring atoms.

$L^2$ and $L^3$ in the formula (1) each independently represent a single bond or a linking group, the linking group being a substituted or unsubstituted aromatic hydrocarbon group having 6 to 30 ring carbon atoms, a substituted or unsubstituted heterocyclic group having 5 to 30 ring atoms, a multiple linking group formed by bonding two groups selected from the group consisting of the aromatic hydrocarbon group, a multiple linking group formed by bonding three groups selected from the group consisting of the aromatic hydrocarbon group, a multiple linking group formed by bonding two groups selected from the group consisting of the heterocyclic group, a multiple linking group formed by bonding three groups selected from the group consisting of the heterocyclic group, a multiple linking group formed by bonding two groups selected from the group consisting of the aromatic hydrocarbon group and the heterocyclic group, or a multiple linking group formed by bonding three groups selected from the group consisting of the aromatic hydrocarbon group and the heterocyclic group.

It should be noted that the aromatic hydrocarbon group or groups and the heterocyclic group or groups in the multiple linking group are mutually the same or different, and adjacent ones of the groups in the multiple linking group are optionally bonded to each other to form a ring or not bonded.

$Ar^2$ in the formula (1) represents a substituted or unsubstituted aromatic hydrocarbon group having 6 to 30 ring carbon atoms, or a substituted or unsubstituted heterocyclic group having 5 to 30 ring atoms.

$Ar^3$ in the formula (1) is represented by a formula (3) below.

[Formula 4]

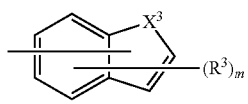

(3)

In the formula (3): $X^3$ represents an oxygen atom or a sulfur atom; m is 5; $R^3$ represents a substituent bonded to a carbon atom of a ring in a structure represented by the formula (3), $R^3$ each independently representing a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, a substituted or unsubstituted arylthio group having 6 to 30 ring carbon atoms, a substituted or unsubstituted aromatic hydrocarbon group having 6 to 30 ring carbon atoms, or a substituted or unsubstituted heterocyclic group having 5 to 30 ring atoms; and adjacent ones of $R^3$ may form a ring or not.

It should be noted that a bond from the structure represented by the formula (3) is bonded to $L^3$ in the formula (1).

According to another aspect of the invention, an organic electroluminescence device material contains the compound of the above aspect.

According to still another aspect of the invention, an organic electroluminescence device includes: a cathode; an anode; and at least one organic layer provided between the cathode and the anode, the organic layer containing the compound of the above aspect.

According to yet another aspect of the invention, an electronic apparatus includes the organic electroluminescence device of the above aspect.

The above aspects of the invention can provide a long-life organic electroluminescence device with a high color purity, a compound usable in the organic electroluminescence device, an organic electroluminescence device material containing the compound, and an electronic apparatus provided with the organic electroluminescence device.

BRIEF DESCRIPTION OF DRAWINGS

The FIGURE schematically shows an exemplary arrangement of an organic electroluminescence device according to an exemplary embodiment.

DESCRIPTION OF EMBODIMENTS

First Exemplary Embodiment

Compound

A compound according to a first exemplary embodiment is represented by a formula (1) below.

[Formula 5]

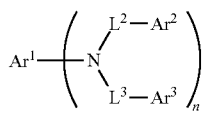

(1)

In the formula (1), n is 1 or 2, and $Ar^1$ is represented by a formula (2) below.

[Formula 6]

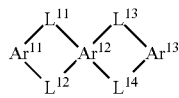

(2)

In the formula (2), $Ar^{11}$, $Ar^{12}$ and $Ar^{13}$ each independently represent a substituted or unsubstituted aromatic hydrocarbon group having 6 to 30 ring carbon atoms, one of $L^{11}$ and $L^{12}$ represents a single bond for bonding $Ar^{11}$ and $Ar^{12}$, and the other one thereof represents a linking group represented by any one of formulae (2a) to (2e) below, and one of $L^{13}$ and $L^{14}$ represents a single bond for bonding $Ar^{12}$ and $Ar^{13}$, and the other one thereof represents a linking group represented by any one of the formulae (2a) to (2e) below.

In the formula (1), at least one of nitrogen atoms bonded to $Ar^1$ is preferably bonded to $Ar^{11}$. For instance, when n is 1, $Ar^{11}$ is preferably bonded to a nitrogen atom as shown in a formula (1A) below.

[Formula 7]

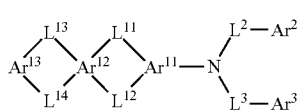
(1A)

[Formula 8]

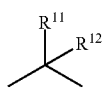
(2a)

(2b)

(2c)

(2d)

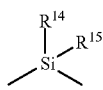
(2e)

In the formulae (2a) to (2e), $R^{11}$ to $R^{15}$ each independently represent a hydrogen atom, a substituted or unsubstituted alkyl group having 1 to 30 carbon atoms, a substituted or unsubstituted aromatic hydrocarbon group having 6 to 30 ring carbon atoms, or a substituted or unsubstituted heterocyclic group having 5 to 30 ring atoms; and In the formula (1), $L^2$ and $L^3$ each independently represent a single bond or a linking group, the linking group being a substituted or unsubstituted aromatic hydrocarbon group having 6 to 30 ring carbon atoms, a substituted or unsubstituted heterocyclic group having 5 to 30 ring atoms, a multiple linking group comprising bonded two groups selected from the group consisting of the aromatic hydrocarbon group, a multiple linking group comprising bonded three groups selected from the group consisting of the aromatic hydrocarbon group, a multiple linking group comprising bonded two groups selected from the group consisting of the heterocyclic group, a multiple linking group comprising bonded three groups selected from the group consisting of the heterocyclic group, a multiple linking group comprising bonded two groups selected from the group consisting of the aromatic hydrocarbon group and the heterocyclic group, or a multiple linking group comprising bonded three groups selected from the group consisting of the aromatic hydrocarbon group and the heterocyclic group.

It should be noted that the aromatic hydrocarbon group or groups and the heterocyclic group or groups in the multiple linking group are mutually the same or different, and adjacent ones of the groups in the multiple linking group may be bonded to each other to form a ring or not bonded.

In the formula (1), $Ar^2$ represents a substituted or unsubstituted aromatic hydrocarbon group having 6 to 30 ring carbon atoms, or substituted or unsubstituted heterocyclic group having 5 to 30 ring atoms.

$Ar^3$ is represented by a formula (3) below.

[Formula 9]

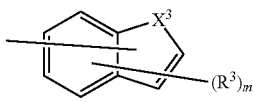
(3)

In the formula (3), $X^3$ represents an oxygen atom or a sulfur atom, m is 5, and $R^3$ represents a substituent bonded to a carbon atom of a ring in a structure represented by the formula (3). $R^3$ each independently represent a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, a substituted or unsubstituted arylthio group having 6 to 30 ring carbon atoms, a substituted or unsubstituted aromatic hydrocarbon group having 6 to 30 ring carbon atoms, or a substituted or unsubstituted heterocyclic group having 5 to 30 ring atoms.

Adjacent ones of $R^3$ may form a ring or not.

It should be noted that a bond from the structure represented by the formula (3) is bonded to $L^3$ in the formula (1).

In the formula (1), when $Ar^3$ is represented by the formula (3), the compound of the formula (1) is represented by a formula (10) below.

[Formula 10]

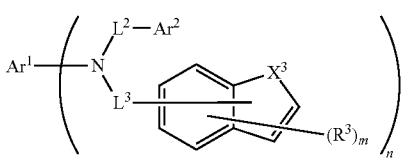
(10)

In the formula (10), $Ar^1$, $Ar^2$, $L^2$ and $L^3$ represent the same as $Ar^1$, $Ar^2$, $L^2$ and $L^3$ in the formula (1), respectively. In the formula (10), $X^3$, $R^3$ and m represent the same as $X^3$, $R^3$ and m in the formula (3), respectively.

In the formula (2), when $Ar^{11}$ is bonded to a nitrogen atom in the formula (1), $Ar^{11}$ is preferably a fused aromatic hydrocarbon group having 10 to 30 ring carbon atoms. In the formula (1A), $Ar^{11}$ is preferably a fused aromatic hydrocarbon group having 10 to 30 ring carbon atoms. When an emitting layer containing a host material and a dopant material, and the compound of the first exemplary embodiment where $Ar^{11}$ is a fused aromatic hydrocarbon group is used as the dopant material, interaction between the host material and the dopant material is supposed to be improved. The compound of the first exemplary embodiment is thus expected to contribute to increasing the lifetime of the organic EL device.

In the formula (2), $Ar^{11}$ to $Ar^{13}$ are preferably a group derived from any one of a substituted or unsubstituted phenyl group, substituted or unsubstituted naphthyl group, substituted or unsubstituted anthryl group, and substituted or unsubstituted phenanthrenyl group. More preferably, Ar$^{11}$ is a group derived from any one of a substituted or unsubstituted naphthyl group, substituted or unsubstituted anthryl group, and substituted or unsubstituted phenanthrenyl group, and Ar$^{12}$ is a group derived from a substituted or unsubstituted phenyl group.

Ar$^1$ in the formula (1) preferably has a skeleton represented by any one selected from the group consisting of formulae (1-1) to (1-22) below.

It should be noted that, when Ar$^1$ has the skeleton represented by any one selected from the group consisting of the formulae (1-1) to (1-22), a carbon atom of the skeleton represented by any one of the formulae (1-1) to (1-22) may be unsubstituted or substituted. Examples of the substituent will be described below.

[Formula 11]

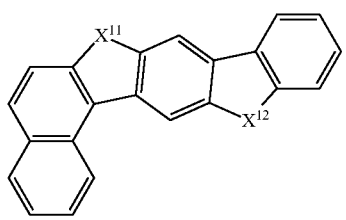
(1-1)

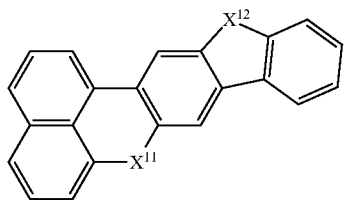
(1-2)

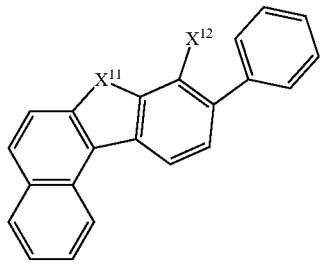
(1-3)

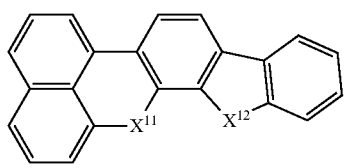
(1-4)

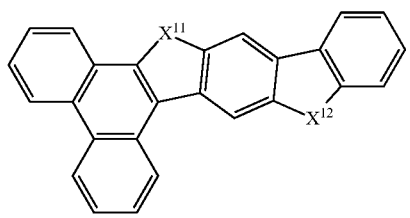
(1-5)

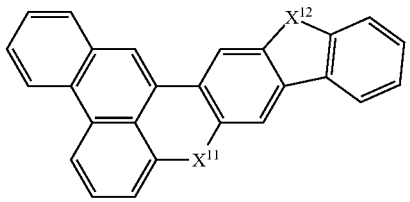
(1-6)

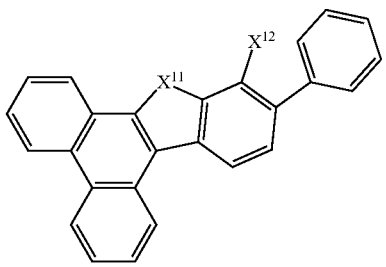
(1-7)

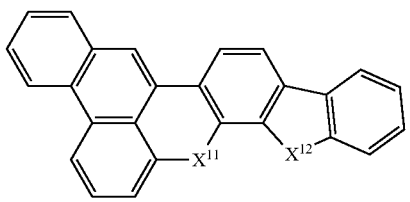
(1-8)

[Formula 12]

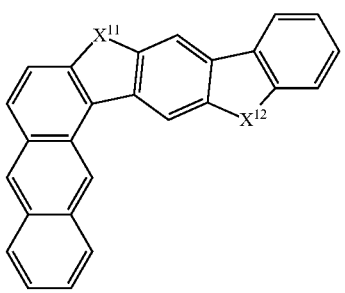
(1-9)

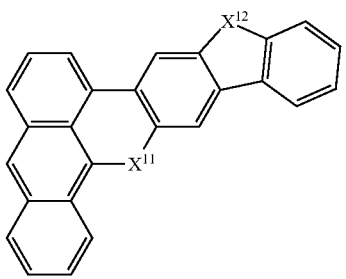
(1-10)

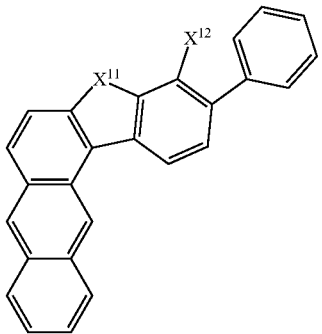
(1-11)

-continued (1-12)
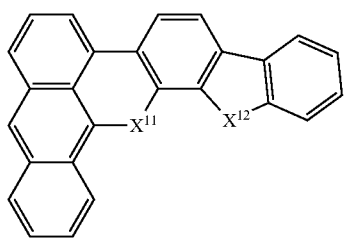

(1-13)
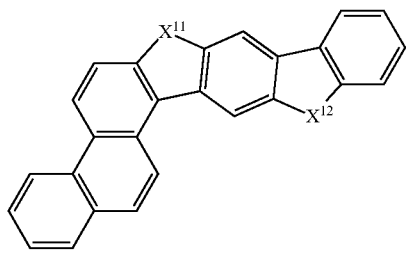

(1-14)
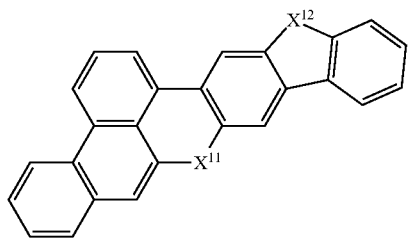

(1-15)
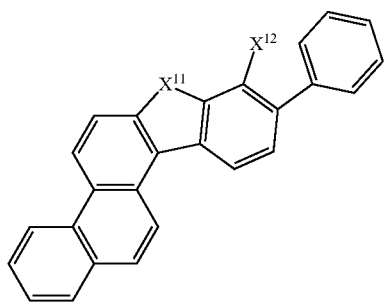

(1-16)
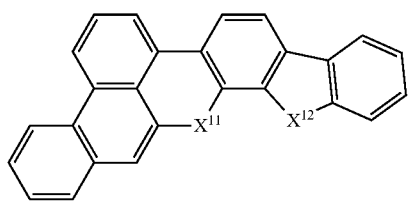

[Formula 13]

(1-17)
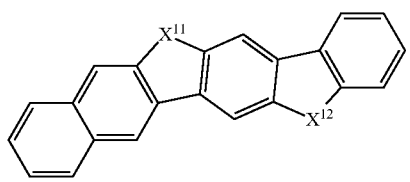

-continued (1-18)
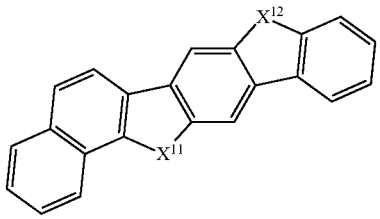

(1-19)
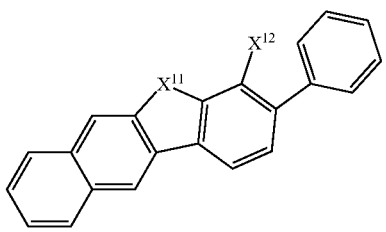

(1-20)
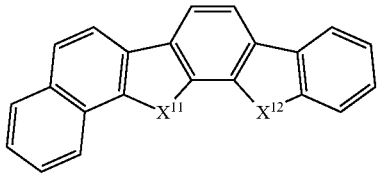

(1-21)
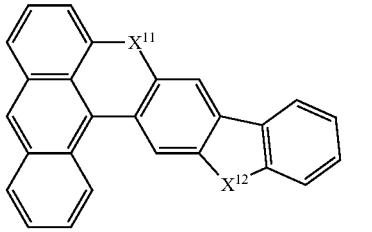

(1-22)
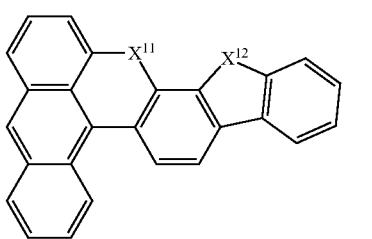

In the formulae (1-1) to (1-22), $X^{11}$ and $X^{12}$ each independently represent a linking group represented by any one of the formulae (2a) to (2e).

n of carbon atoms of the skeleton represented by any one selected from the group consisting of the formulae (1-1) to (1-22) is bonded to a nitrogen atom in the formula (1).

Preferably, n in the formula (1) is 2, and $Ar^1$ in the formula (1) has a skeleton represented by any one selected from the group consisting of formulae (1-31) to (1-34) below.

It should be noted that, when $Ar^1$ has the skeleton represented by any one selected from the group consisting of the formulae (1-31) to (1-34), a carbon atom of the skeleton represented by any one of the formulae (1-31) to (1-34) may be unsubstituted or substituted. Examples of the substituent will be described below.

[Formula 14]

(1-31)
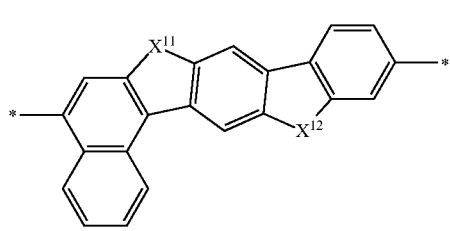

(1-32)
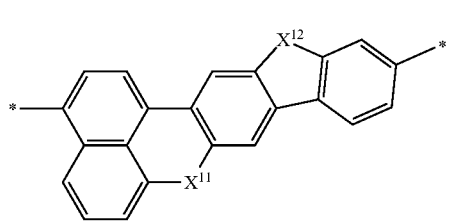

(1-33)
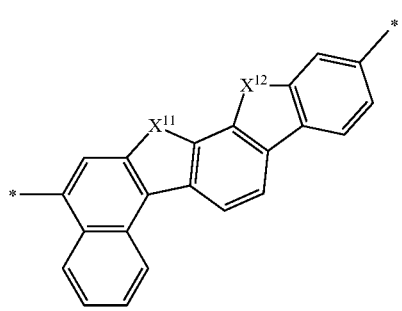

(1-34)
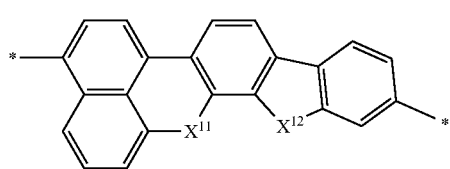

In the formulae (1-31) to (1-34), $X^{11}$ and $X^{12}$ each independently represent a linking group represented by any one of the formulae (2a) to (2e).

at least one of * represents a position at which the skeleton is bonded to a nitrogen atom in the formula (1).

Among skeletons represented by the formulae (1-31) to (1-34), $Ar^1$ preferably has the skeleton represented by the formula (1-31).

Further, in the formulae (1-1) to (1-22) and (1-31) to (1-34), $X^{11}$ and $X^{12}$ are preferably represented by the formula (2a).

In the formula (1), $L^3$ preferably represents a single bond.

Therefore, the formulae (1-31) to (1-34) are preferably represented by formulae (1-41) to (1-52) below, more preferably by the formula (1-41), (1-45) or (1-49).

[Formula 15]

(1-41)
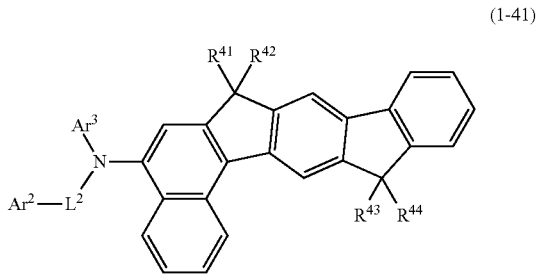

(1-42)
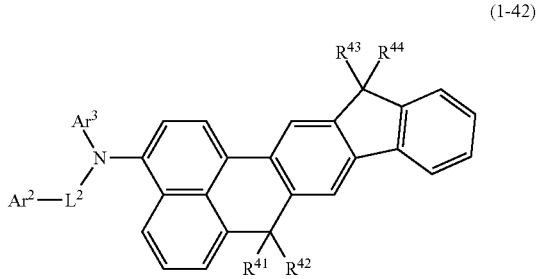

(1-43)
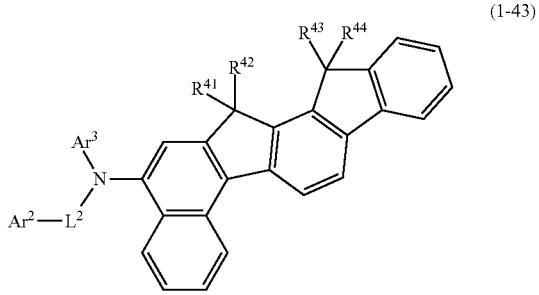

(1-44)
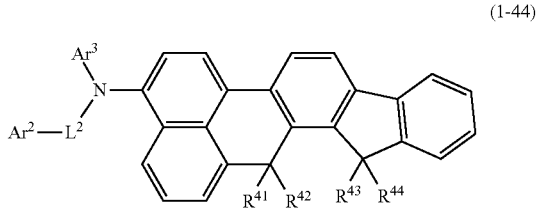

[Formula 16]

(1-45)
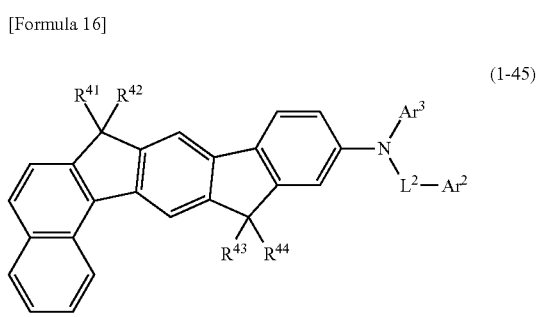

(1-46)
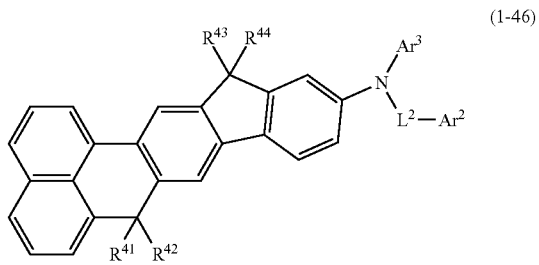

In the formulae (1-41) to (1-52), $L^2$, $Ar^2$ and $Ar^3$ represent the same as $L^2$, $Ar^2$ and $Ar^3$ in the formula (1), respectively. In the formulae (1-49) to (1-52), plural $L^2$ are mutually the same or different. Plural $Ar^2$ are mutually the same or different. Plural $Ar^3$ are mutually the same or different.

$R^{41}$ to $R^{44}$ each independently represent the same as $R^{11}$ and $R^{12}$ in the formula (2a).

$R^{41}$ to $R^{44}$ each independently preferably represent a substituted or unsubstituted alkyl group having 1 to 30 carbon atoms, more preferably a substituted or unsubstituted alkyl group having 1 to 10 carbon atoms, further preferably a substituted or unsubstituted alkyl group having 1 to 6 carbon atoms.

In the formulae (1-49) to (1-52), it is more preferable that plural $L^2$ are mutually the same, plural $Ar^2$ are mutually the same, and plural $Ar^3$ are mutually the same.

In the formula (1) and the formulae (1-41) to (1-52), $Ar^2$ is preferably a substituted or unsubstituted aromatic hydrocarbon group having 6 to 30 ring carbon atoms, preferably a substituted or unsubstituted phenyl group. When the phenyl group has a substituent, the substituent is preferably a substituted or unsubstituted alkyl group having 1 to 20 carbon atoms, or a substituted or unsubstituted phenyl group.

In the formula (1), it is preferable that $Ar^3$ is represented by a formula (4) below. Specifically, when $Ar^3$ is represented by the formula (3), it is preferable that $R^3$ bonded to a five-membered ring are mutually bonded to form a ring, and the formula (3) is represented by the formula (4) below.

[Formula 18]

$$\text{(4)}$$

In the formula (4), $X^4$ represents an oxygen atom or a sulfur atom, s is 7, and $R^4$ represents a substituent bonded to a carbon atom of a ring in a structure represented by the formula (4). $R^4$ each independently represent the same as $R^3$ in the formula (3). Adjacent ones of $R^4$ may form a ring or not. It should be noted that a bond from the structure represented by the formula (4) is bonded to $L^3$ in the formula (1).

In the formula (1), when $Ar^3$ is represented by the formula (4), the compound of the formula (1) is represented by a formula (11) below.

[Formula 19]

$$\text{(11)}$$

In the formula (11), $Ar^1$, $Ar^2$, $L^2$ and $L^3$ represent the same as $Ar^1$, $Ar^2$, $L^2$ and $L^3$ in the formula (1), respectively. $X^4$, $R^4$ and s represent the same as $X^4$, $R^4$ and s in the formula (4), respectively.

Further, $Ar^3$ represented by the formula (4) is preferably represented by a formula (4-1) below, more preferably by a formula (4-2) below. When the compound of the first exemplary embodiment where $Ar^3$ is a group represented by the formula (4-1) is used as the dopant material contained in the emitting layer, the organic EL device emits at a short wavelength, which is preferable. When the compound of the first exemplary embodiment where $Ar^3$ is a group represented by the formula (4-2) is used as the dopant material, the organic EL device emits at a shorter wavelength, which is more preferable.

[Formula 20]

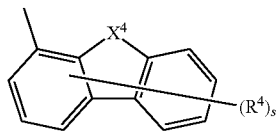

(4-1)

In the formula (4-1), $X^4$, s and $R^4$ represent the same as $X^4$, s and $R^4$ in the formula (4), respectively.

It should be noted that a bond from a structure represented by the formula (4-1) is bonded to $L^3$ in the formula (1).

[Formula 21]

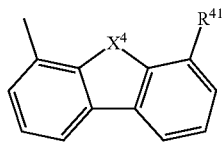

(4-2)

In the formula (4-2), $X^4$ represents the same as $X^4$ in the formula (4).

$R^{41}$ represents a hydrogen atom, an alkyl group having 1 to 20 carbon atoms, or a substituted or unsubstituted aromatic hydrocarbon group having 1 to 30 carbon atoms.

It should be noted that a bond from a structure represented by the formula (4-2) is bonded to $L^3$ in the formula (1).

In the formulae (4), (4-1) and (4-2), $X^4$ preferably represents an oxygen atom.

In the compound represented by the formula (1), $R^{11}$ to $R^{15}$ in the formulae (2a) to (2e) each independently represent a substituted or unsubstituted aromatic hydrocarbon group having 6 to 30 ring carbon atoms, or a substituted or unsubstituted heterocyclic group having 5 to 30 ring atoms.

$R^3$ in the formula (3) each independently represent a hydrogen atom, a halogen atom, a hydroxyl group, a cyano group, a substituted or unsubstituted arylsilyl group having 6 to 60 ring carbon atoms, a substituted or unsubstituted aryloxy group having 6 to 30 ring carbon atoms, a substituted or unsubstituted arylamino group having 6 to 60 ring carbon atoms, a substituted or unsubstituted arylthio group having 6 to 30 ring carbon atoms, a substituted or unsubstituted aromatic hydrocarbon group having 6 to 30 ring carbon atoms, a substituted or unsubstituted heterocyclic group having 5 to 30 ring atoms, or a group represented by a formula (1a) below.

At least one of a substituent of substituted $Ar^2$ and plural $R^3$ is preferably a group represented by the formula (1a).

[Formula 22]

$$-L^{1a}-(R')_t-R \quad (1a)$$

In the formula (1a), $L^{1a}$ represents a single bond or a linking group, the linking group being a divalent group selected from the group consisting of a substituted or unsubstituted aromatic hydrocarbon group having 6 to 18 ring carbon atoms, and a substituted or unsubstituted heterocyclic group having 5 to 15 ring atoms.

R' represents $CR^{101a}R^{102a}$.

R, $R^{101a}$ and $R^{102a}$ each independently represent a hydrogen atom, a halogen atom, a hydroxyl group, a cyano group, a substituted or unsubstituted arylsilyl group having 6 to 60 ring carbon atoms, a substituted or unsubstituted aryloxy group having 6 to 30 ring carbon atoms, a substituted or unsubstituted arylamino group having 6 to 60 ring carbon atoms, a substituted or unsubstituted arylthio group having 6 to 30 ring carbon atoms, a substituted or unsubstituted aromatic hydrocarbon group having 6 to 18 ring carbon atoms, or a substituted or unsubstituted heterocyclic group having 5 to 15 ring atoms.

$R^{101a}$ and $R^{102a}$ may be bonded to each other to form a ring or not bonded.

t is an integer of 4 to 20. Plural R' are mutually the same or different. Adjacent ones of R' may be bonded to each other to form a ring or not bonded. Adjacent ones of $L^{1a}$ and R' may be bonded to each other to form a ring or not bonded. Adjacent ones of R' and R may be bonded to each other to form a ring or not bonded.

When the formula (1) has two or more groups represented by the formula (1a), the substituents represented by the formula (1a) are mutually the same or different.

In the compound represented by the formula (1), $R^{11}$ to $R^{15}$ in the formulae (2a) to (2e) each independently represent a substituted or unsubstituted aromatic hydrocarbon group having 6 to 30 ring carbon atoms, or a substituted or unsubstituted heterocyclic group having 5 to 30 ring atoms.

$R^4$ in the formula (4) each independently represent a hydrogen atom, a halogen atom, a hydroxyl group, a cyano group, a substituted or unsubstituted arylsilyl group having 6 to 60 ring carbon atoms, a substituted or unsubstituted aryloxy group having 6 to 30 ring carbon atoms, a substituted or unsubstituted arylamino group having 6 to 60 ring carbon atoms, a substituted or unsubstituted arylthio group having 6 to 30 ring carbon atoms, a substituted or unsubstituted aromatic hydrocarbon group having 6 to 30 ring carbon atoms, a substituted or unsubstituted heterocyclic group having 5 to 30 ring atoms, or a group represented by a formula (1a) below.

At least one of a substituent of substituted $Ar^2$ and plural $R^4$ is preferably a group represented by the formula (1a) below.

[Formula 23]

$$-L^{1a}-(R')_t-R \quad (1a)$$

In the formula (1a), $L^{1a}$ represents a single bond or a linking group, the linking group being a divalent group selected from the group consisting of a substituted or unsubstituted aromatic hydrocarbon group having 6 to 18 ring carbon atoms, and a substituted or unsubstituted heterocyclic group having 5 to 15 ring atoms.

R' represents $CR^{101a}R^{102a}$.

R, $R^{101a}$ and $R^{102a}$ each independently represent a hydrogen atom, a halogen atom, a hydroxyl group, a cyano group, a substituted or unsubstituted arylsilyl group having 6 to 60 ring carbon atoms, a substituted or unsubstituted aryloxy group having 6 to 30 ring carbon atoms, a substituted or unsubstituted arylamino group having 6 to 60 ring carbon atoms, a substituted or unsubstituted arylthio group having 6 to 30 ring carbon atoms, a substituted or unsubstituted aromatic hydrocarbon group having 6 to 18 ring carbon atoms, or a substituted or unsubstituted heterocyclic group having 5 to 15 ring atoms.

$R^{101a}$ and $R^{102a}$ may be bonded to each other to form a ring or not bonded.

t is an integer of 4 to 20. Plural R' are mutually the same or different. Adjacent ones of R' may be bonded to each other to form a ring or not bonded. Adjacent ones of $L^{1a}$ and R' may be bonded to each other to form a ring or not bonded. Adjacent ones of R' and R may be bonded to each other to form a ring or not bonded.

When the formula (1) has two or more groups represented by the formula (1a), the substituents represented by the formula (1a) are mutually the same or different.

The group represented by the formula (1a) is represented by a formula (1a-1) below.

[Formula 24]

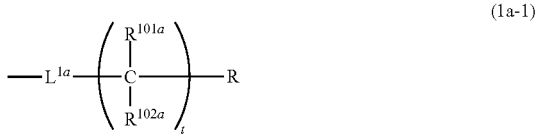

(1a-1)

In the formula (1a-1), $L^{1a}$, $R^{101a}$, $R^{102a}$, R and t represent $L^{1a}$, $R^{110a}$, $R^{102a}$, R and t in the formula (1a), respectively.

The group represented by the formula (1a) is preferably a substituent represented by a formula (1b) below.

[Formula 25]

-$L^{1a}$-($R^{1a}$—$R^{2a}$)$_{tb}$—R    (1b)

In the formula (1b), $L^{1a}$ and R represent the same as $L^{1a}$ and R in the formula (1a), respectively.

In the formula (1b), $R^{1a}$ and $R^{2a}$ each independently represent the same as R' in the formula (1a).

In the formula (1b), tb represents repetition of —$R^{1a}$—$R^{2a}$—, and is an integer of 2 to 10.

Adjacent ones of $R^{1a}$ and $R^{2a}$ may be bonded to each other to form a ring or not bonded.

Adjacent ones of $R^{2a}$ and R may be bonded to each other to form a ring or not bonded.

Adjacent ones of $R^{1a}$ and $L^1$ may be bonded to each other to form a ring or not bonded.

The group represented by the formula (1a) is also preferably a substituent represented by a formula (1c) below.

[Formula 26]

-$L^{1a}$-($R^{1a}$—$R^{2a}$—$R^{3a}$)$_{tc}$—R    (1c)

In the formula (1c), $L^{1a}$ and R represent the same as $L^{1a}$ and R in the formula (1a), respectively.

In the formula (1c), $R^{1a}$, $R^{2a}$ and $R^{3a}$ each independently represent the same as R' in the formula (1a).

In the formula (1c), tc represents repetition of —$R^{1a}$—$R^{2a}$—$R^{3a}$—, and is an integer of 2 to 6.

Adjacent ones of $R^{1a}$ and $R^{2a}$ may be bonded to each other to form a ring or not bonded.

Adjacent ones of $R^{2a}$ and $R^{3a}$ may be bonded to each other to form a ring or not bonded.

Adjacent ones of $R^{3a}$ and R may be bonded to each other to form a ring or not bonded.

Adjacent ones of $R^{1a}$ and $L^1$ may be bonded to each other to form a ring or not bonded.

In the formula (1a), R' preferably represents a methylene group.

In the compound represented by the formula (1), $R^3$ in the formula (3) represents a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, a substituted or unsubstituted arylthio group having 6 to 30 ring carbon atoms, a substituted or unsubstituted aromatic hydrocarbon group having 6 to 30 ring carbon atoms, a substituted or unsubstituted heterocyclic group having 5 to 30 ring atoms, or a group represented by a formula (11a) below.

At least one of a substituent of substituted $Ar^2$ and plural $R^3$ may be preferably a group represented by the formula (11a) below.

[Formula 27]

—(Ar)$_u$—$R^{11}$    (11a)

In the formula (11a), Ar represents a substituted or unsubstituted divalent aromatic hydrocarbon group having 6 to 18 ring carbon atoms, or a substituted or unsubstituted divalent heterocyclic group having 5 to 15 ring atoms.

u is an integer of 3 to 20, and plural Ar are mutually the same or different.

Adjacent ones of Ar may be bonded to each other to form a ring or not bonded.

Adjacent ones of Ar and $R^{11a}$ may be bonded to each other to form a ring or not bonded.

$R^{11a}$ represents a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms.

In the compound represented by the formula (1), $R^4$ in the formula (4) represents a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, a substituted or unsubstituted arylthio group having 6 to 30 ring carbon atoms, a substituted or unsubstituted aromatic hydrocarbon group having 6 to 30 ring carbon atoms, a substituted or unsubstituted heterocyclic group having 5 to 30 ring atoms, or a group represented by a formula (11a) below.

At least one of a substituent of substituted $Ar^2$ and plural $R^4$ may be preferably a group represented by the formula (11a) below.

[Formula 28]

$$—(Ar)_u—R^{11a} \quad (11a)$$

In the formula (11a), Ar represents a substituted or unsubstituted divalent aromatic hydrocarbon group having 6 to 18 ring carbon atoms, or a substituted or unsubstituted divalent heterocyclic group having 5 to 15 ring atoms.

u is an integer of 3 to 20, and plural Ar are mutually the same or different.

Adjacent ones of Ar may be bonded to each other to form a ring or not bonded. Adjacent ones of Ar and $R^{11a}$ may be bonded to each other to form a ring or not bonded.

$R^{11a}$ represents a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms.

Ar in the formula (11a) preferably represents a structure selected from the group consisting of structures represented by formulae (Ar-1-1) to (Ar-1-23) below, more preferably the structure represented by the formula (Ar-1-1).

[Formula 29]

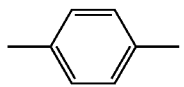
Ar-1-1

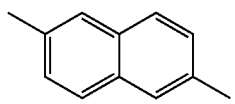
Ar-1-2

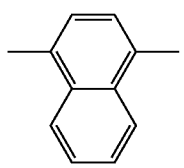
Ar-1-3

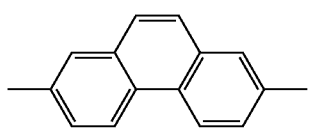
Ar-1-4

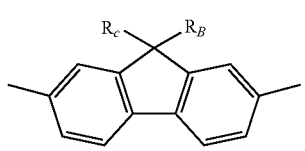
Ar-1-5

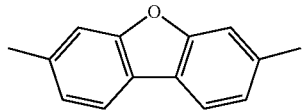
Ar-1-6

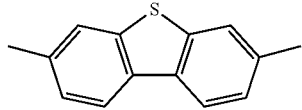
Ar-1-7

[Formula 30]

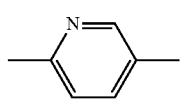
Ar-1-8

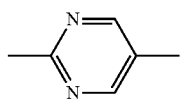
Ar-1-9

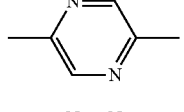
Ar-1-10

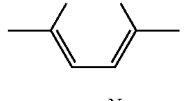
Ar-1-11

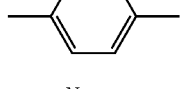
Ar-1-12

Ar-1-13

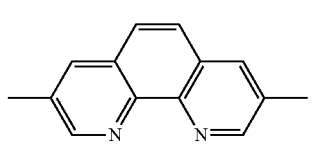
Ar-1-14

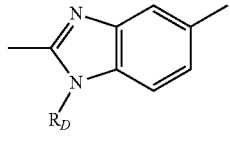
Ar-1-15

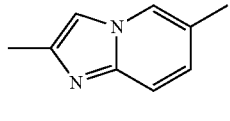
Ar-1-16

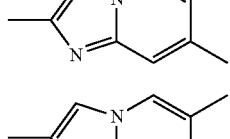
Ar-1-17

Ar-1-18

-continued

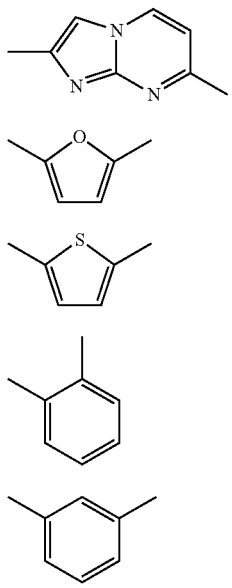

Ar-1-19

Ar-1-20

Ar-1-21

Ar-1-22

Ar-1-23

$R_B$ and $R_C$ in the formula (Ar-1-5) each independently represent an unsubstituted methyl group or an unsubstituted phenyl group. $R_D$ in the formula (Ar-1-15) represents an unsubstituted methyl group or an unsubstituted phenyl group.

The group represented by the formula (11a) is preferably represented by a formula (11b) below.

[Formula 31]

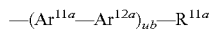

$-(Ar^{11a}-Ar^{12a})_{ub}-R^{11a}$ (11b)

In the formula (11b), $R^{11a}$ represents the same as $R^{11a}$ in the formula (11a).

$Ar^{11a}$ and $Ar^{12a}$ each independently represent a substituted or unsubstituted divalent aromatic hydrocarbon group having 6 to 18 ring carbon atoms, or a substituted or unsubstituted divalent heterocyclic group having 5 to 15 ring atoms.

ub represents repetition of $-Ar^{11a}-Ar^{12a}-$, and is an integer of 2 to 10.

A moiety represented by $-Ar^{11a}-Ar^{12a}-$ in the substituent represented by the formula (11b) preferably has a structure selected from the group consisting of structures represented by formulae (Ar-2-1) to (Ar-2-5) below.

[Formula 32]

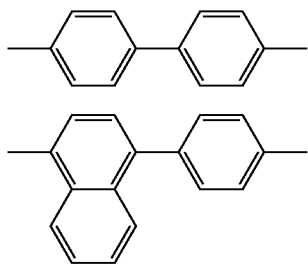

Ar-2-1

Ar-2-2

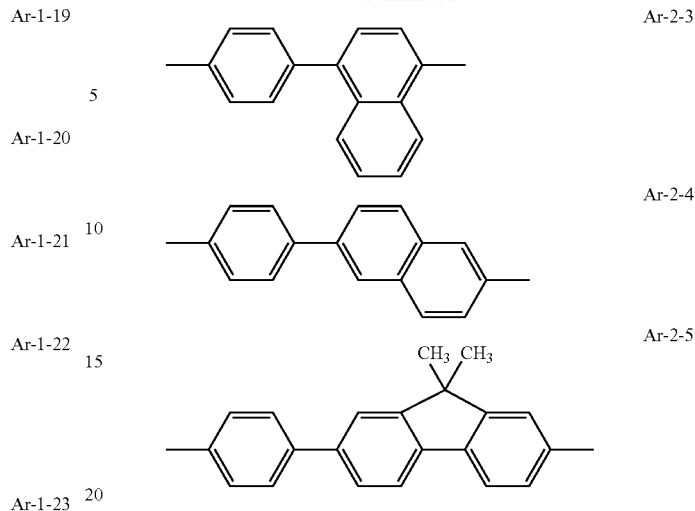

Ar-2-3

Ar-2-4

Ar-2-5

The group represented by the formula (11a) is also preferably represented by a formula (11c) below.

[Formula 33]

$-(Ar^{13a}-Ar^{14a}-Ar^{15a})_{uc}-R^{11a}$ (11c)

In the formula (11c), $R^{11a}$ represents the same as $R^{11a}$ in the formula (11a). $Ar^{13a}$, $Ar^{14a}$ and $Ar^{15a}$ each independently represent a substituted or unsubstituted divalent aromatic hydrocarbon group having 6 to 18 ring carbon atoms, or a substituted or unsubstituted divalent heterocyclic group having 5 to 15 ring atoms.

uc represents repetition of $-Ar^{13a}-Ar^{14a}-Ar^{15a}-$, and is an integer of 2 to 6.

A moiety represented by $-Ar^{13a}-Ar^{14a}-Ar^{15a}-$ in the substituent represented by the formula (11c) preferably has a structure selected from the group consisting of structures represented by formulae (Ar-3-1) to (Ar-3-11) below.

[Formula 34]

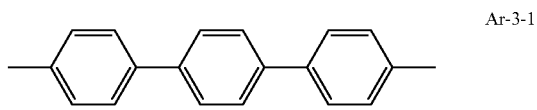

Ar-3-1

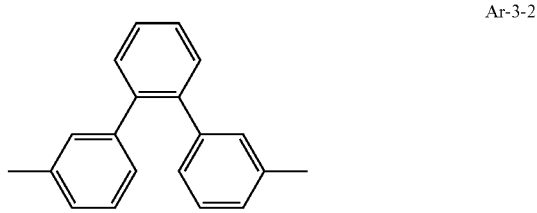

Ar-3-2

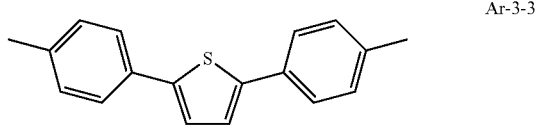

Ar-3-3

[Formula 35]

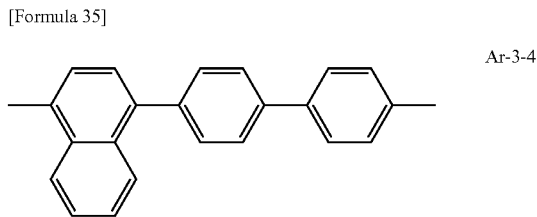

Ar-3-4

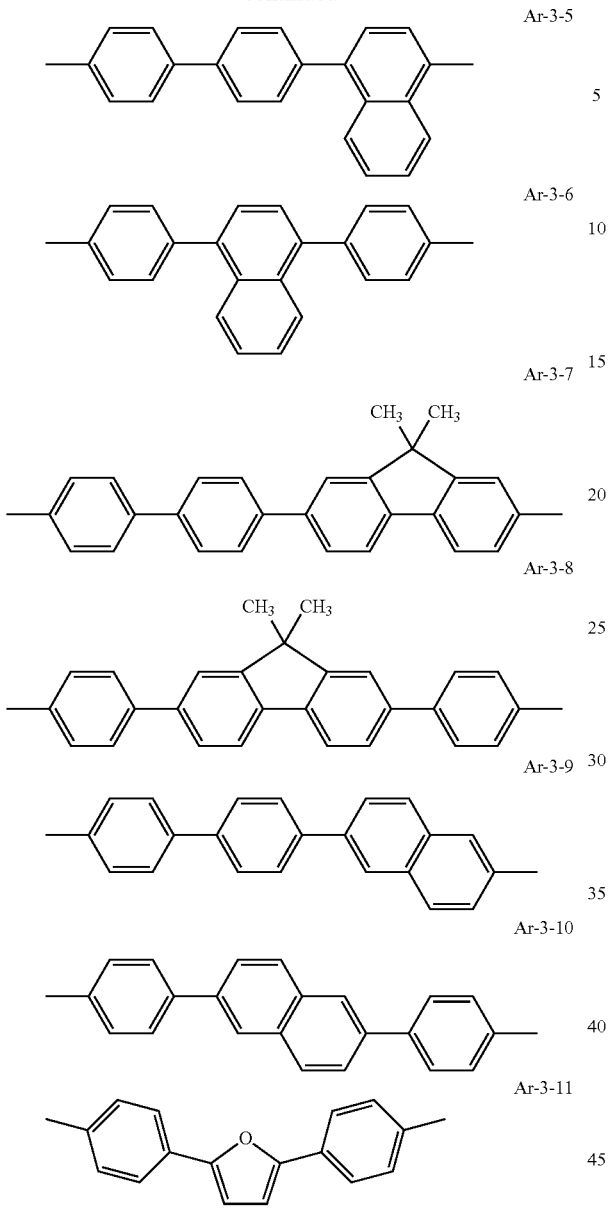

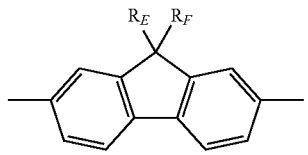

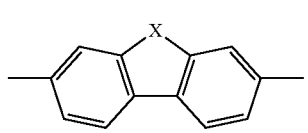

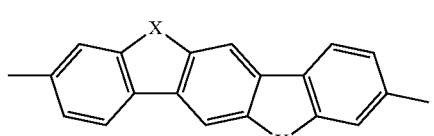

A structure represented by —(Ar)$_{ua}$— in the formula (11a), a structure represented by —(Ar$_1$—Ar$_2$)$_{ub}$— in the formula (11b), and a structure represented by —(Ar$_1$—Ar$_2$—Ar$_3$)$_{uc}$— in the formula (11c) each preferably include 4 to 20 mutually bonded monocyclic rings and fused rings of the aromatic hydrocarbon group and the heterocyclic group, more preferably 5 to 20 mutually bonded monocyclic rings and fused rings, particularly preferably 6 to 20 mutually bonded monocyclic rings and fused rings. Here, the term "bonded" means that aromatic rings with a (4 n+2)π electron system are mutually bonded by a single bond, and a fused ring with a (4n+2)π electron system is counted as one ring irrespective of the number of rings that are fused. Here, n is an integer of 0 or more. For instance, a naphthylene group having 10 π-electrons is counted as one. Groups represented by formulae (A) to (C) below each have a structure where 6π-electron benzene rings are bonded together by a single bond, so that the group represented by the formula (A) or (B) is counted as two, and the group represented by the formula (C) is counted as three. Similarly, a biphenyl group, which has two phenylene groups (i.e., monocyclic aromatic hydrocarbon groups), is counted as two.

[Formula 36]

In the formula (A), R$_E$ and RF each independently represent an unsubstituted methyl group or an unsubstituted phenyl group.

In the formulae (B) and (C), X and Y each independently represent an oxygen atom, a sulfur atom, a carbonyl group, NR$_G$, CR$_H$R$_I$, SiR$_J$R$_K$ or GeR$_L$R$_M$.

R$_G$ to R$_M$ each independently represent the same as R$^{31}$ to R$^{34}$ in the formula (21).

Next, substituents for the formulae (1) to (4), (4-1), (4-2), (1-1) to (1-22), (1-31) to (1-34), (1-41) to (1-52), (1a) to (1c), (1a-1), (2a), (2b), (2e), (10), (11), (11a) to (1c), (Ar1-5) and (Ar-1-15) will be described.

Herein, the number of carbon atoms forming a ring (also referred to as ring carbon atoms) means the number of carbon atoms included in atoms forming the ring itself of a compound in which the atoms are bonded to form the ring (e.g., a monocyclic compound, a fused ring compound, a cross-linked compound, a carbocyclic compound, and a heterocyclic compound). When the ring is substituted by a substituent, carbon atom(s) included in the substituent is not counted as the ring carbon atoms. The same applies to the "ring carbon atoms" described below, unless particularly noted. For instance, a benzene ring has 6 ring carbon atoms, a naphthalene ring has 10 ring carbon atoms, a pyridinyl group has 5 ring carbon atoms, and a furanyl group has 4 ring carbon atoms. When a benzene ring or a naphthalene ring is substituted, for instance, by an alkyl group, the carbon atoms of the alkyl group are not counted as the ring carbon atoms. For instance, when a fluorene ring (inclusive of a spirofluorene ring) is bonded as a substituent to a fluorene ring, the carbon atoms of the fluorene ring as a substituent are not counted as the ring carbon atoms.

Herein, the number of atoms forming a ring (also referred to as ring atoms) means the number of atoms forming the ring itself of a compound in which the atoms are bonded to form the ring (e.g., a monocyclic compound, a fused ring compound, a cross-linked compound, a carbocyclic compound, and a heterocyclic compound). Atom(s) not forming the ring (e.g., hydrogen atom(s) for saturating the valence of the atom which forms the ring) and atom(s) in a substituent by which the ring is substituted are not counted as the ring atoms. The same applies to the "ring atoms" described below, unless particularly noted. For instance, a pyridine ring has 6 ring atoms, a quinazoline ring has 10 ring atoms, and a furan ring has 5 ring atoms. Hydrogen atoms respectively bonded to carbon atoms of the pyridine ring or the quinazoline ring and atoms forming a substituent are not counted as the ring atoms. For instance, when a fluorene ring (inclusive of a spirofluorene ring) is bonded as a substituent to a fluorene ring, the atoms of the fluorene ring as a substituent are not included in the ring atoms.

Next, the substituents for the above formulae will be described.

In the first exemplary embodiment, examples of the aromatic hydrocarbon group (occasionally referred to as "aryl group") having 6 to 30 ring carbon atoms include a phenyl group, biphenyl group, terphenyl group, naphthyl group, anthryl group, phenanthryl group, fluorenyl group, pyrenyl group, chrysenyl group, fluoranthenyl group, benzo[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

The aromatic hydrocarbon group in the first exemplary embodiment preferably has 6 to 20 ring carbon atoms, more preferably 6 to 12 ring carbon atoms. Among the above aryl group, a phenyl group, biphenyl group, naphthyl group, phenanthryl group, terphenyl group, and fluorenyl group are particularly preferable. A carbon atom at a position 9 of each of 1-fluorenyl group, 2-fluorenyl group, 3-fluorenyl group and 4-fluorenyl group is preferably substituted by a substituted or unsubstituted alkyl group having 1 to 30 carbon atoms or a substituted or unsubstituted aryl group having 6 to 18 ring carbon atoms, which are later described in the first exemplary embodiment.

It should be noted that examples of the aromatic hydrocarbon group having 6 to 18 ring carbon atoms for the formula (1a) and the like include ones having 6 to 18 ring carbon atoms of the aromatic hydrocarbon groups having 6 to 30 ring carbon atoms.

The heterocyclic group (occasionally, referred to as heteroaryl group, heteroaromatic cyclic group, or aromatic heterocyclic group) having 5 to 30 ring atoms in the first exemplary embodiment preferably has at least one atom selected from the group consisting of nitrogen, sulfur, oxygen, silicon, selenium atom, and germanium atom as a hetero atom, more preferably at least one atom selected from the group consisting of nitrogen, sulfur and oxygen.

Examples of the heterocyclic group having 5 to 30 ring atoms in the first exemplary embodiment include a pyridyl group, pyrimidinyl group, pyrazinyl group, pyridazinyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazole group, benzofuranyl group, benzothiophenyl group, benzoxazolyl group, benzothiazolyl group, benzisoxazolyl group, benzisothiazolyl group, benzoxadiazolyl group, benzothiadiazolyl group, dibenzofuranyl group, dibenzothiophenyl group, piperidinyl group, pyrrolidinyl group, piperazinyl group, morpholyl group, phenazinyl group, phenothiazinyl group, and phenoxazinyl group.

The heterocyclic group in the first exemplary embodiment preferably has 5 to 20 ring atoms, more preferably 5 to 14 ring atoms. Among the above heterocyclic group, a 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-carbazolyl group, 2-carbazolyl group, 3-carbazolyl group, 4-carbazolyl group, and 9-carbazolyl group are particularly preferable. A nitrogen atom at a position 9 of each of 1-carbazolyl group, 2-carbazolyl group, 3-carbazolyl group and 4-carbazolyl group is preferably substituted by a substituted or unsubstituted aromatic hydrocarbon group having 6 to 30 ring carbon atoms or a substituted or unsubstituted heterocyclic group having 5 to 30 ring atoms in the first exemplary embodiment.

It should be noted that examples of the heterocyclic group having 5 to 15 ring atoms for the formula (1a) and the like include ones having 5 to 15 ring atoms of the heterocyclic groups having 5 to 30 ring atoms.

The alkyl group having 1 to 30 carbon atoms in the exemplary embodiment is preferably linear, branched or cyclic. Examples of the linear or branched alkyl group include: a methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, amyl group, isoamyl group, 1-methylpentyl group, 2-methylpentyl group, 1-pentylhexyl group, 1-butylpentyl group, 1-heptyloctyl group, and 3-methylpentyl group.

The linear or branched alkyl group in the exemplary embodiment preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group, n-hexyl group, amyl group, isoamyl group, and neopentyl group are particularly preferable.

Examples of the cycloalkyl group in the exemplary embodiment include a cyclopropyl group, cyclobutyl group, cyclopentyl group, cyclohexyl group, 4-methylcyclohexyl group, adamantyl group and norbornyl group. The cycloalkyl group preferably has 3 to 10 ring carbon atoms, more preferably 5 to 8 ring carbon atoms. Among the above cycloalkyl group, a cyclopentyl group and a cyclohexyl group are particularly preferable.

The halogenated alkyl group provided by substituting the alkyl group with a halogen atom is exemplified by a halogenated alkyl group obtained by substituting the alkyl group having 1 to 30 carbon atoms with one or more halogen atoms. Specific examples of the halogenated alkyl group includes a fluoromethyl group, difluoromethyl group, trifluoromethyl group, fluoroethyl group, trifluoromethylmethyl group, trifluoroethyl group, and pentafluoroethyl group.

The alkylsilyl group having 3 to 30 carbon atoms in the exemplary embodiment is exemplified by a trialkylsilyl group having the above alkyl group having 1 to 30 carbon atoms. Specific examples of the trialkylsilyl group include a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyldimethylsilyl group, propyldimethylsilyl group and triisopropylsilyl group. Three alkyl groups in the trialkylsilyl group may be mutually the same or different.

Examples of the arylsilyl group having 6 to 60 ring carbon atoms in the exemplary embodiment include a dialkylarylsilyl group, alkyldiarylsilyl group and triarylsilyl group.

The dialkylarylsilyl group is exemplified by a dialkylarylsilyl group including two of the alkyl groups listed as the examples of the alkyl group having 1 to 30 carbon atoms and one of the aromatic hydrocarbon groups having 6 to 30 ring carbon atoms. The dialkylarylsilyl group preferably has 8 to 30 carbon atoms.

The alkyldiarylsilyl group is exemplified by an alkyldiarylsilyl group including one of the alkyl groups listed as the examples of the alkyl group having 1 to 30 carbon atoms and two of the aromatic hydrocarbon groups having 6 to 30 ring carbon atoms. The alkyldiarylsilyl group preferably has 13 to 30 carbon atoms.

The triarylsilyl group is exemplified by a triarylsilyl group having three of the aromatic hydrocarbon groups listed above as the aromatic hydrocarbon group having 6 to 30 ring carbon atoms. The triarylsilyl group preferably has 18 to 30 carbon atoms.

The alkoxy group having 1 to 30 carbon atoms in the exemplary embodiment is represented by $-OZ_1$. $Z_1$ is exemplified by the above alkyl group having 1 to 30 carbon atoms. Examples of the alkoxy group include a methoxy group, ethoxy group, propoxy group, butoxy group, pentyloxy group and hexyloxy group.

The halogenated alkoxy group provided by substituting the alkoxy group with a halogen atom is exemplified by a halogenated alkoxy group obtained by substituting the alkoxy group having 1 to 30 carbon atoms with one or more halogen atoms.

The aryloxy group having 6 to 30 ring carbon atoms in the exemplary embodiment is represented by $-OZ_2$. $Z_2$ is exemplified by the aromatic hydrocarbon group having 6 to 30 ring carbon atoms, or one of a monocyclic group and a fused ring group (described later). The aryloxy group is exemplified by a phenoxy group.

The alkylamino group having 2 to 30 carbon atoms in the first exemplary embodiment is represented by $-NHR_V$ or $-N(R_V)_2$. $R_V$ is exemplified by the above alkyl group having 1 to 30 carbon atoms.

The arylamino group having 6 to 60 ring carbon atoms in the first exemplary embodiment is represented by $-NH_2R_W$ or $-NH(R_W)_2$. $R_W$ is exemplified by the above aromatic hydrocarbon group having 6 to 30 ring carbon atoms.

The alkylthio group having 1 to 30 carbon atoms in the first exemplary embodiment is represented by $-SR_V$. $R_V$ is exemplified by the above alkyl group having 1 to 30 carbon atoms.

The arylthio group having 6 to 30 ring carbon atoms is represented by $-SR_W$. $R_W$ is exemplified by the above aromatic hydrocarbon group having 6 to 30 ring carbon atoms.

Examples of the halogen atom in the first exemplary embodiment are fluorine, chlorine, bromine and iodine, among which a fluorine atom is preferable.

In the first exemplary embodiment, "carbon atoms forming a ring (ring carbon atoms)" means carbon atoms forming a saturated ring, an unsaturated ring, or an aromatic ring. "Atoms forming a ring (ring atoms)" means carbon atoms and hetero atoms forming a hetero ring including a saturated ring, unsaturated ring, or aromatic ring.

In the first exemplary embodiment, a hydrogen atom includes isotopes having different numbers of neutrons, i.e., protium, deuterium and tritium.

In the first exemplary embodiment, examples of the substituents meant by "substituted or unsubstituted" include an alkyl group (linear or branched alkyl group, cycloalkyl group and haloalkyl group), alkoxy group, aryloxy group, aralkyl group, haloalkoxy group, alkylsilyl group, dialkylarylsilyl group, alkyldiarylsilyl group, triarylsilyl group, halogen atom, cyano group, hydroxyl group, nitro group and carboxy group in addition to the above aromatic hydrocarbon group and heterocyclic group. In addition, an alkenyl group and an alkynyl group are available.

Among the above substituents, the aromatic hydrocarbon group, heterocyclic group, alkyl group, halogen atom, alkylsilyl group, arylsilyl group and cyano group are preferable. More preferred substituents are the preferred substituents specifically described for each substituent.

The substituents meant by "substituted or unsubstituted" may further be substituted by any one of the above substituents. Two or more of the substituents meant by "substituted or unsubstituted" may be bonded to form a ring.

"Unsubstituted" in "substituted or unsubstituted" herein means that a group is not substituted by any one of the above substituents but bonded with a hydrogen atom.

In the first exemplary embodiment, "XX to YY carbon atoms" in the expression of "substituted or unsubstituted ZZ group having XX to YY carbon atoms" represents carbon atoms of an unsubstituted ZZ group and do not include carbon atoms of a substituent(s) of the substituted ZZ group. "YY" is larger than "XX" and each of "XX" and "YY" represents an integer of 1 or more.

In the first exemplary embodiment, "XX to YY atoms" in the expression of "substituted or unsubstituted ZZ group having XX to YY atoms" represents atoms of an unsubstituted ZZ group and does not include atoms of a substituent(s) of the substituted ZZ group. "YY" is larger than "XX" and each of "XX" and "YY" represents an integer of 1 or more.

The same applies to the expression "substituted or unsubstituted" used in the description of the following compound(s) or a partial structure(s) thereof.

Specific examples of the compound represented by the formula (1) are shown below, but the invention is not limited thereto.
[Formula 37]
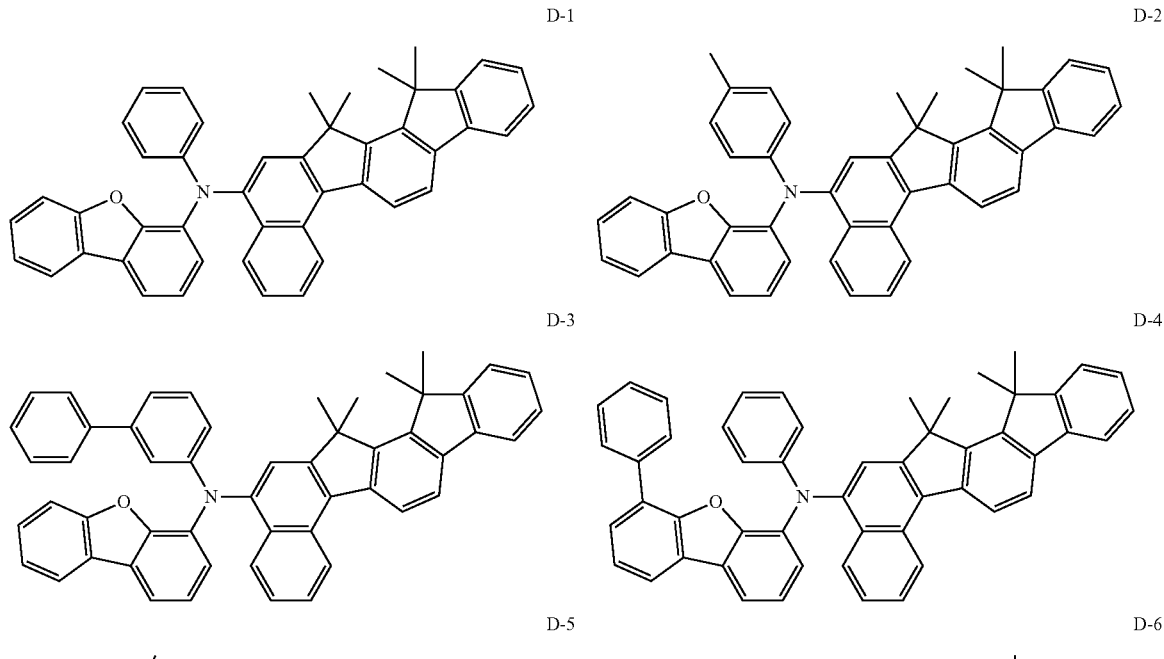
[Formula 38]
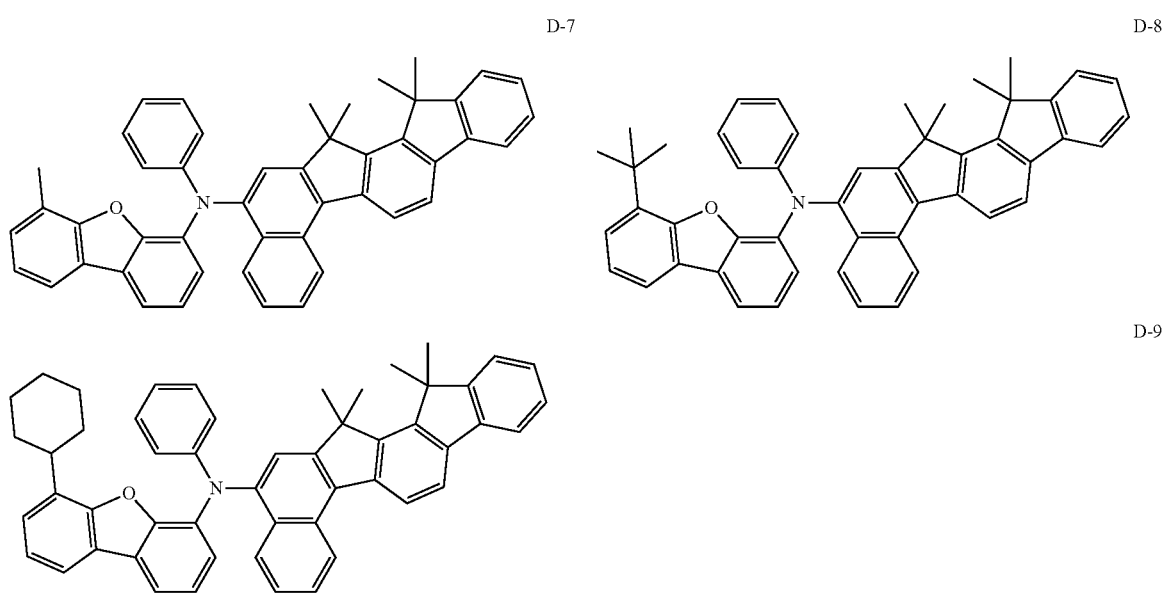

-continued
D-10
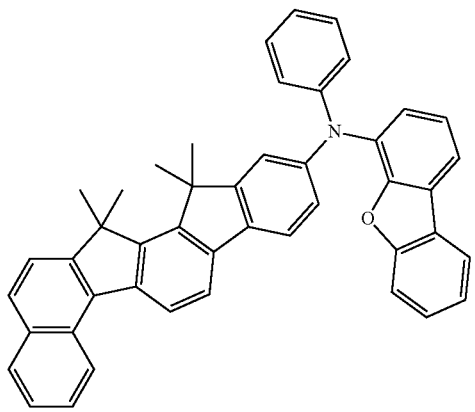
D-11
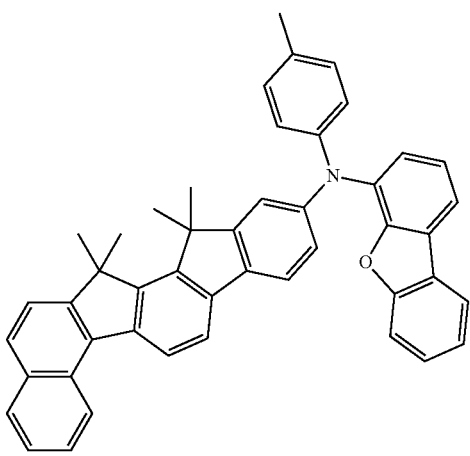
D-12
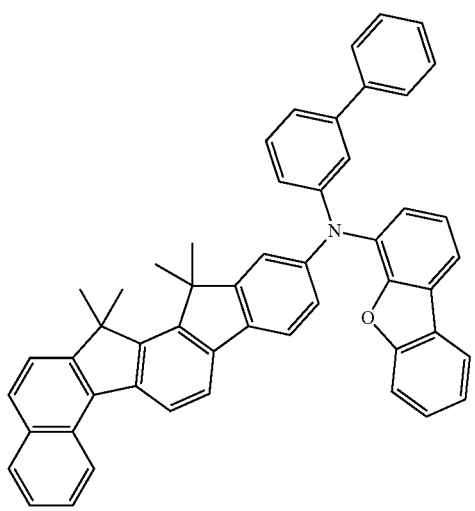
[Formula 39]
D-13
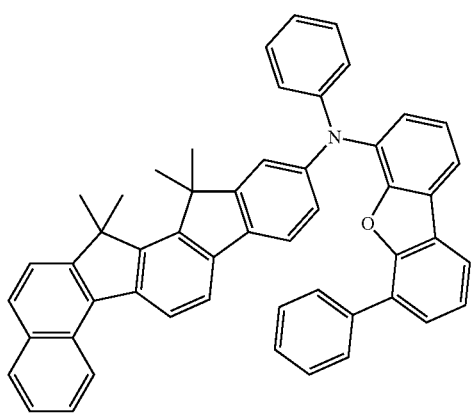
D-14
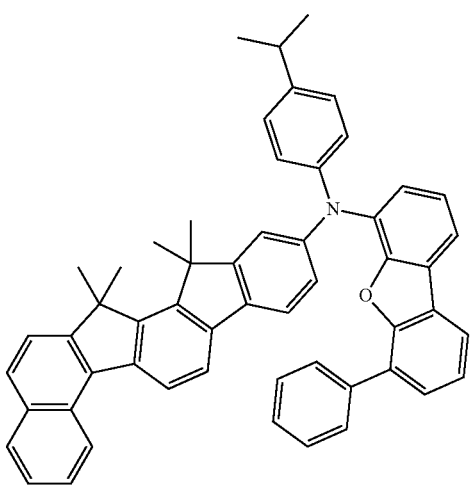

-continued
D-15
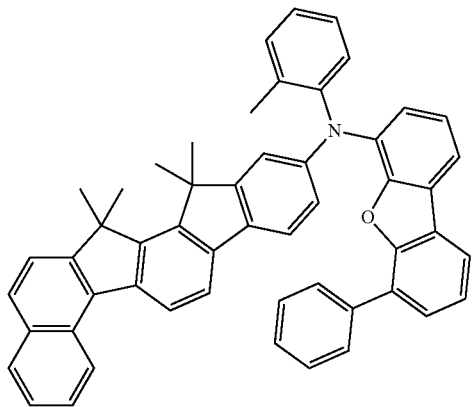
D-16
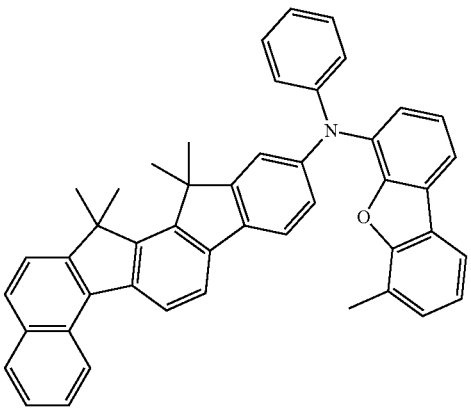
D-17
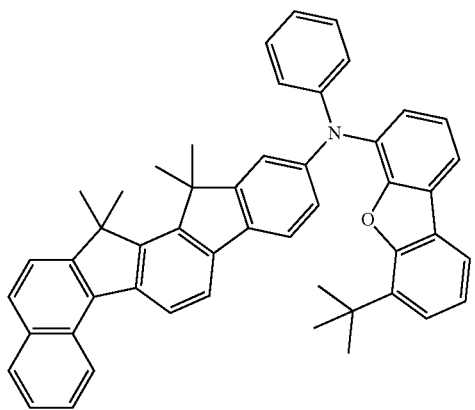
D-18
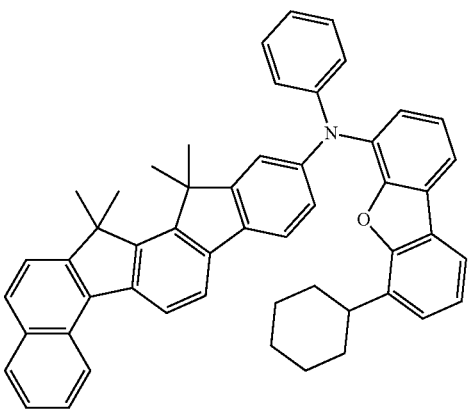
[Formula 40]
D-19
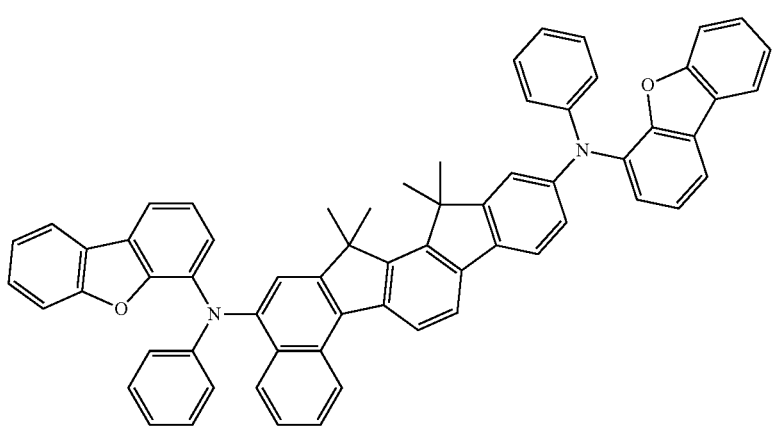

D-20
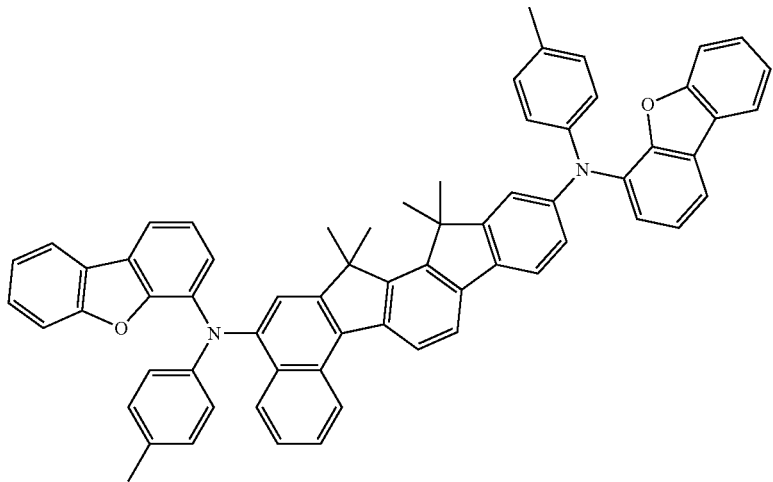
D-21
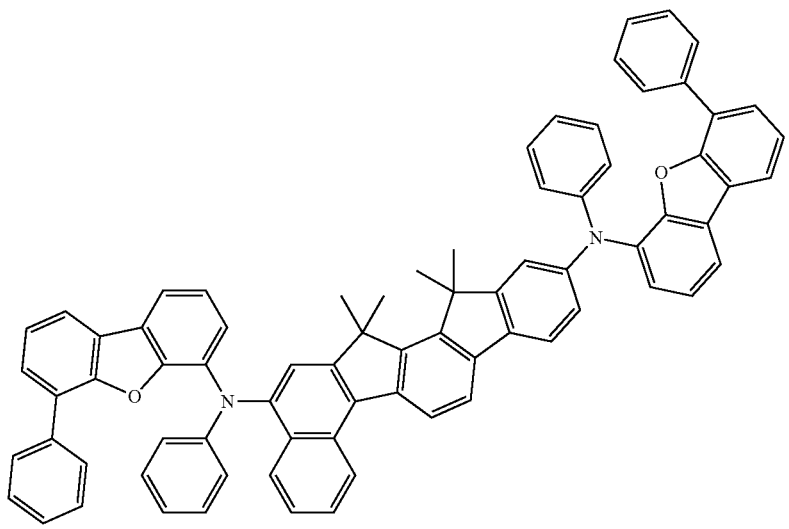
D-22
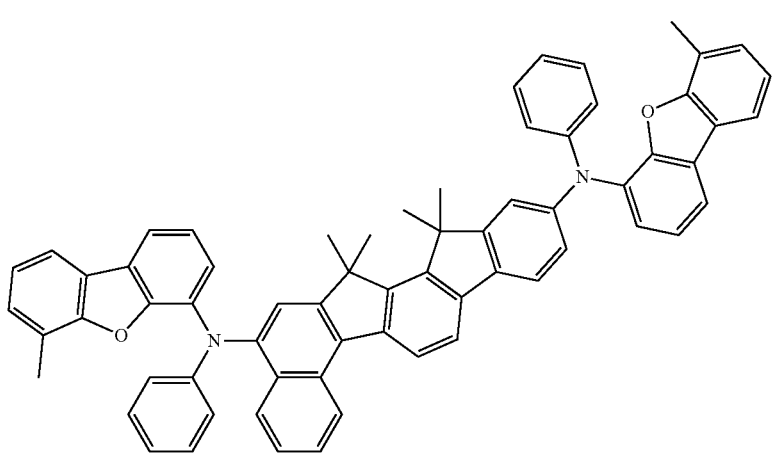

[Formula 41]
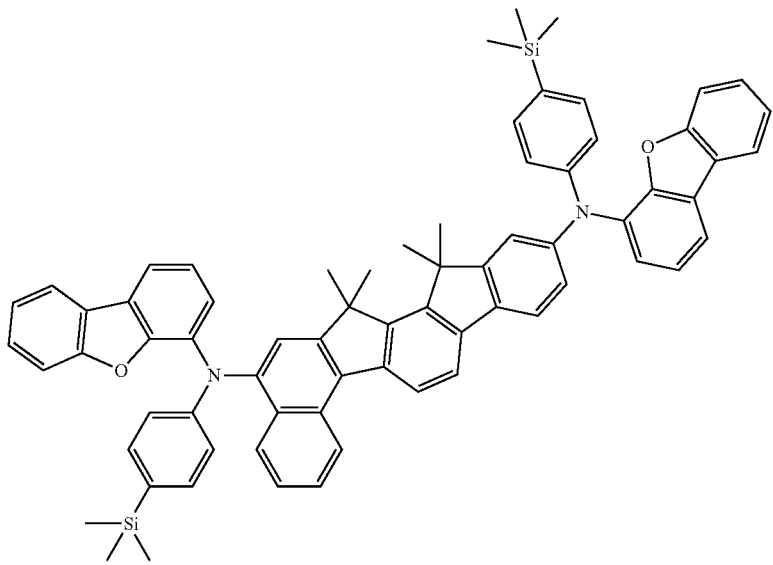
D-23
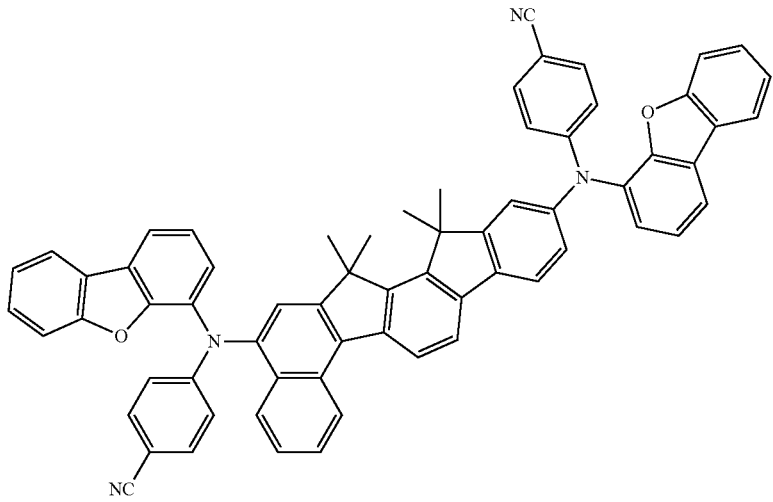
D-24
[Formula 42]
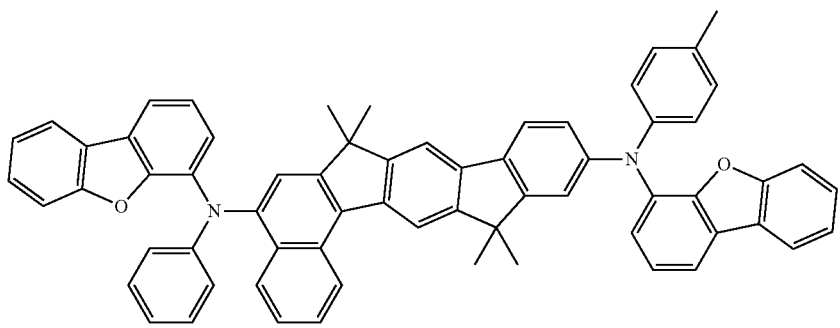
C-1

-continued
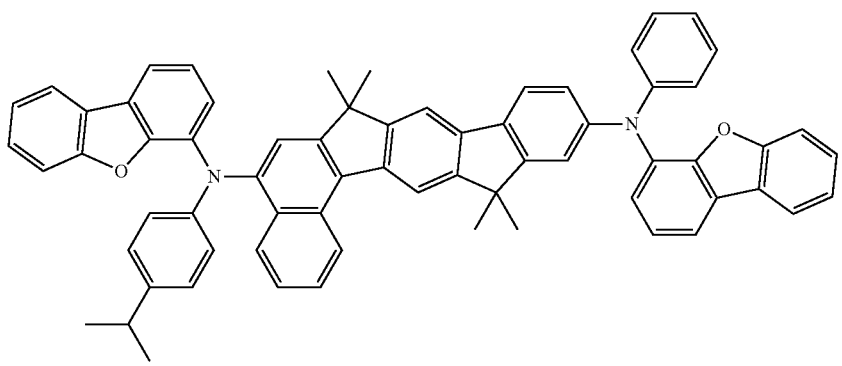
C-2
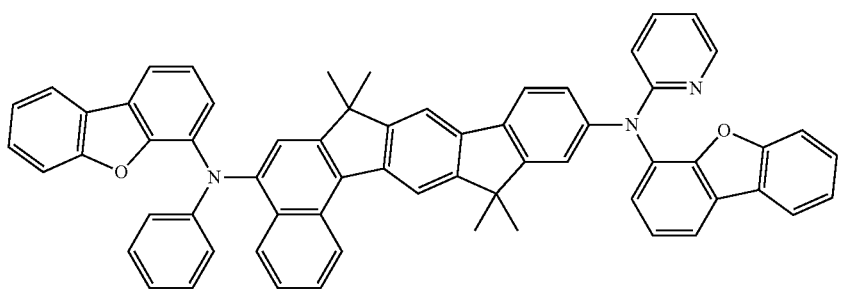
C-3
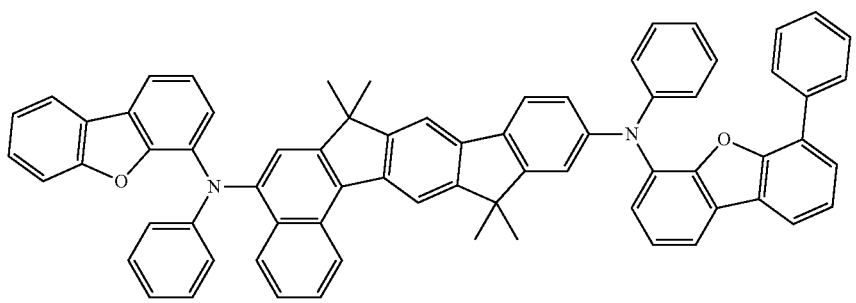
C-4
[Formula 43]
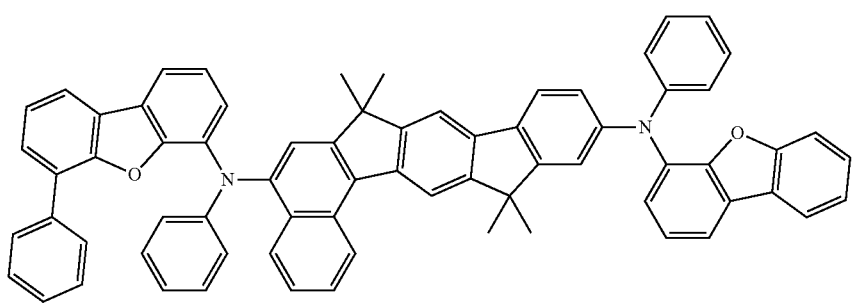
C-5
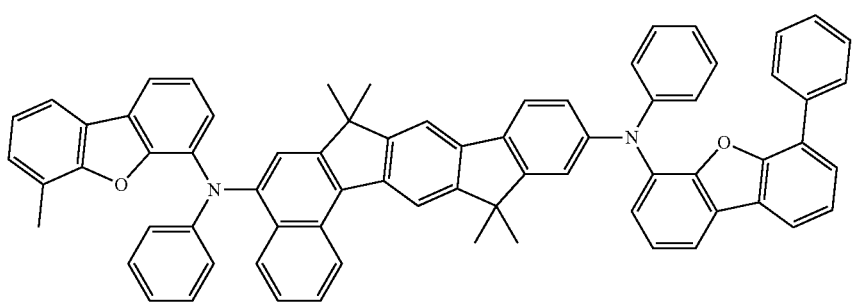
C-6

[Formula 44]
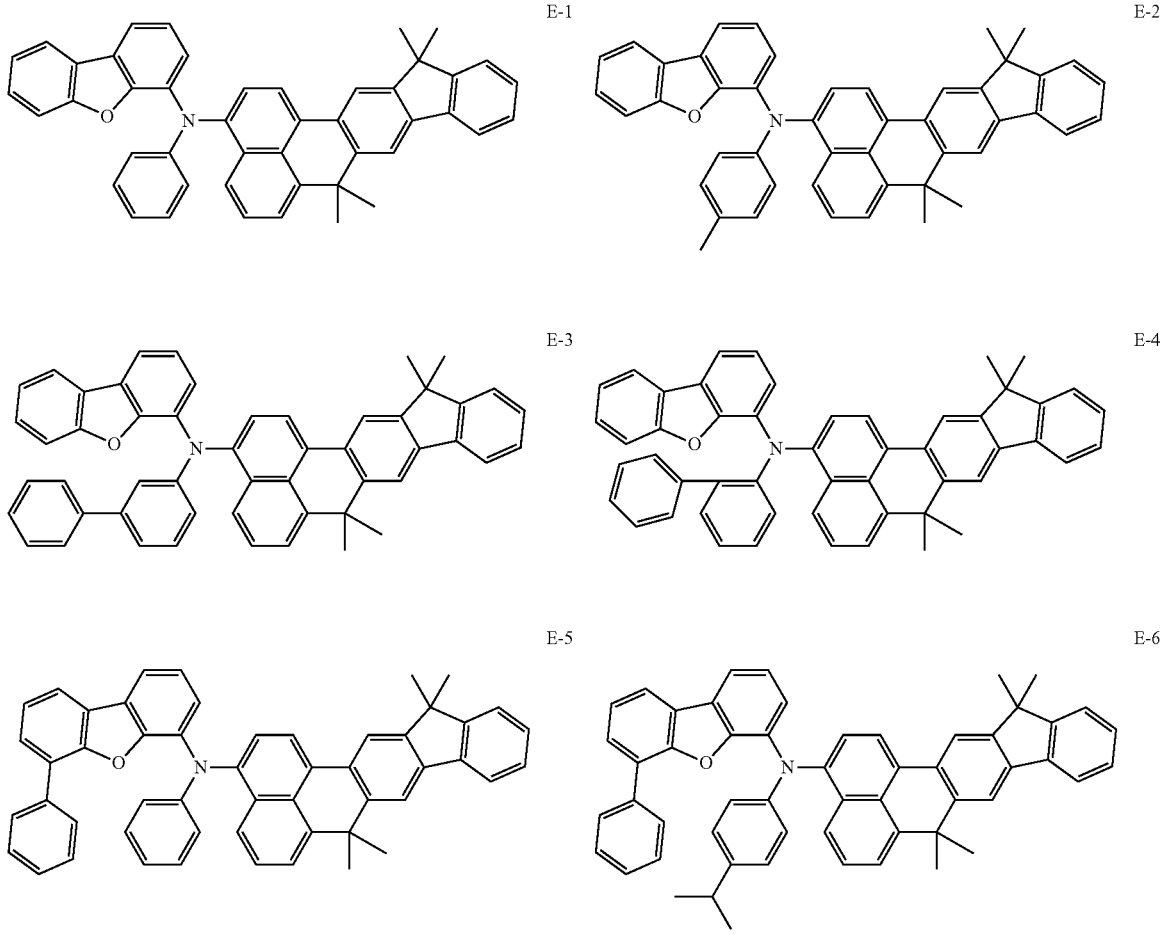
[Formula 45]
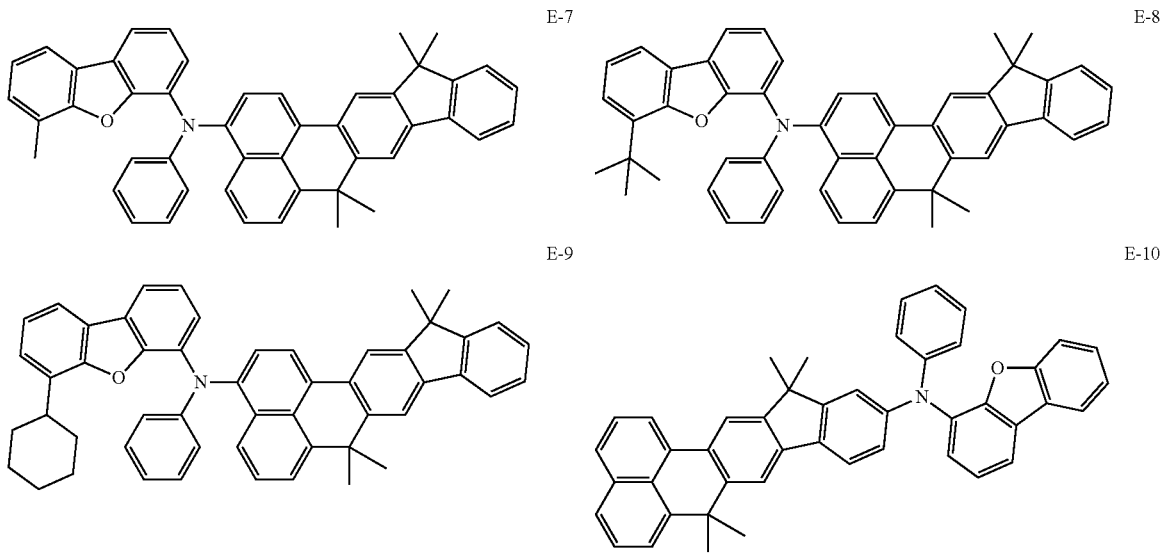

-continued
E-11
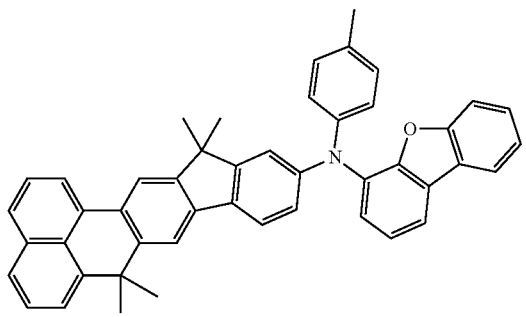
E-12
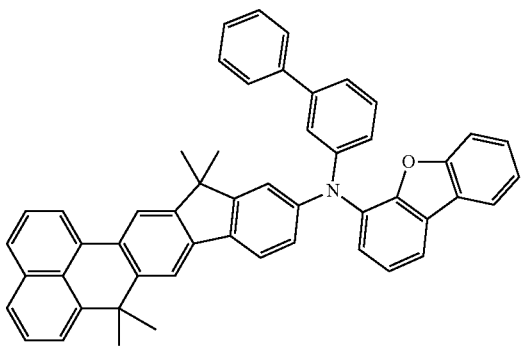
[Formula 46]
E-13
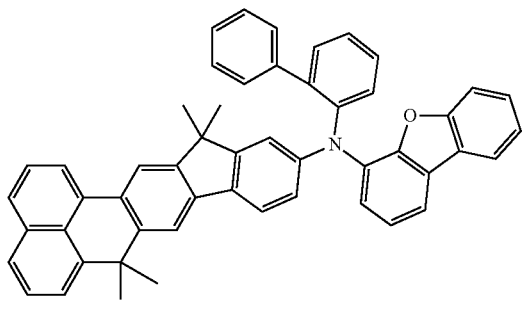
E-14
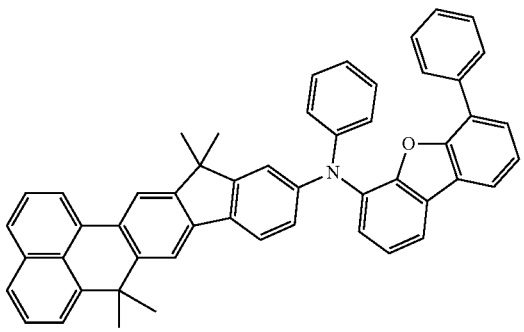
E-15
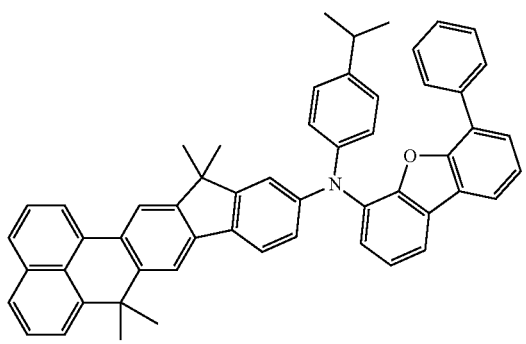
E-16
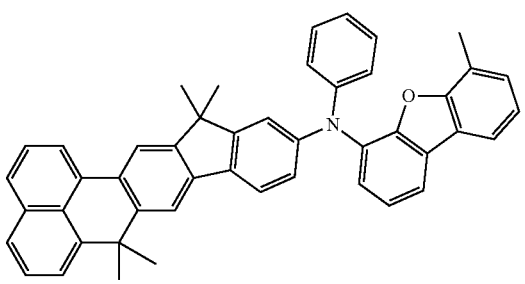
E-17
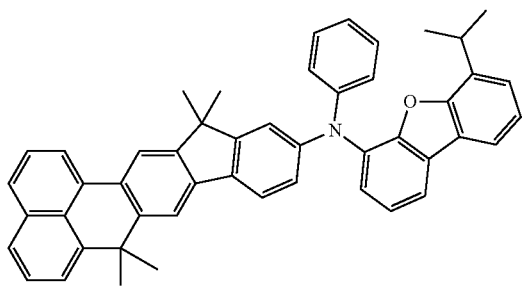
E-18
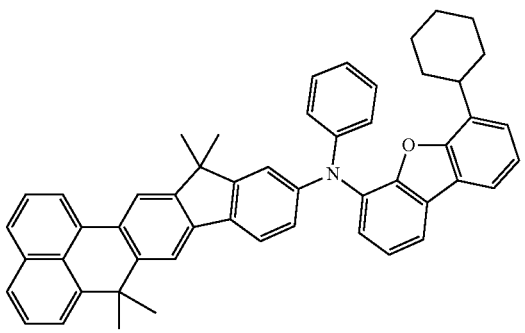

[Formula 47]
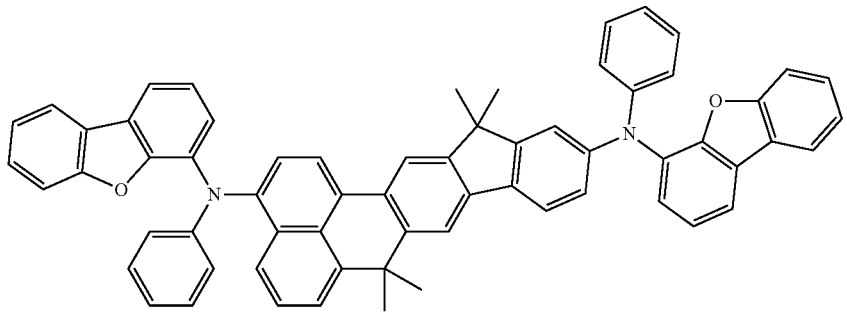
E-19
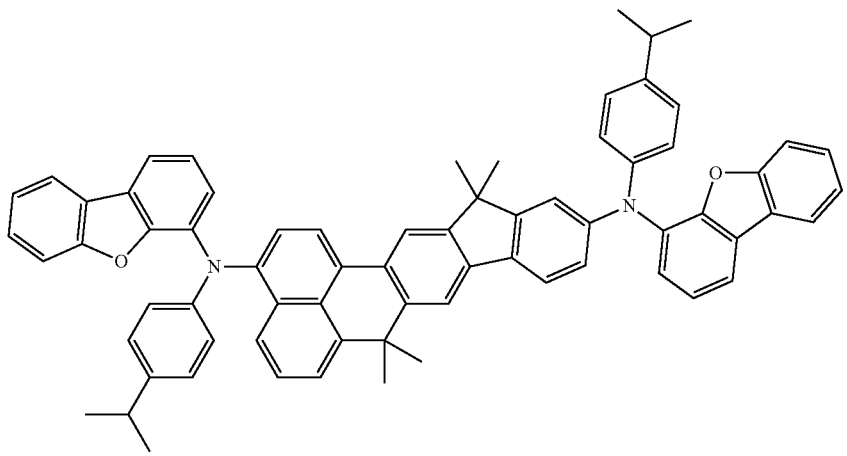
E-20
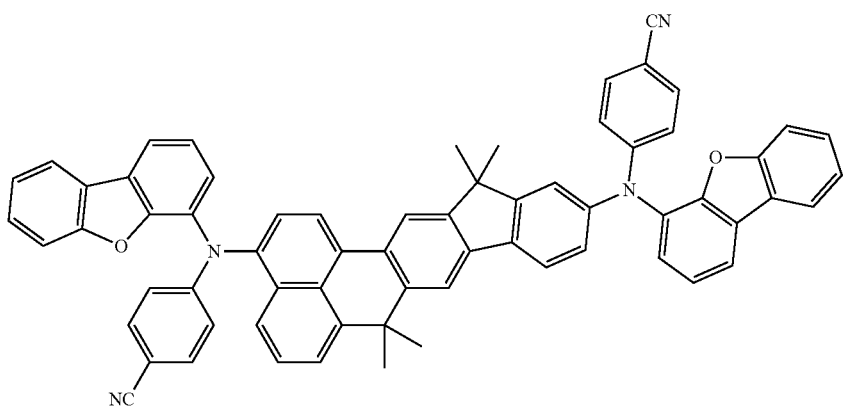
E-21

E-22
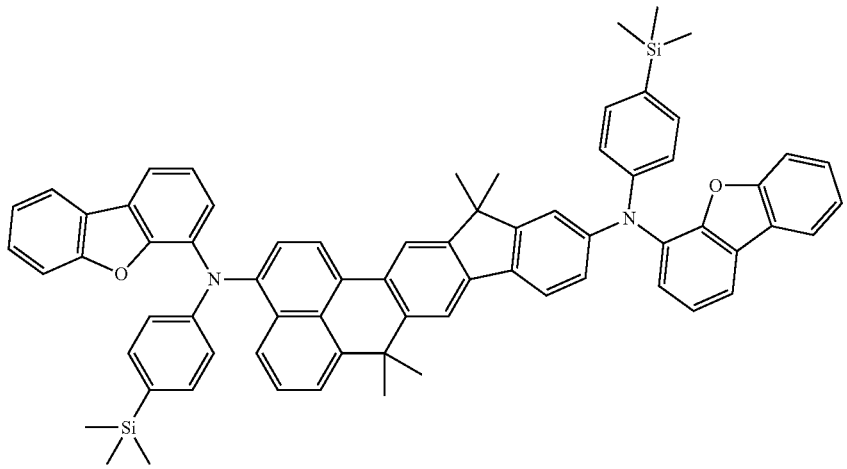
[Formula 48]
E-23
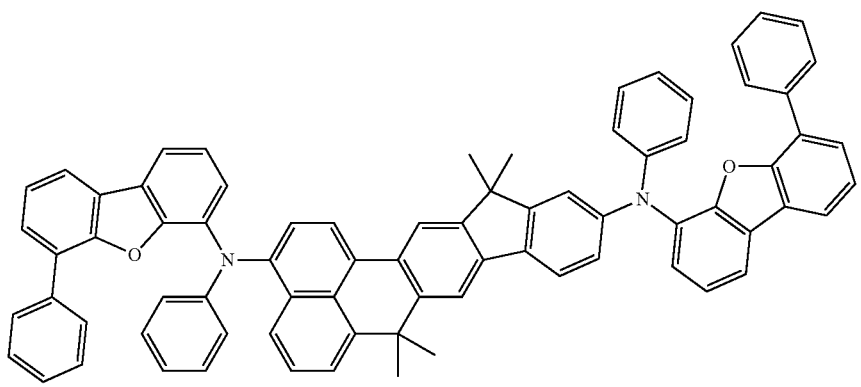
E-24
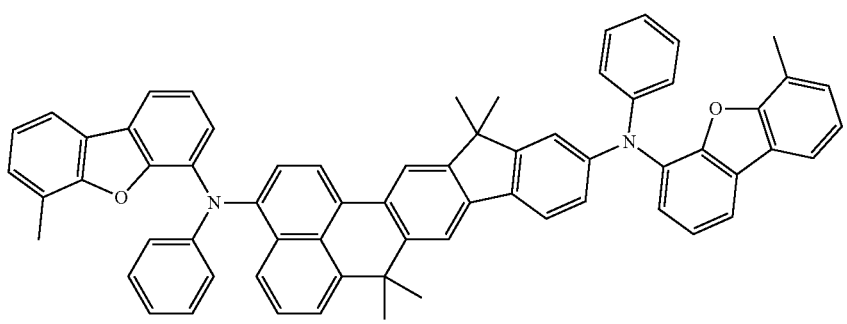
E-25
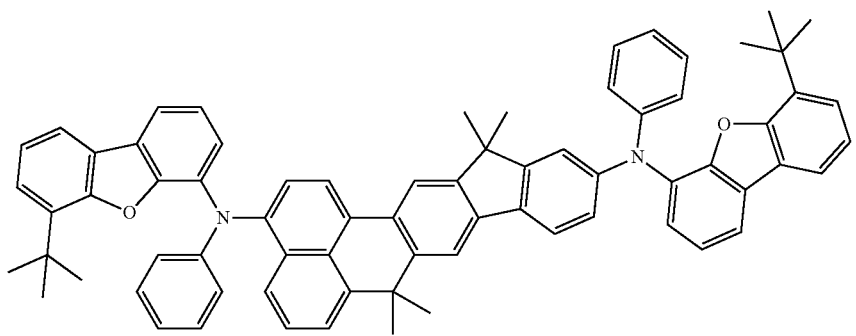

E-26
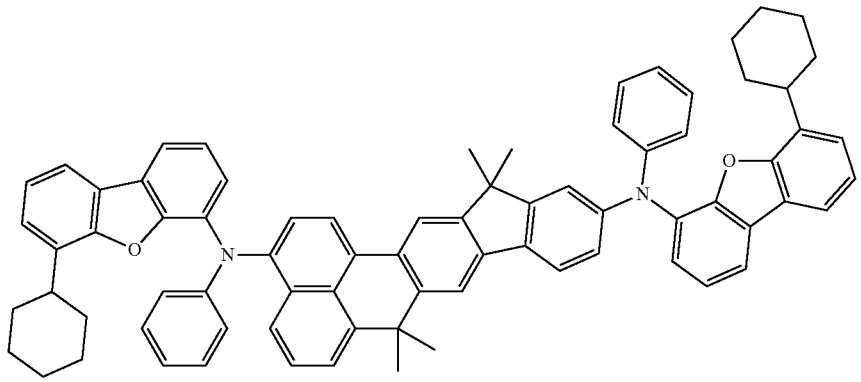
[Formula 49]
E-27
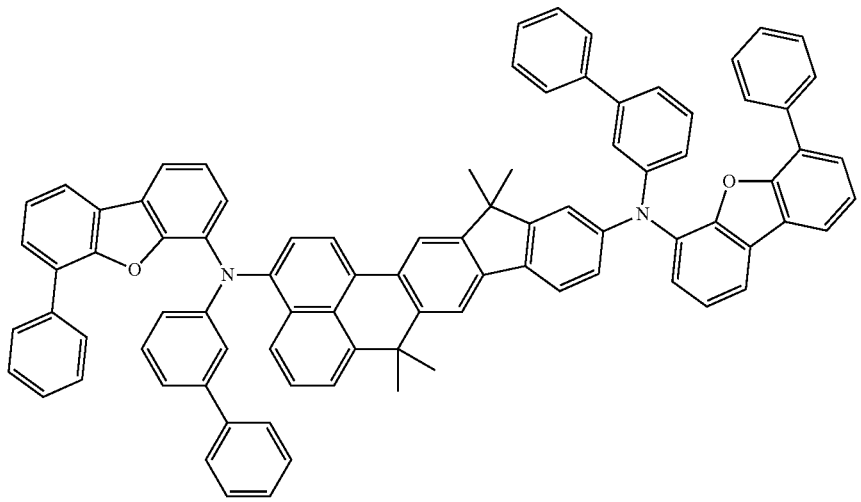
E-28
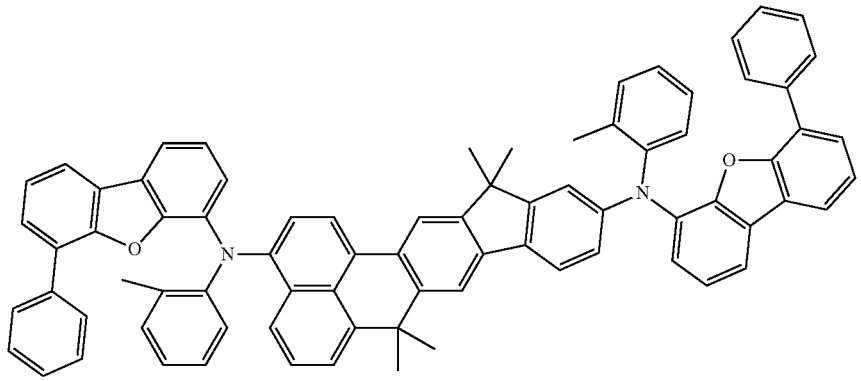

-continued
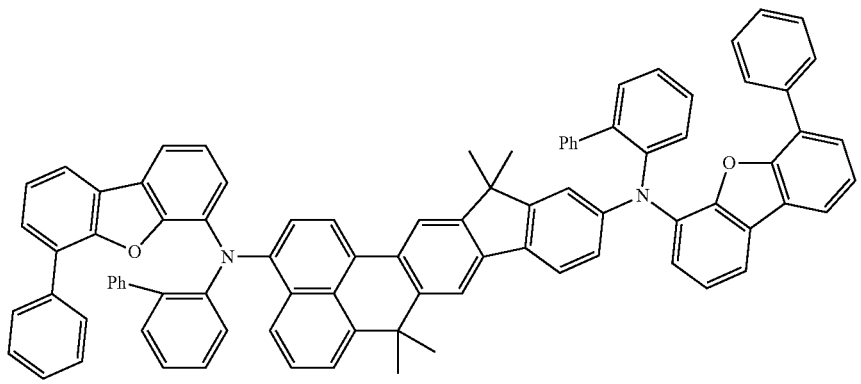
E-29
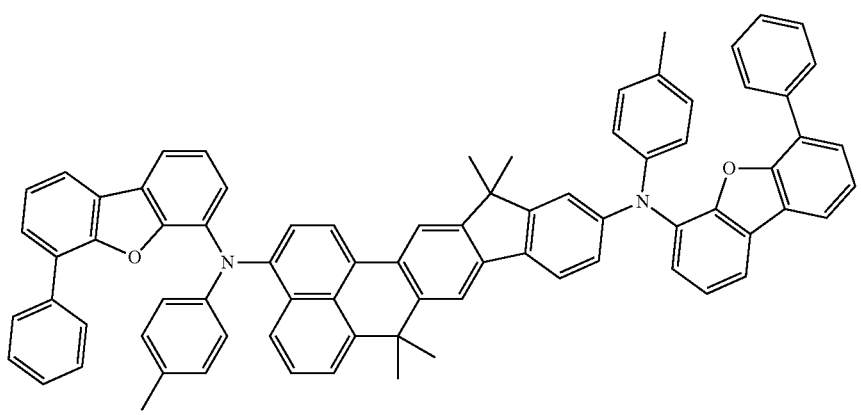
E-30
[Formula 50]
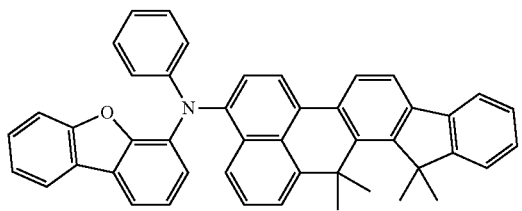
F-1
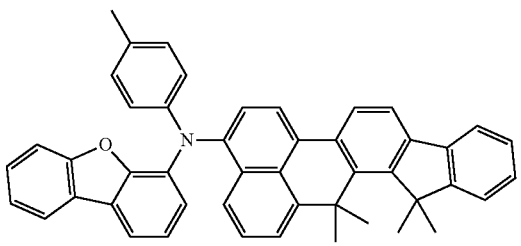
F-2
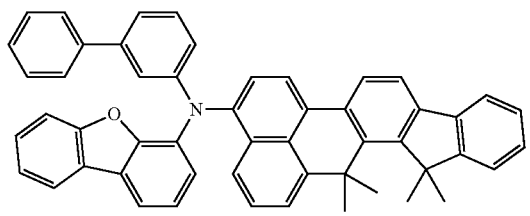
F-3
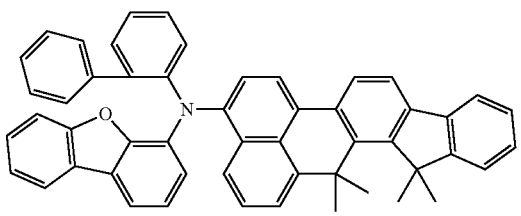
F-4
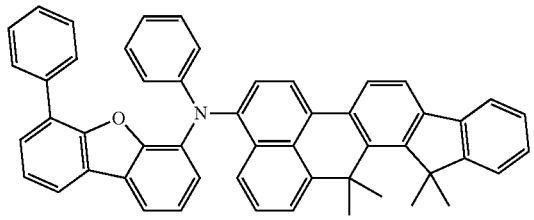
F-5
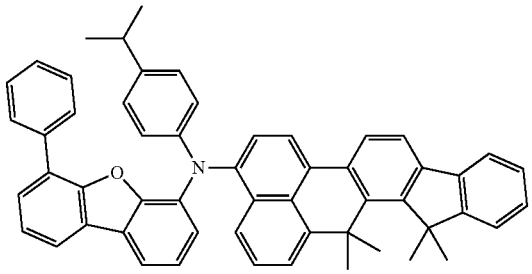
F-6

-continued
[Formula 51]
F-7
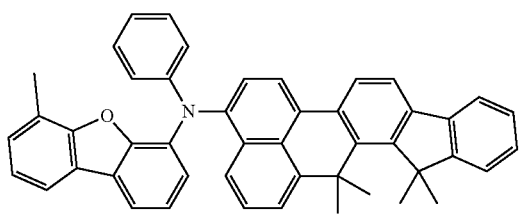
F-8
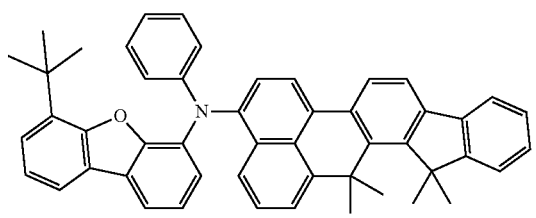
F-9
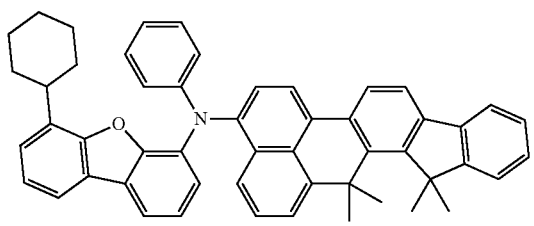
F-10
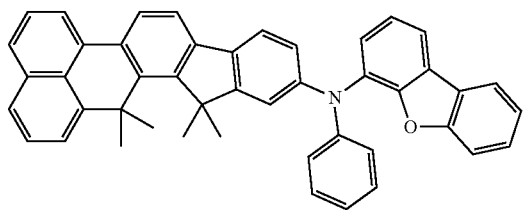
F-11
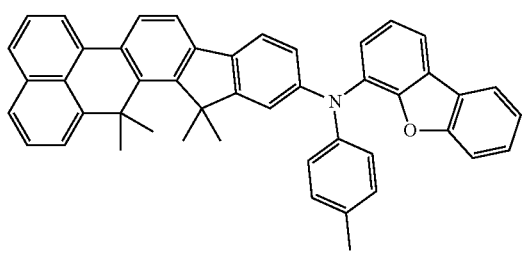
F-12
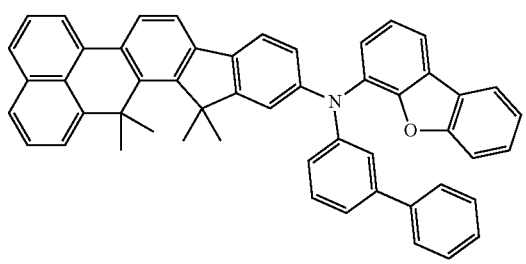
[Formula 52]
F-13
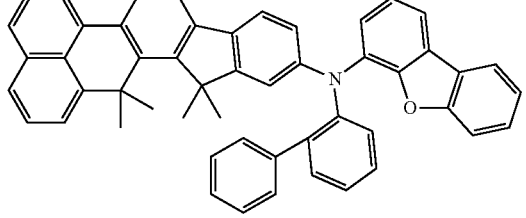
F-14
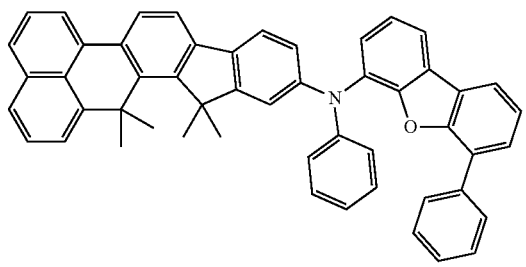
F-15
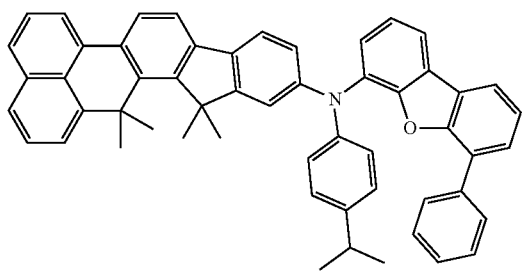
F-16
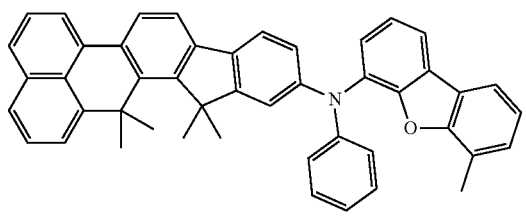

-continued
F-17
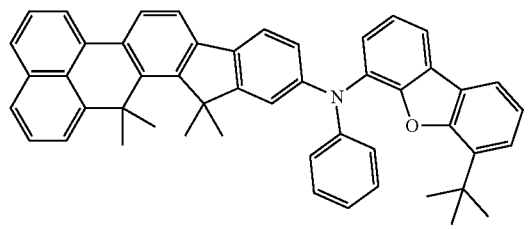
F-18
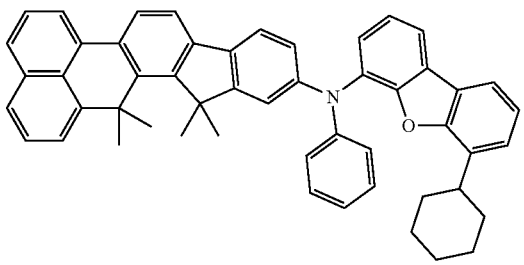
[Formula 53]
F-19
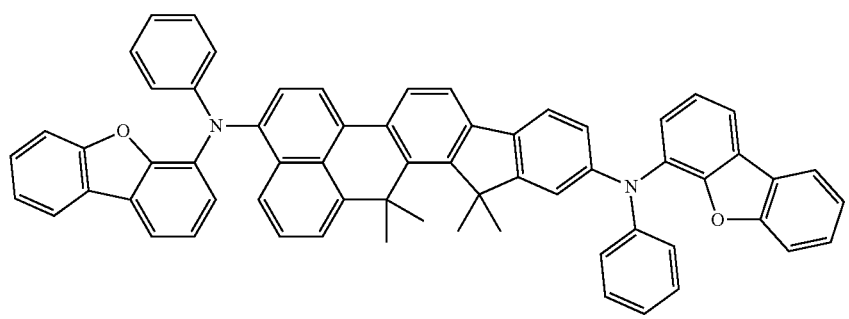
F-20
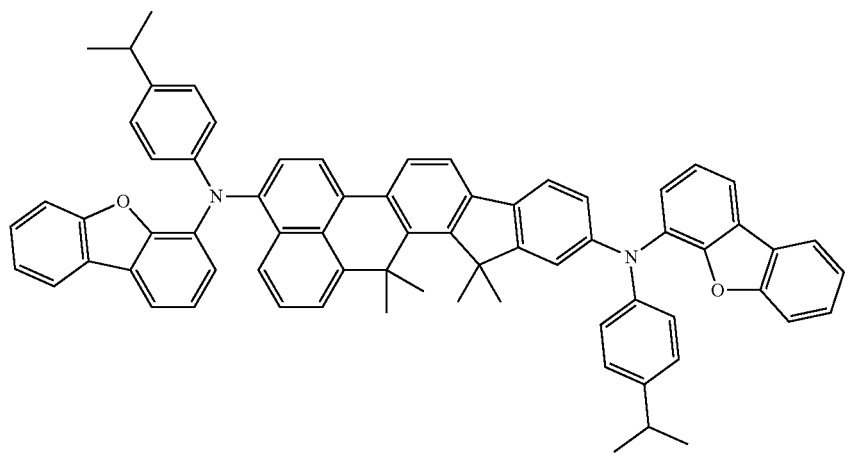
F-21
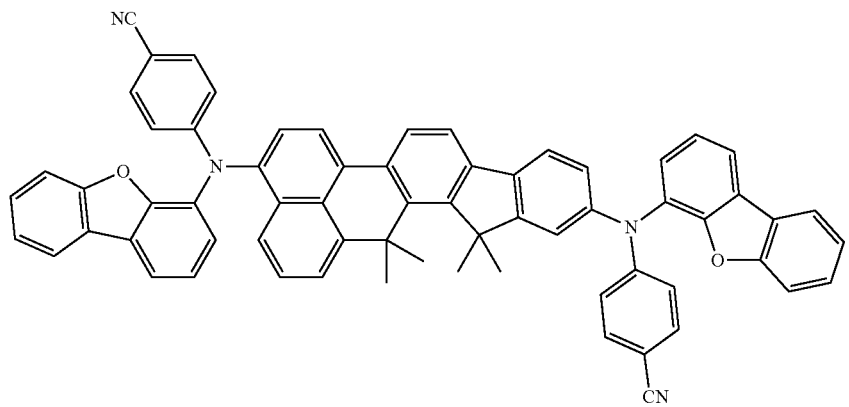

-continued
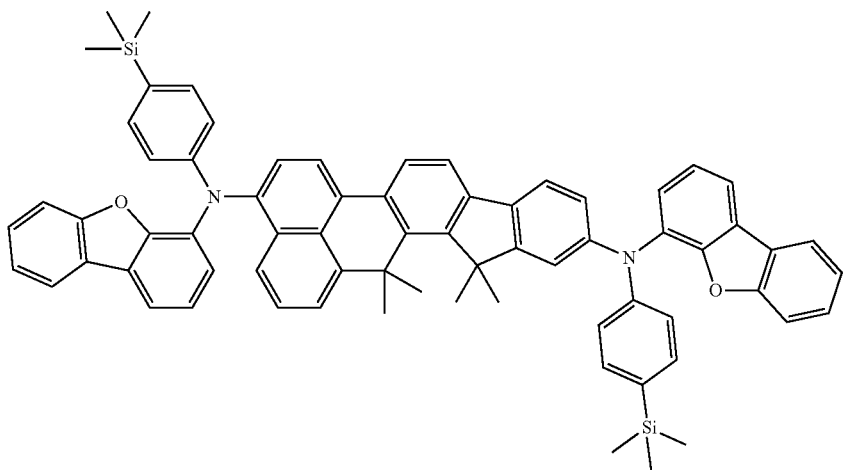
F-22
[Formula 54]
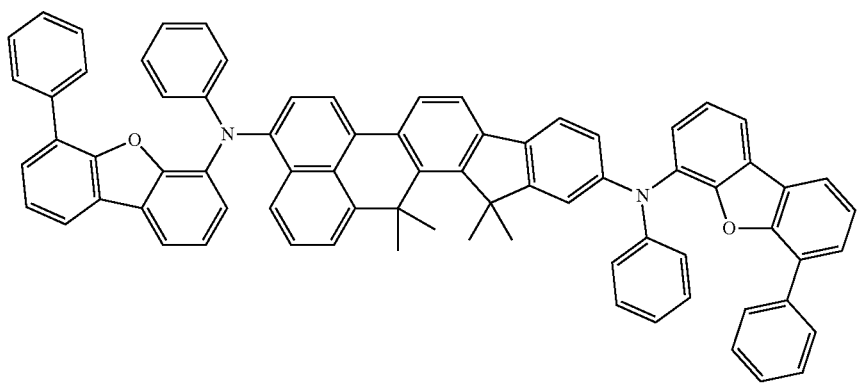
F-23
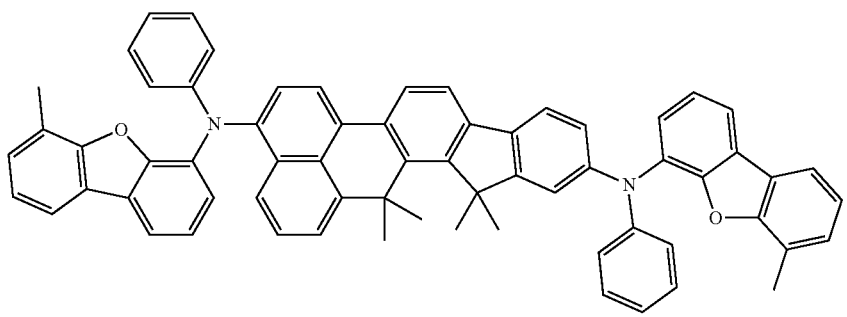
F-24
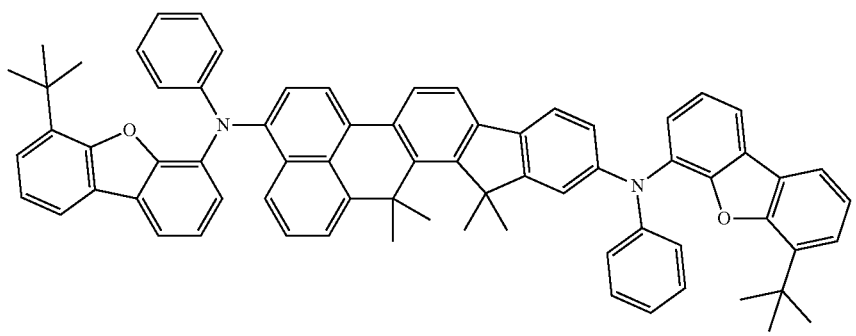
F-25

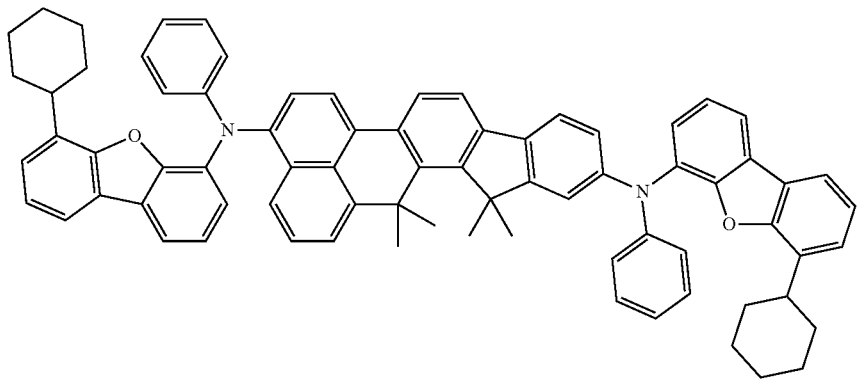
F-26
[Formula 55]
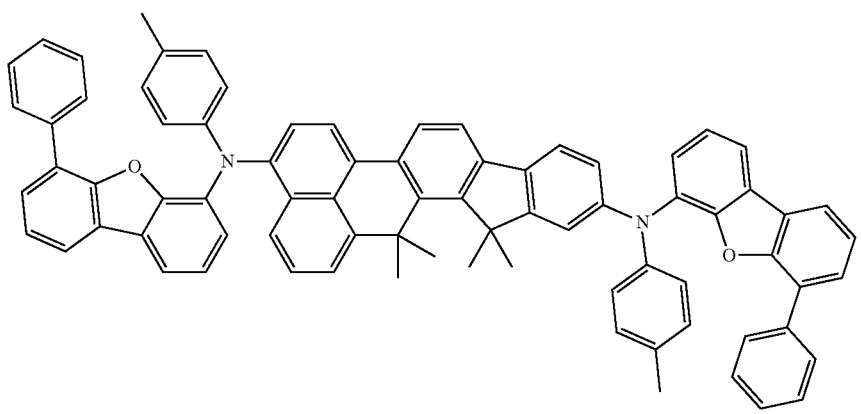
F-27
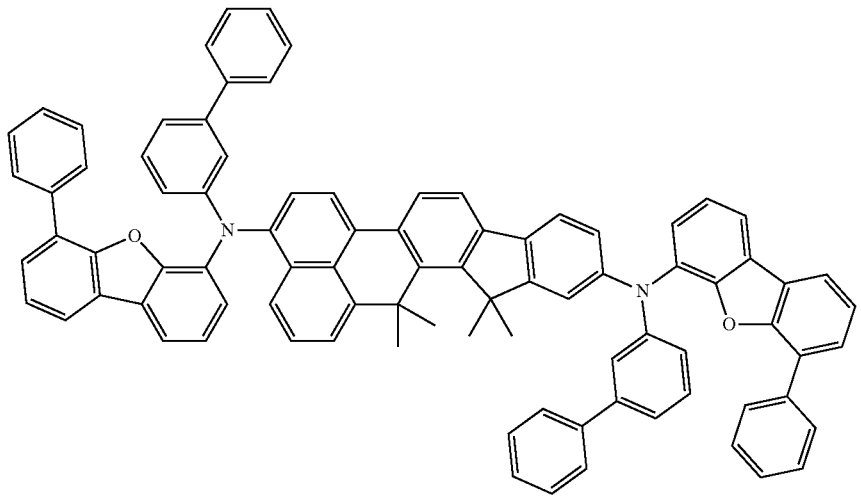
F-28

F-29
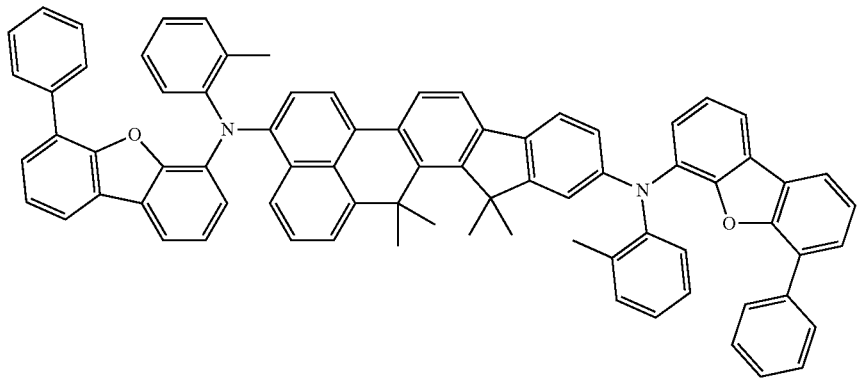
F-30
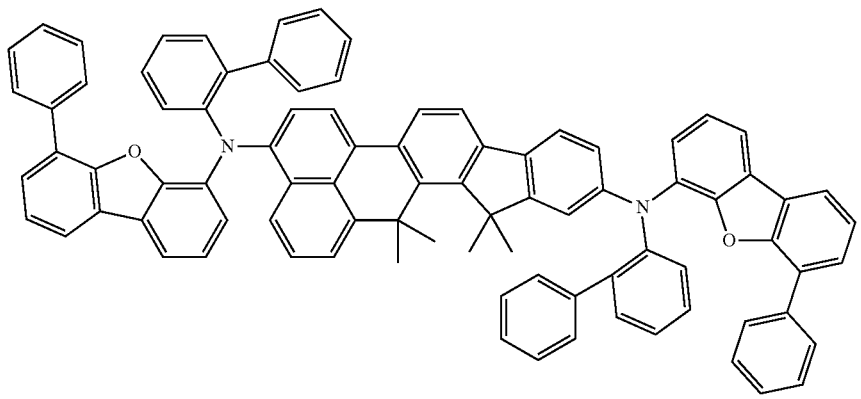
[Formula 56]
G-1
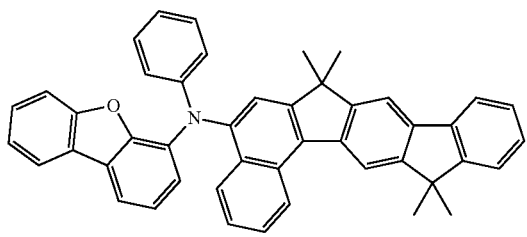
G-2
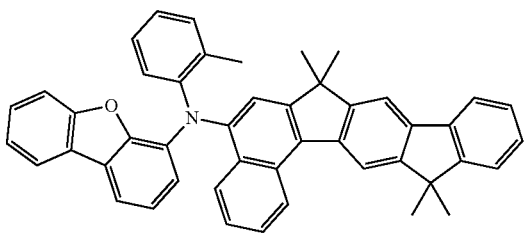
G-3
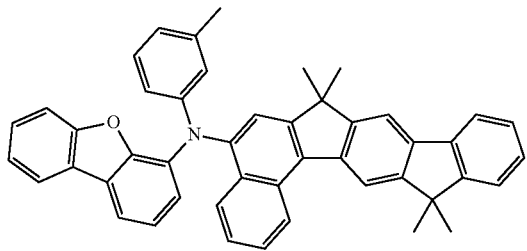
G-4
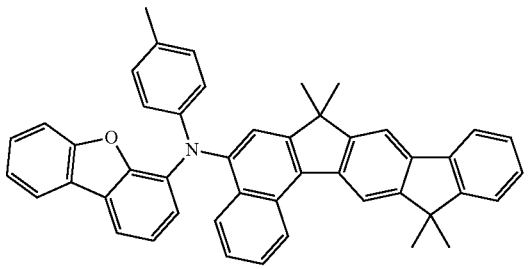

G-5
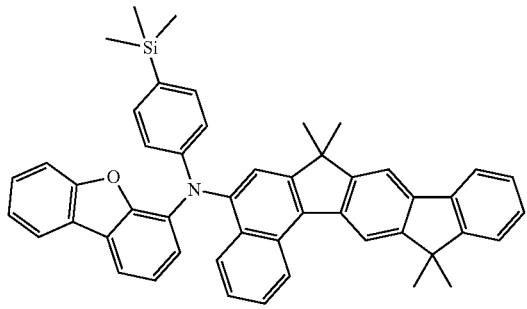
G-6
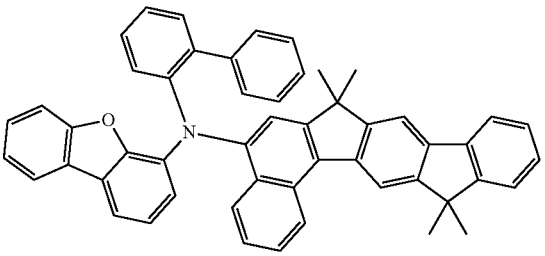
G-7
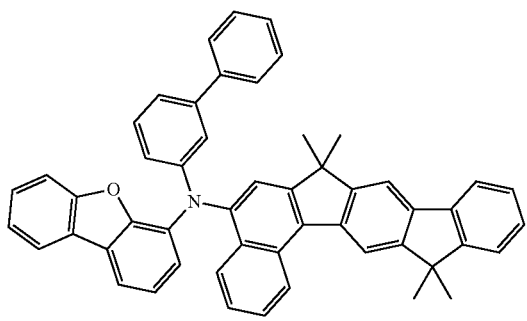
G-8
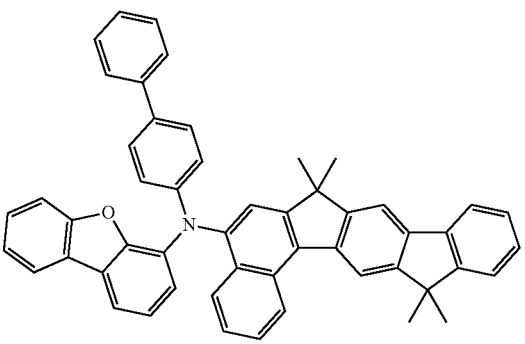
G-9
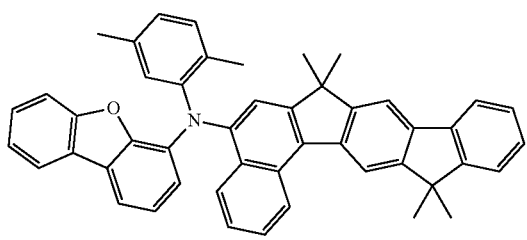
G-10
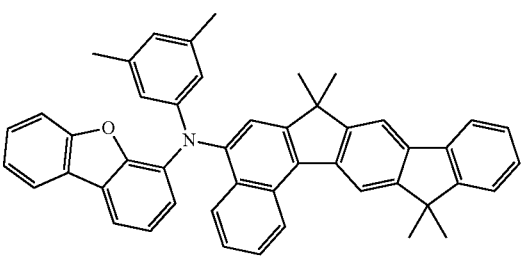
G-11
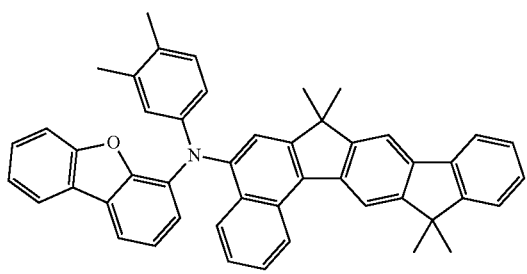
G-12
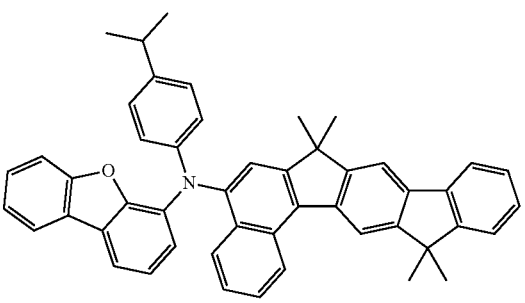

[Formula 57]
[Formula 58]
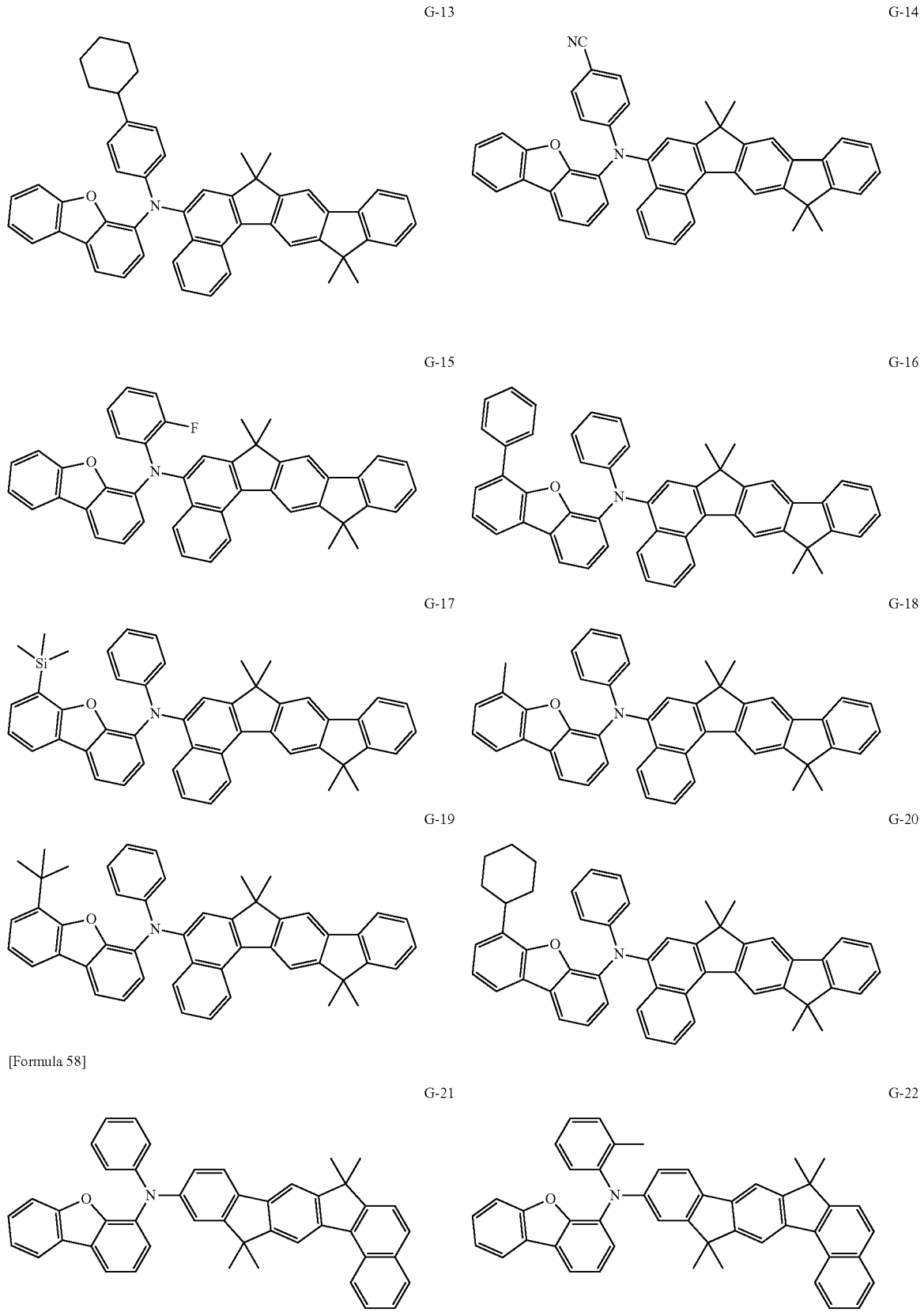

-continued
G-23
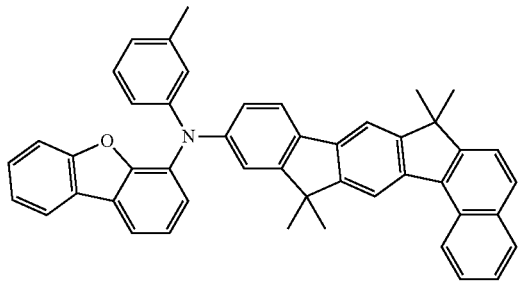
G-24
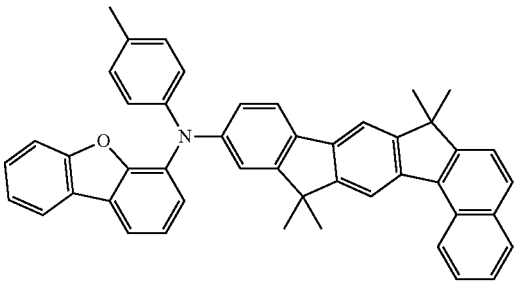
G-25
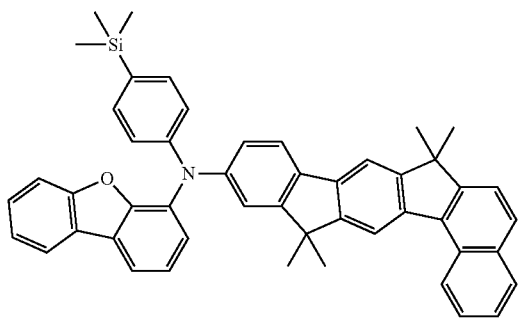
G-26
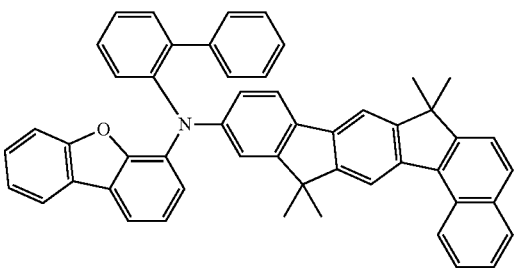
G-27
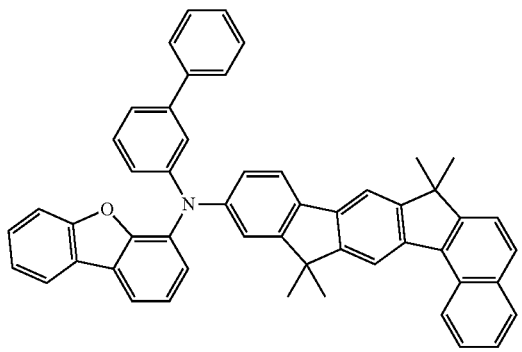
G-28
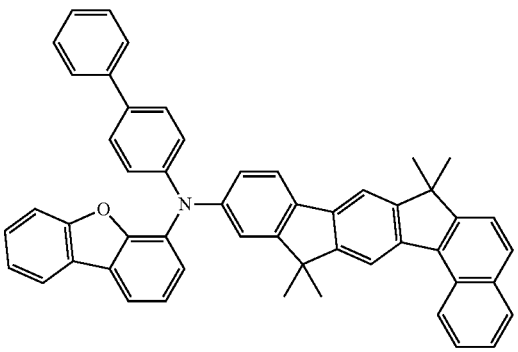
G-29
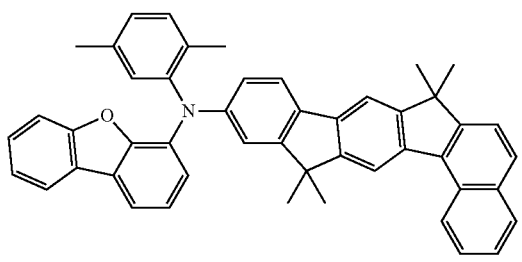
G-30
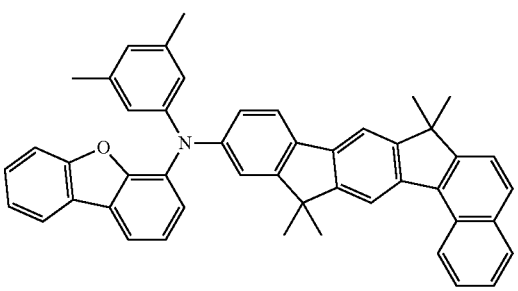

-continued
G-31
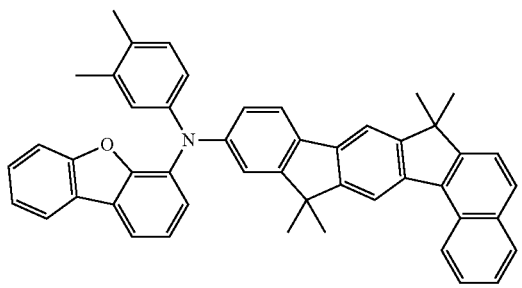
G-32
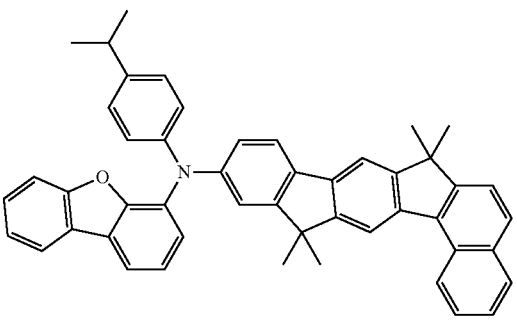
[Formula 59]
G-33
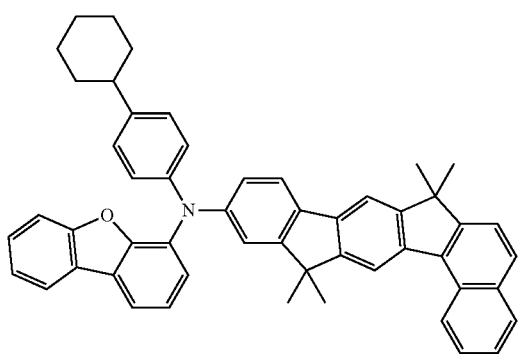
G-34
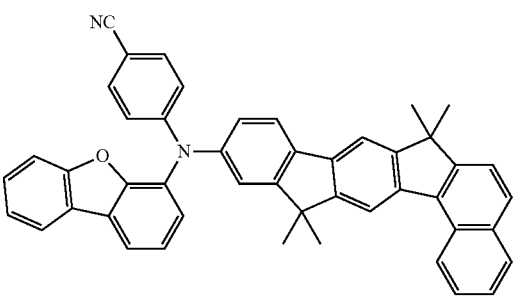
G-35
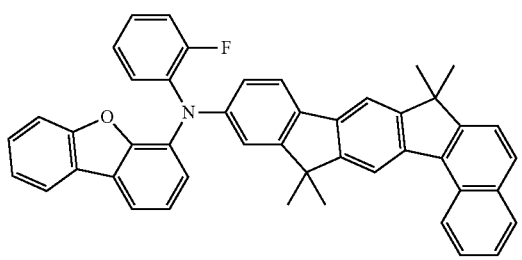
G-36
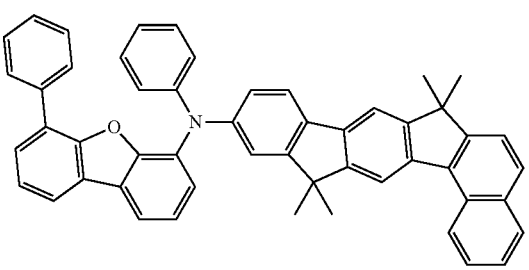
G-37
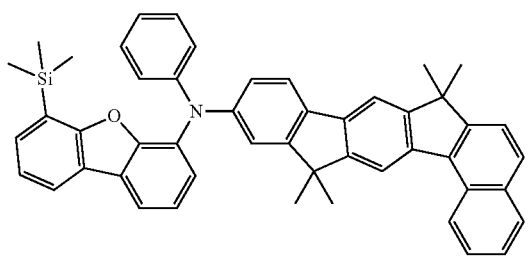
G-38
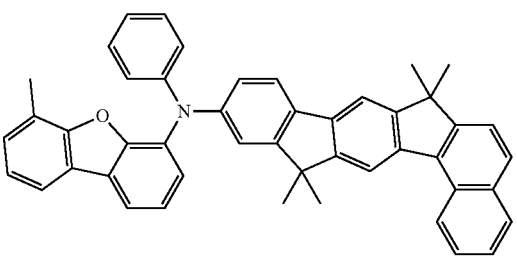
G-39
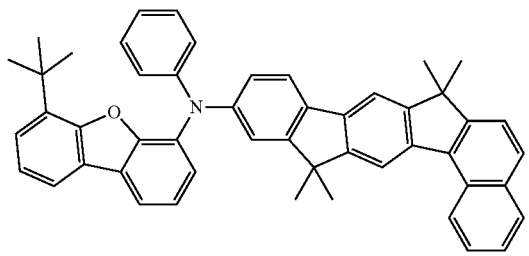
G-40
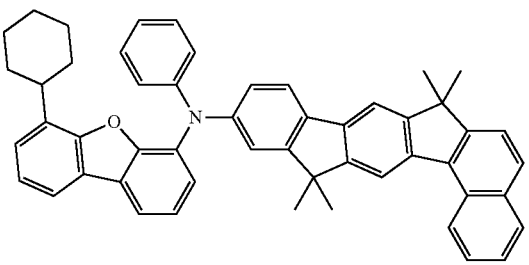

[Formula 60]
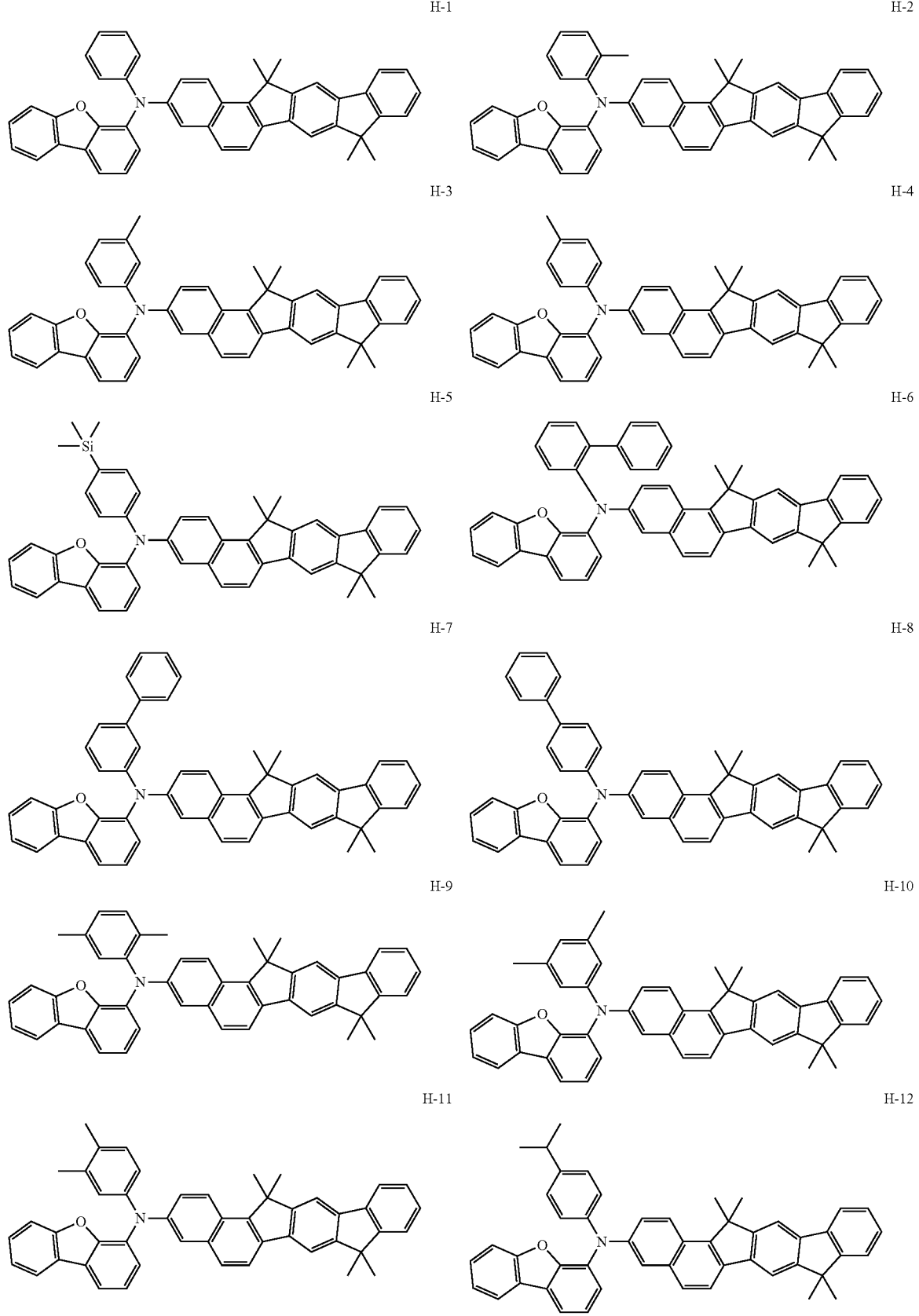

-continued
[Formula 61]
H-13
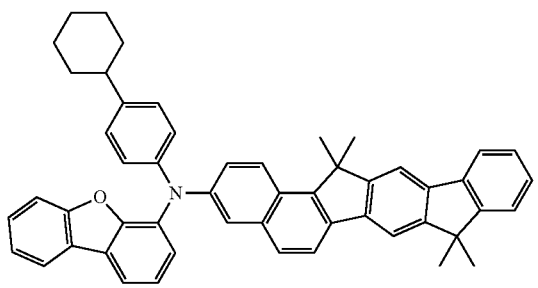
H-14
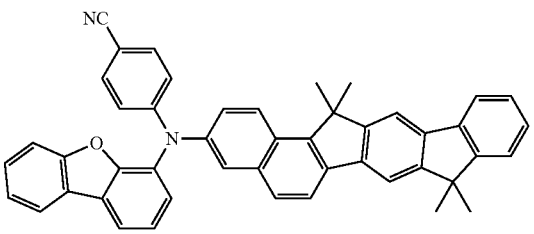
H-15
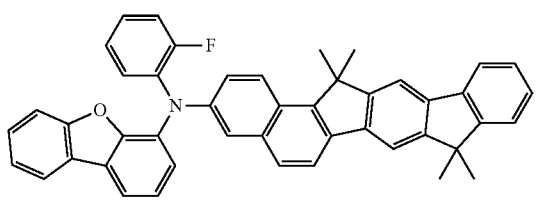
H-16
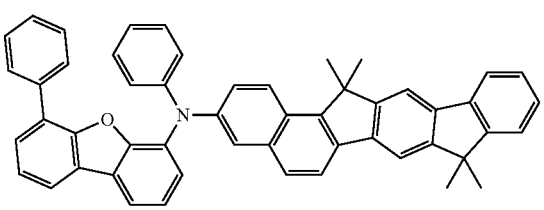
H-17
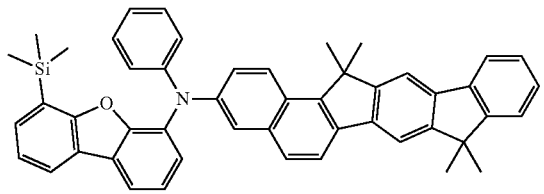
H-18
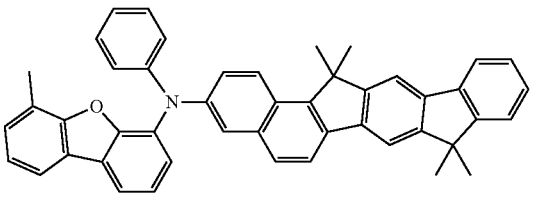
H-19
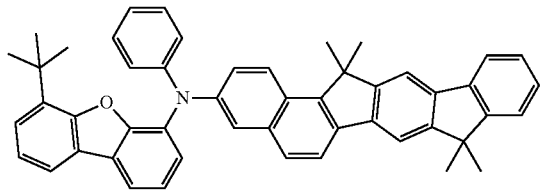
H-20
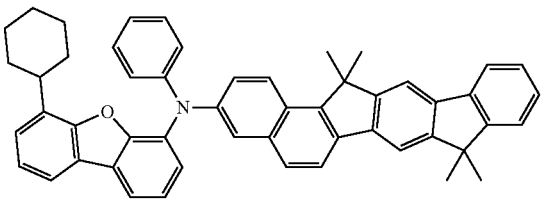

[Formula 62]
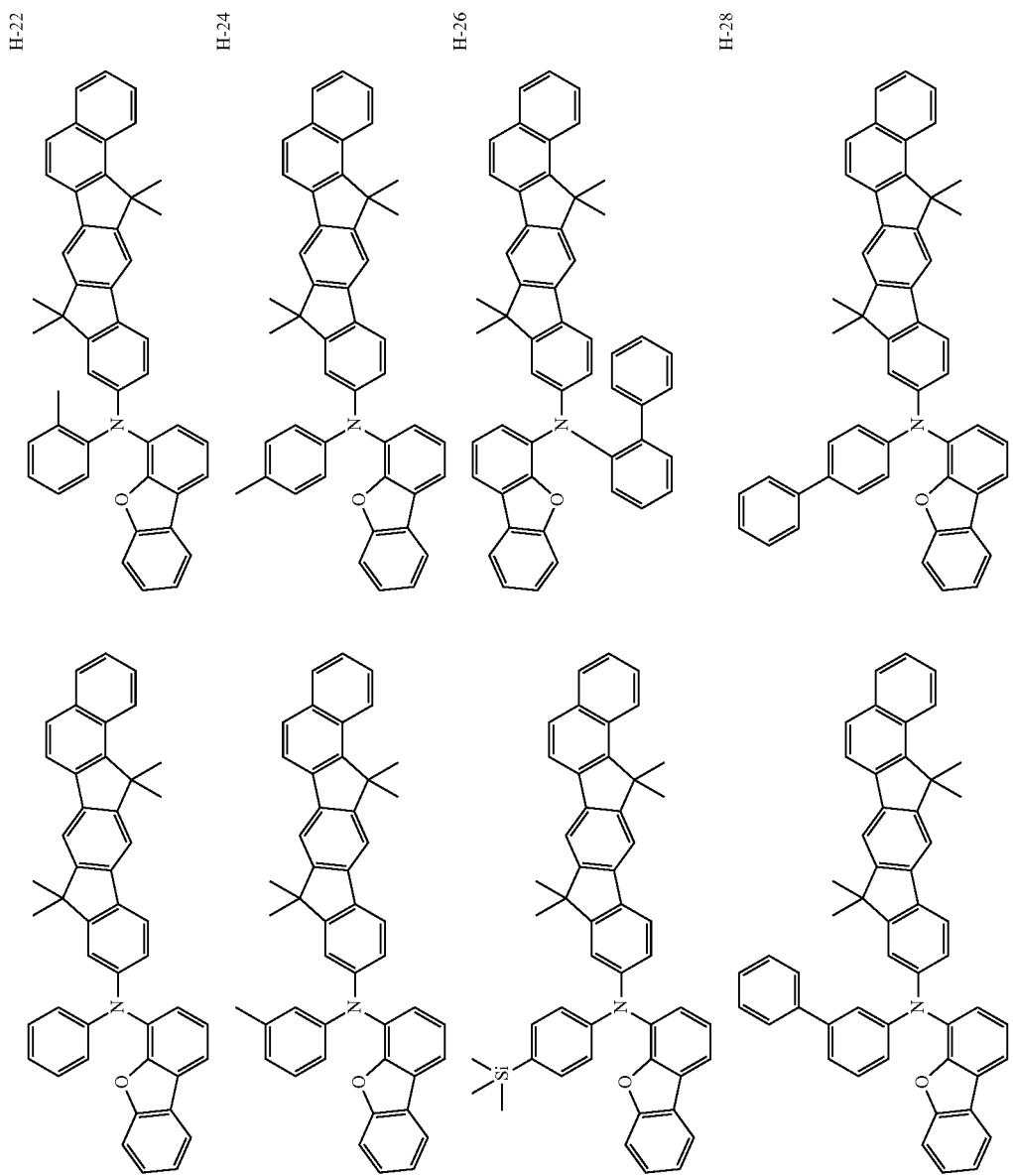

-continued
H-29
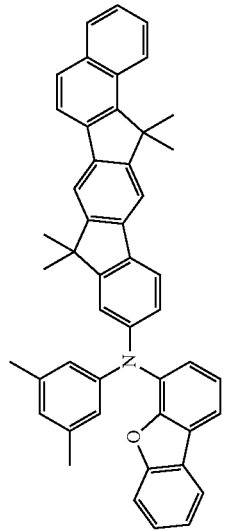
H-30
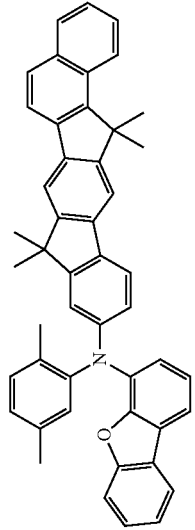
H-31
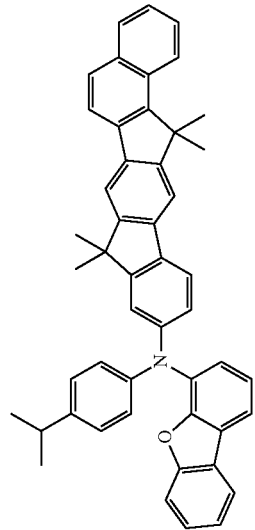
H-32
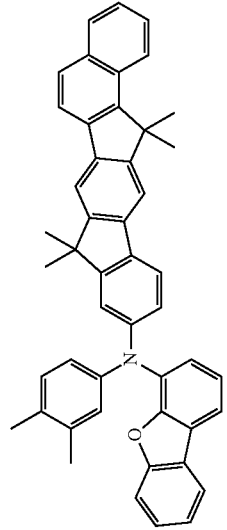
H-33
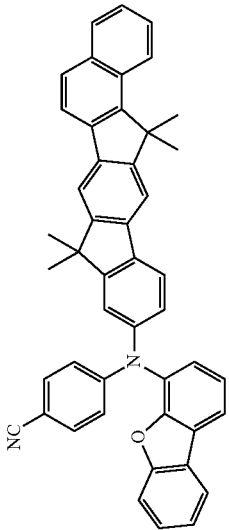
H-34
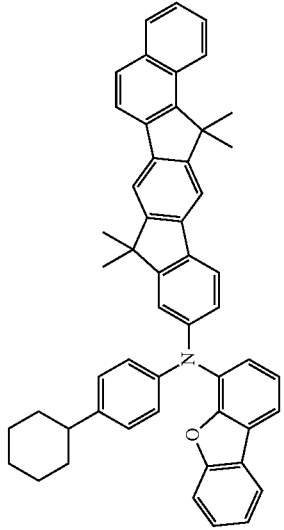
H-35
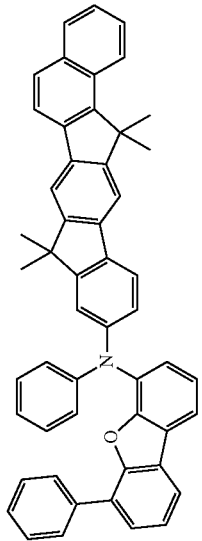
H-36
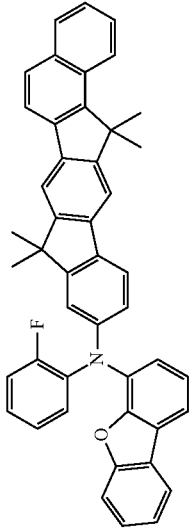
[Formula 63]

-continued
H-37 H-38
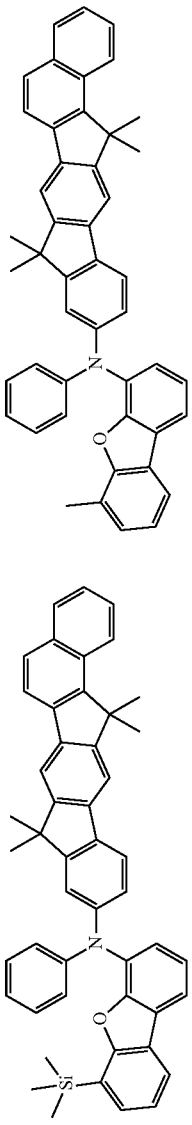
H-39 H-40
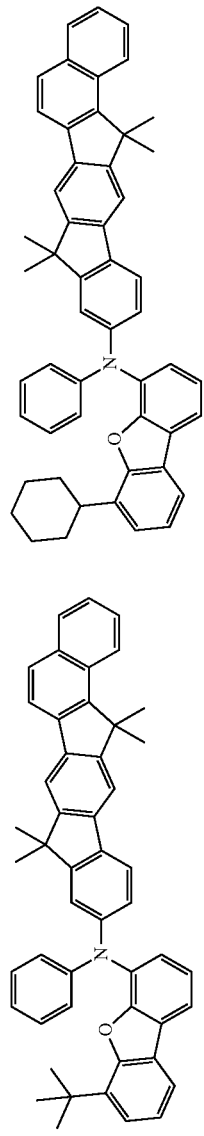
[Formula 64]
I-1 I-2
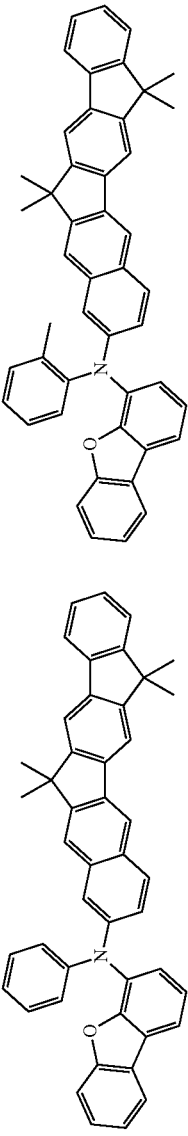
I-3 I-4
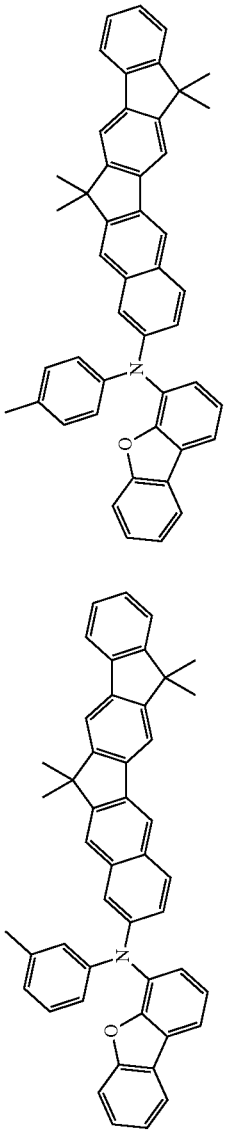

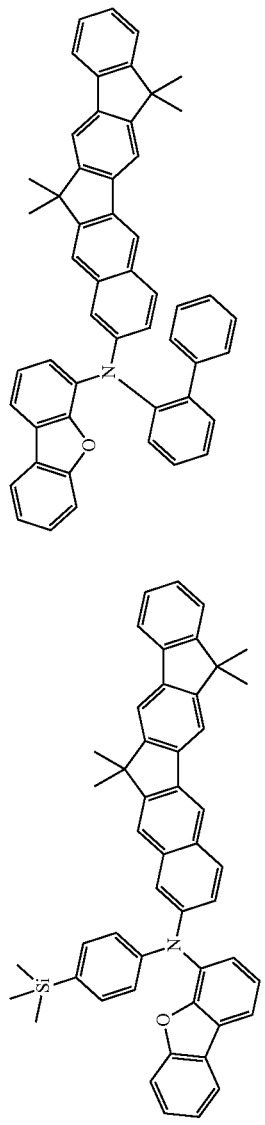

-continued
I-11 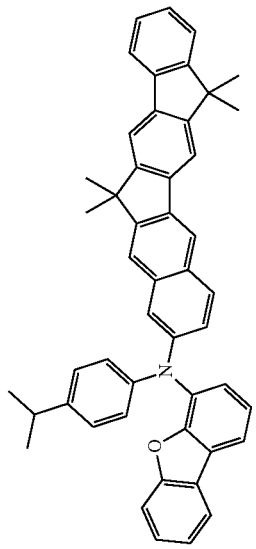
I-12 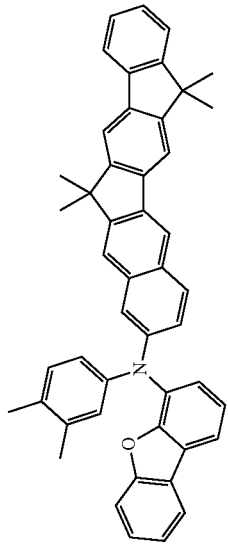
I-13 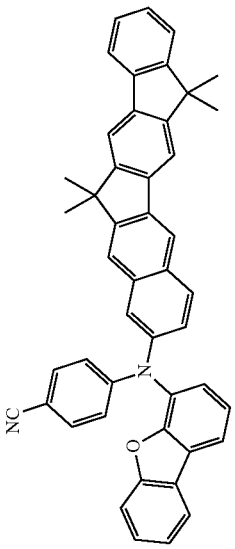
I-14 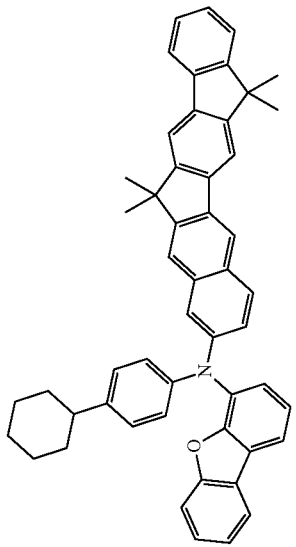
I-15 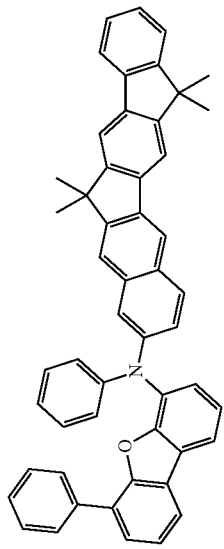
I-16 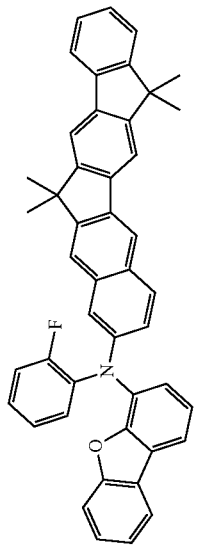
I-17 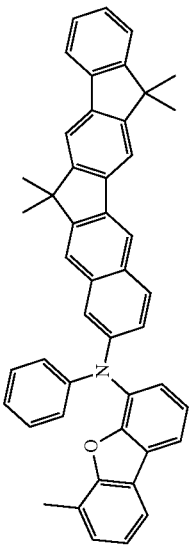
I-18 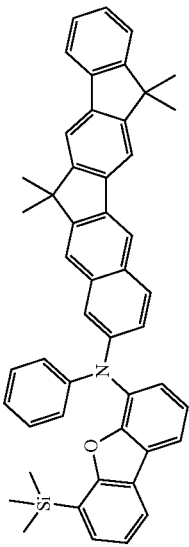
[Formula 65]

-continued
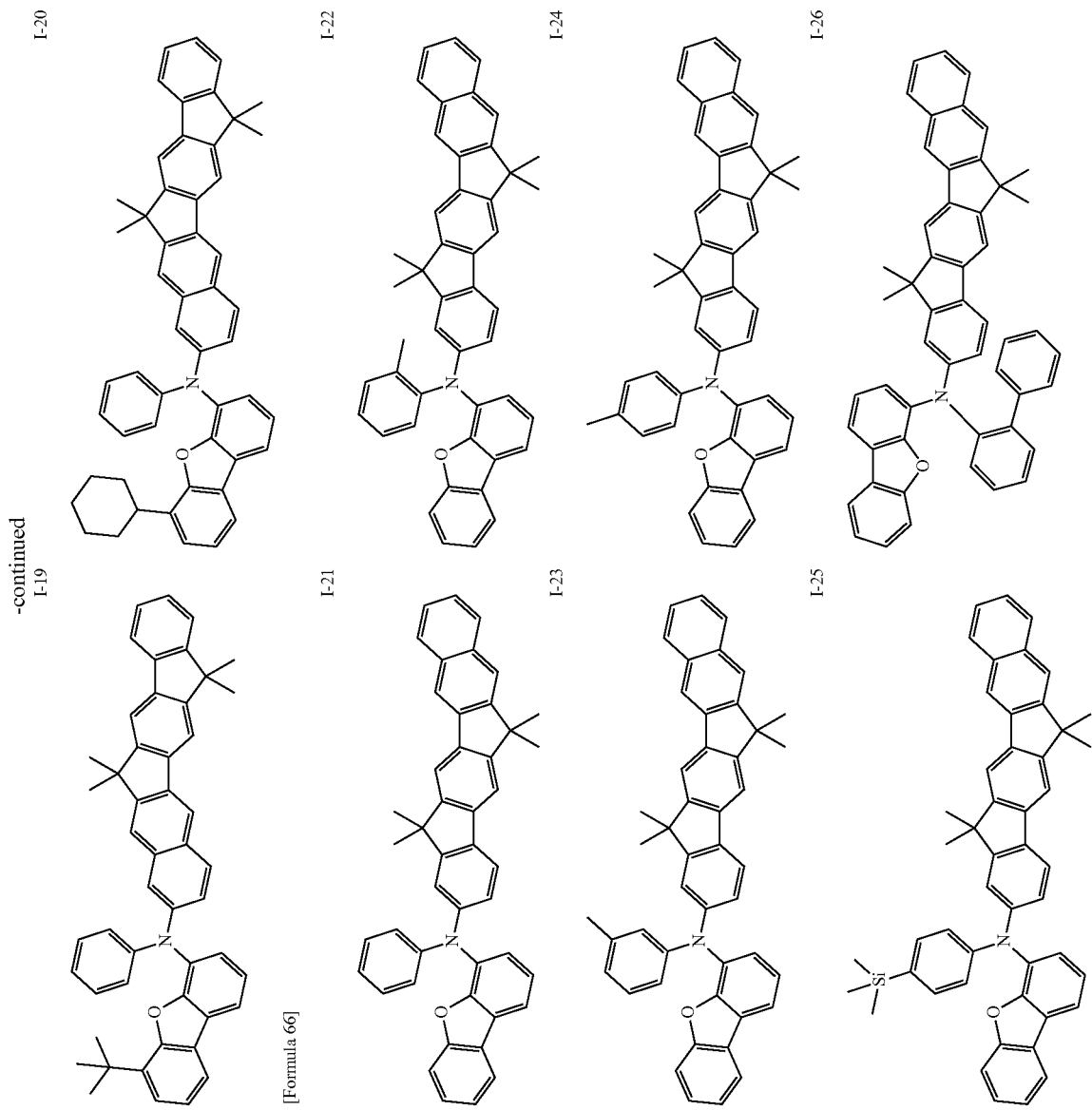

-continued
I-27
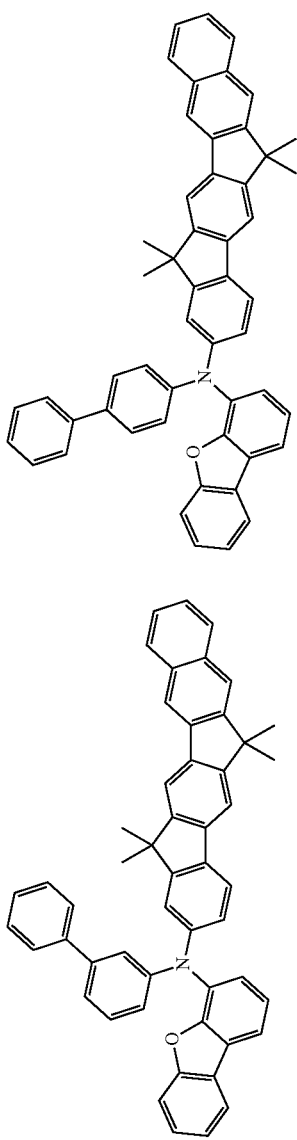
I-28
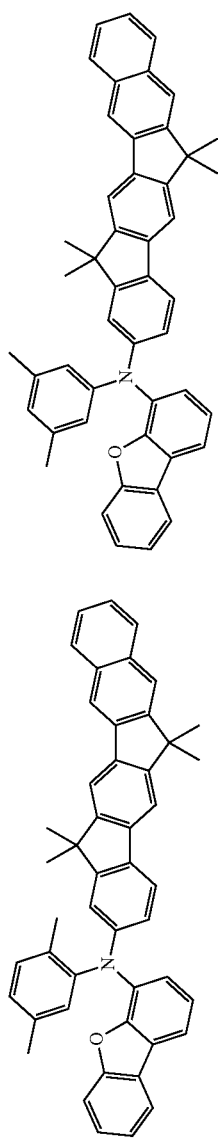
I-29
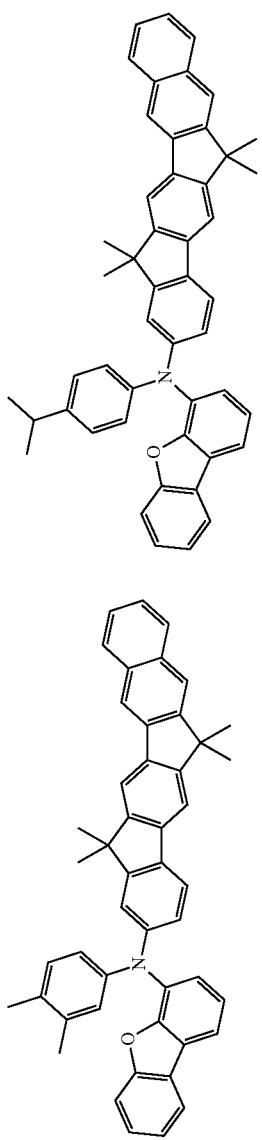
I-30
I-31
I-32

-continued
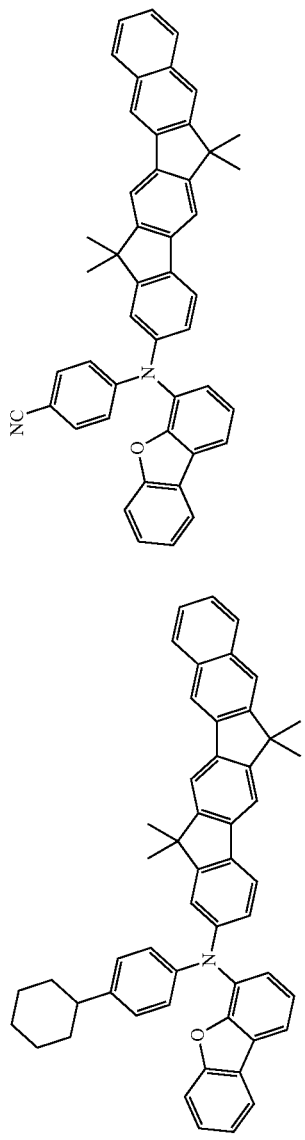
I-33
I-34
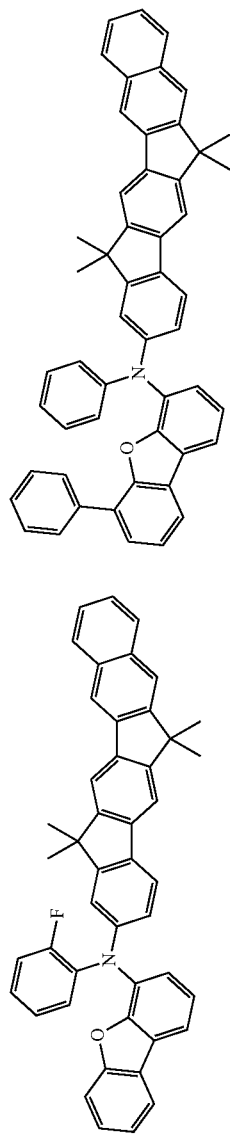
I-35
I-36
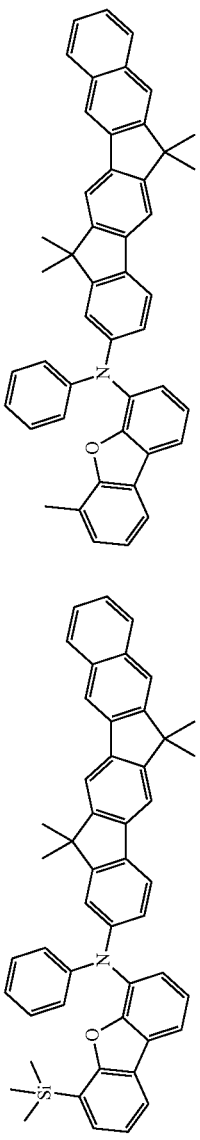
I-37
I-38
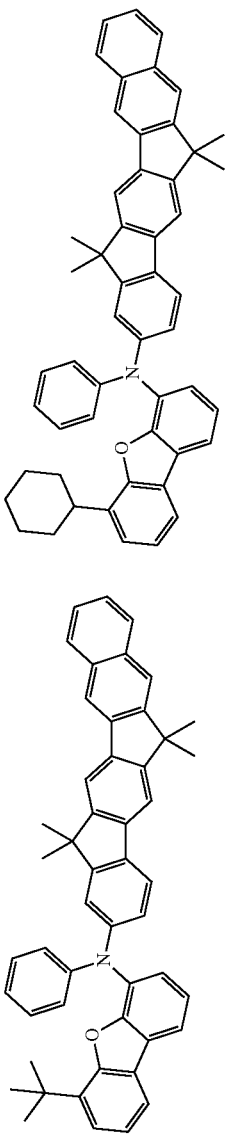
I-39
I-40
[Formula 67]

[Formula 68]
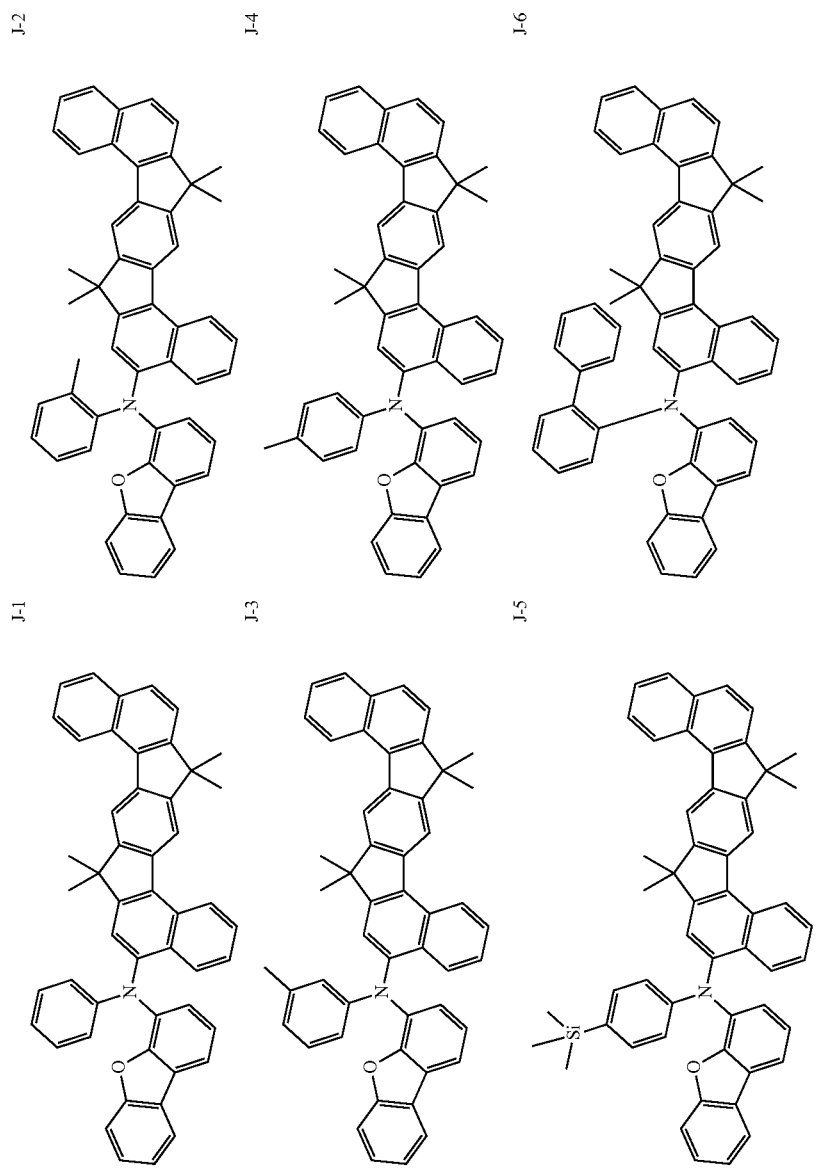

-continued
J-7
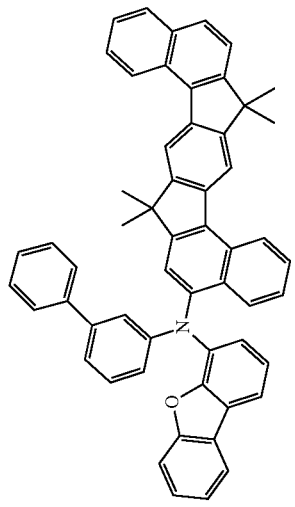
J-8
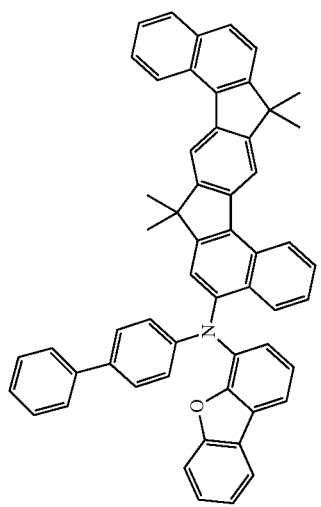
J-9
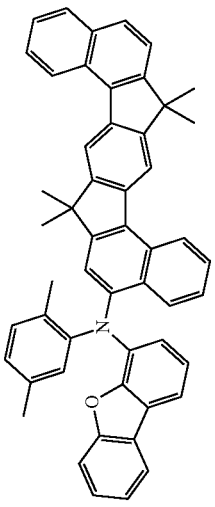
J-10
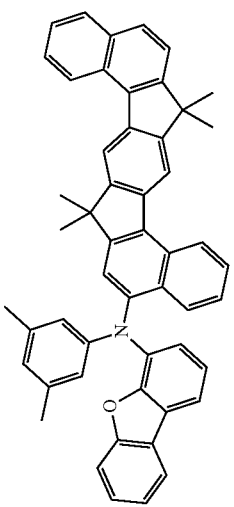
J-11
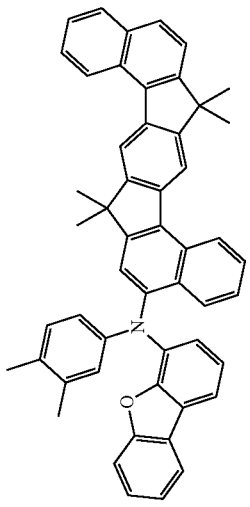
J-12
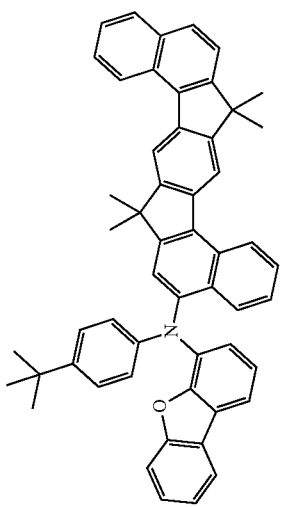

-continued
[Formula 69]
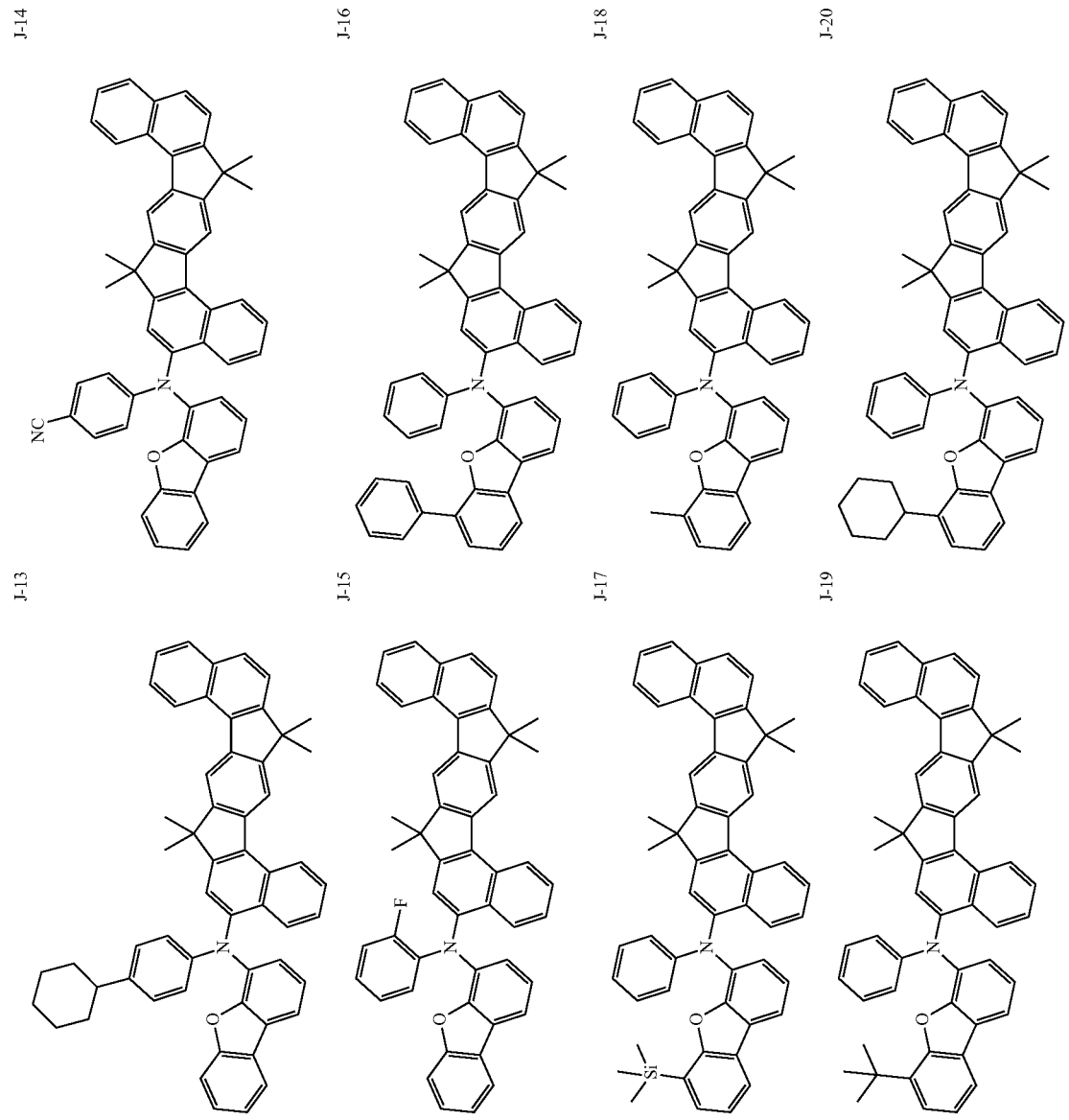

-continued
[Formula 70]
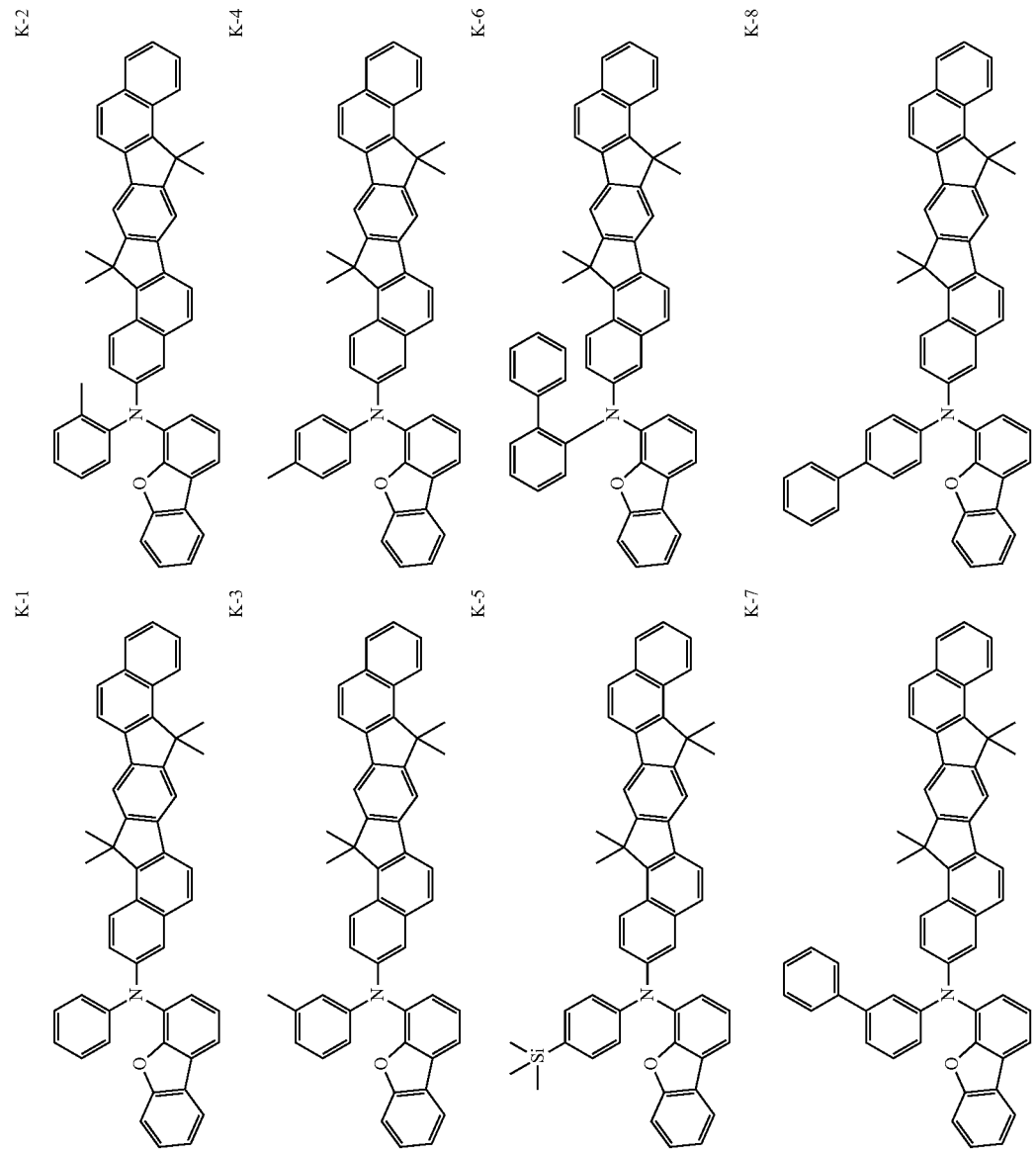

-continued
K-9
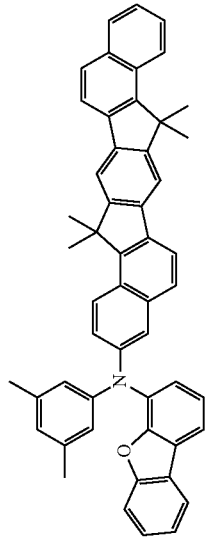
K-10
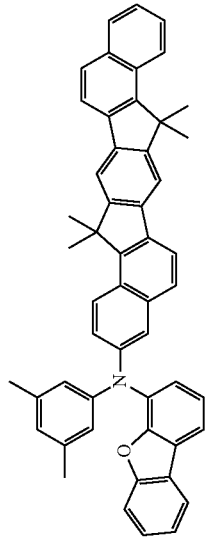
K-11
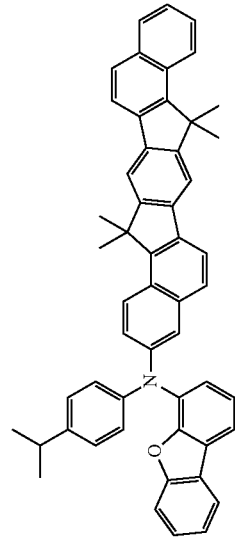
K-12
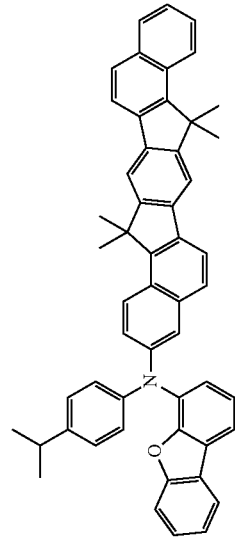
K-13
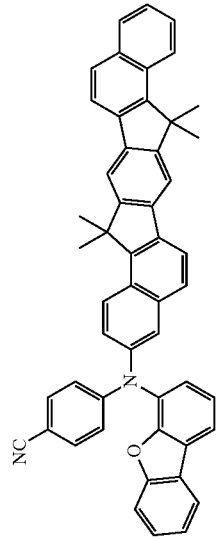
K-14
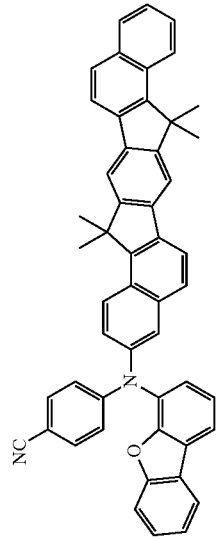
K-15
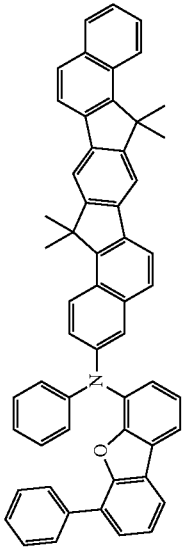
K-16
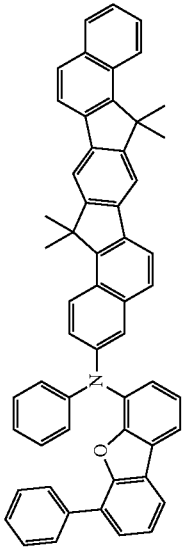
[Formula 71]
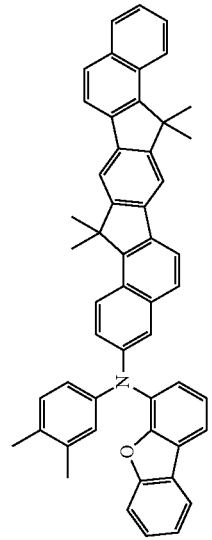
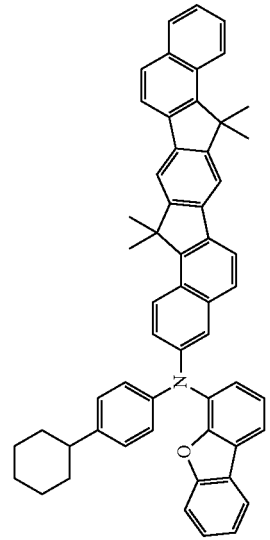
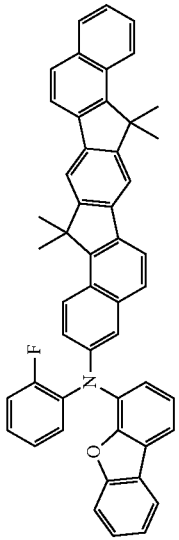

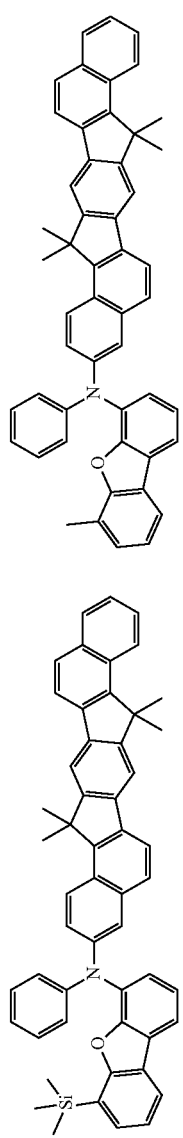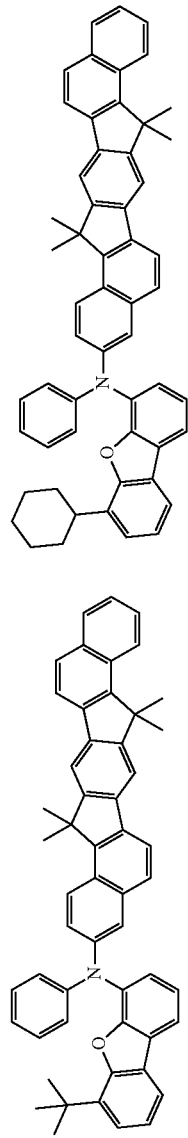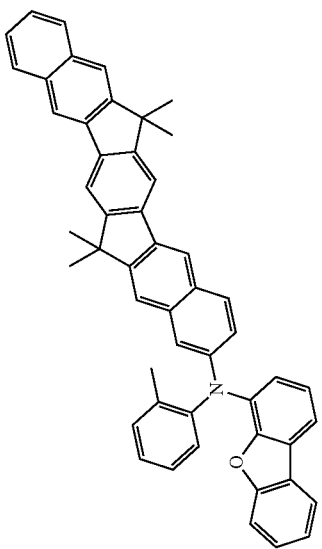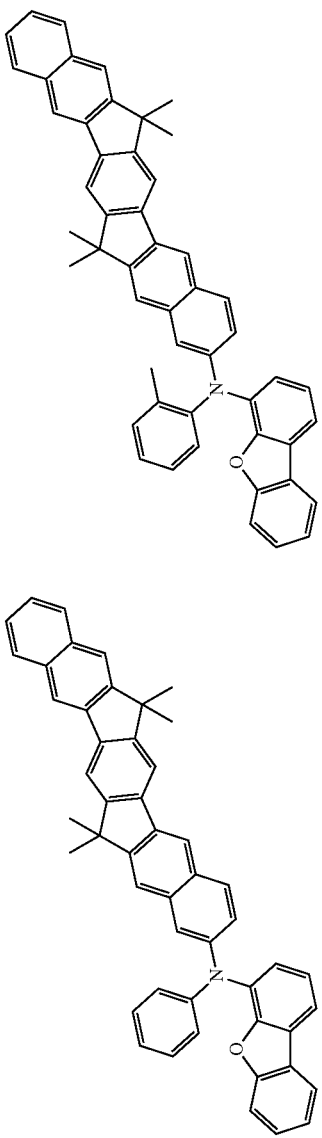
[Formula 72]

-continued
L-3 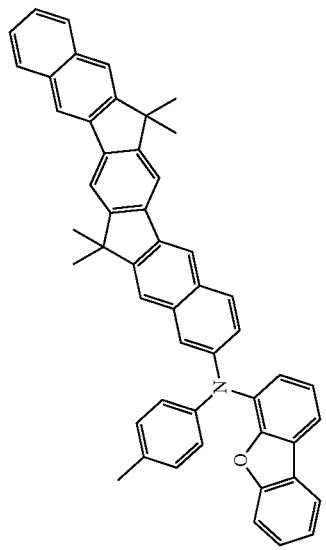
L-5 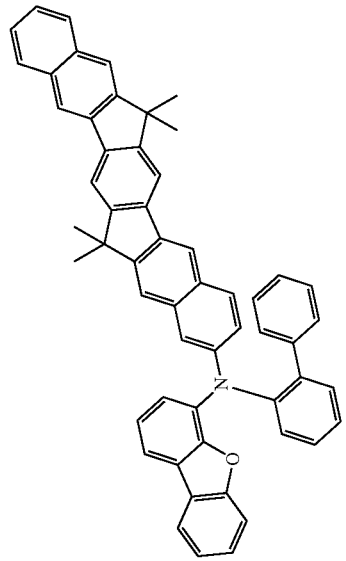
L-7 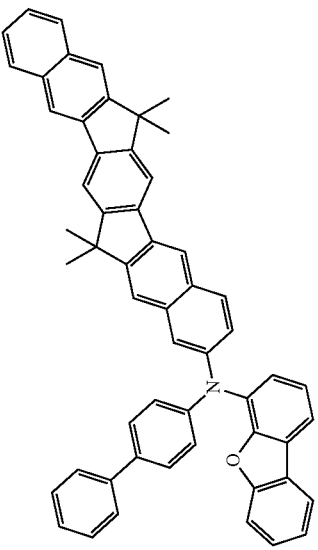
L-4 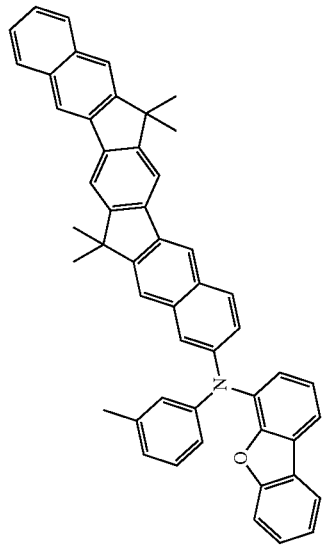
L-6 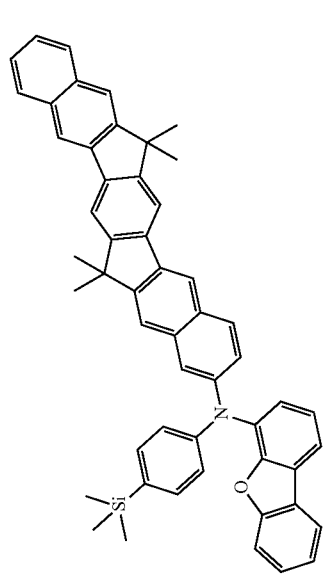
L-8 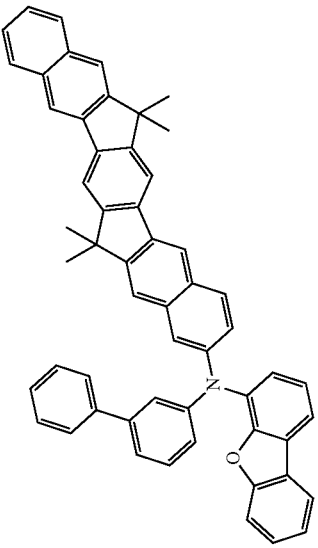

-continued
L-9
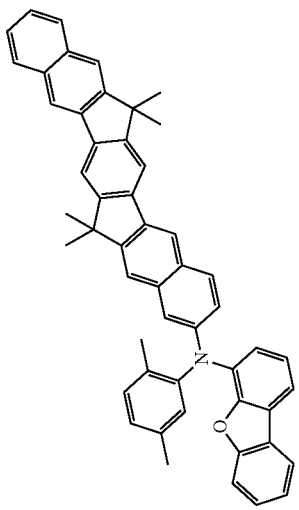
L-10
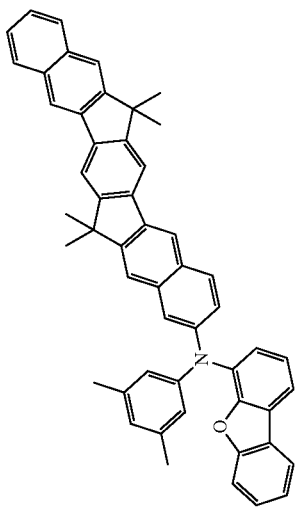
L-11
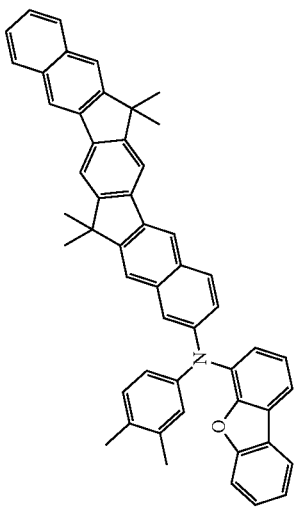
[Formula 73]
L-12
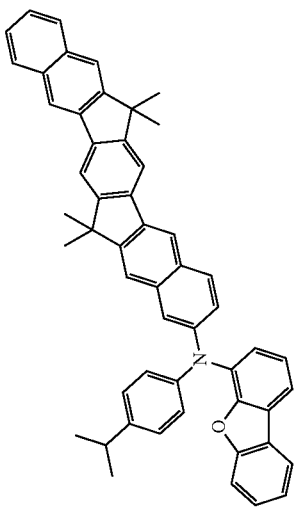
L-13
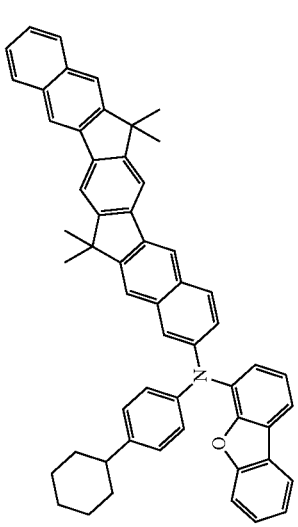
L-14
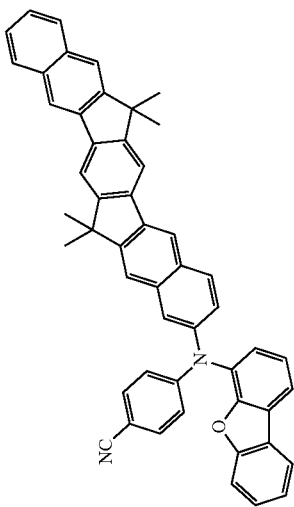

-continued
L-15 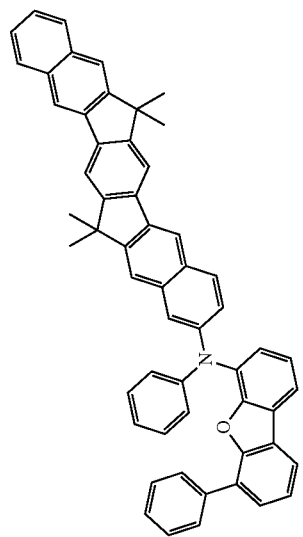
L-16 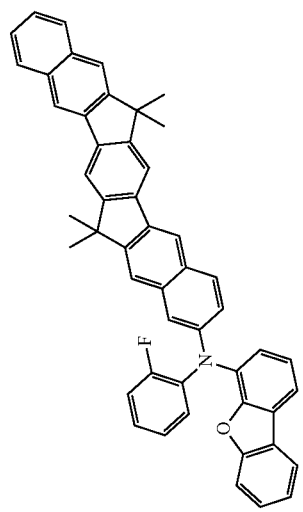
L-17 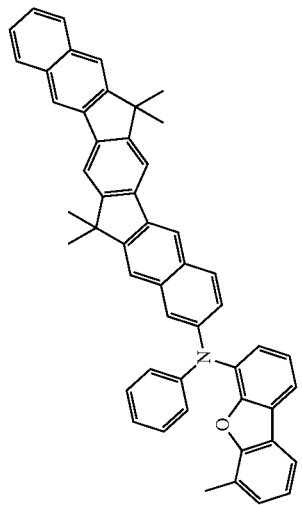
L-18 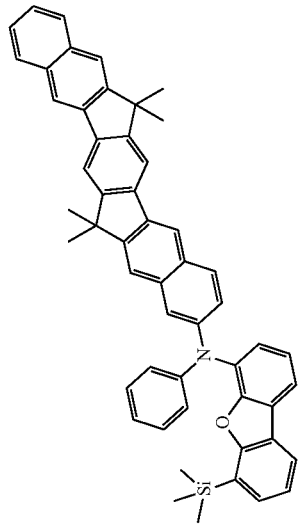
L-19 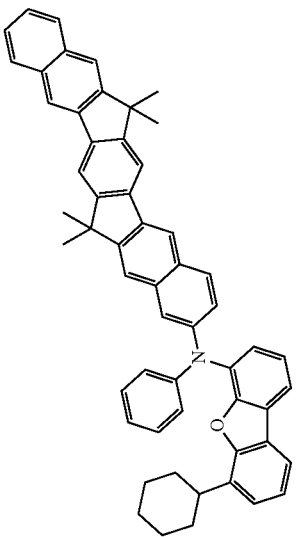
L-20 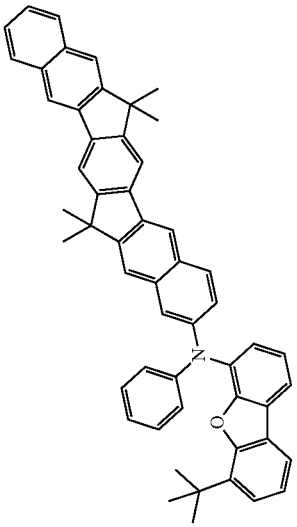

[Formula 74]
-continued
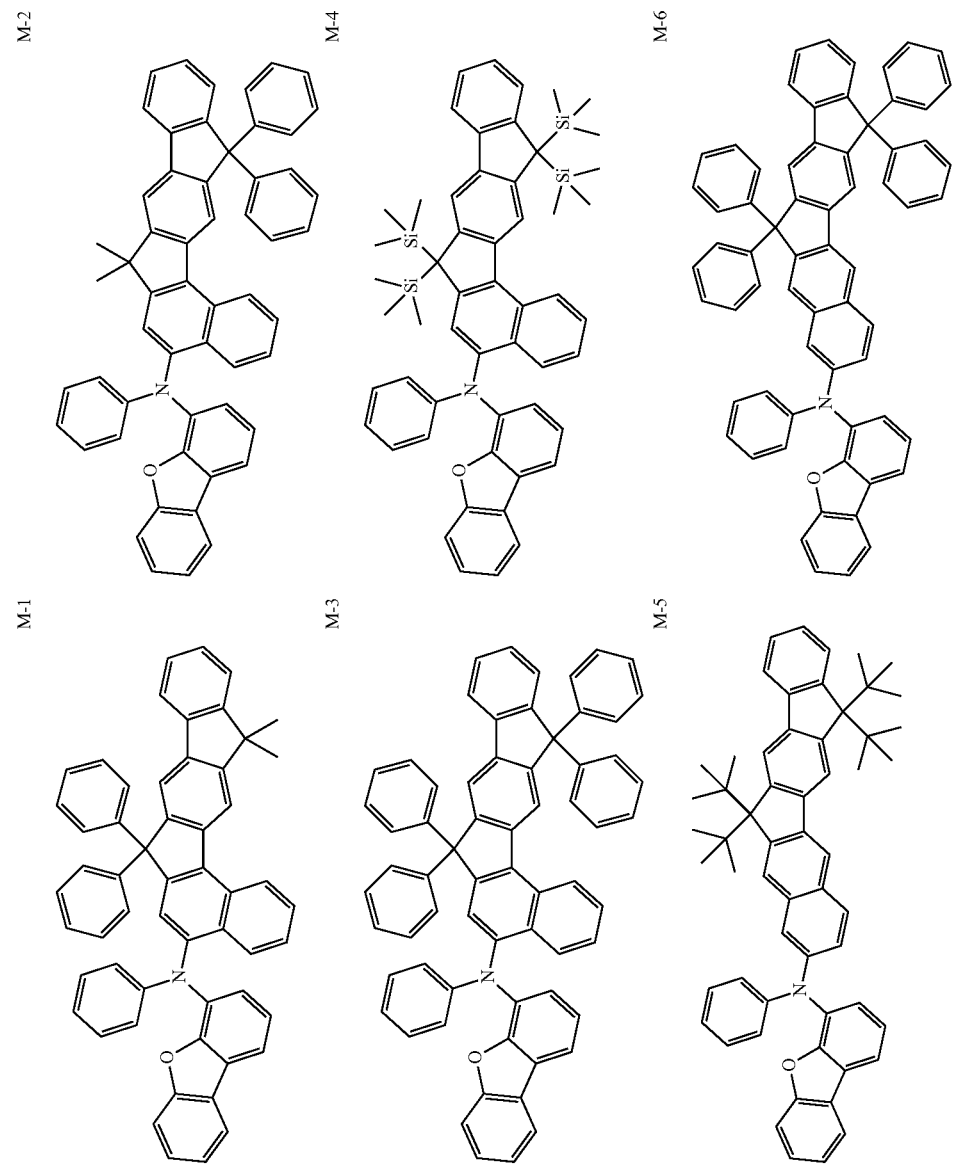

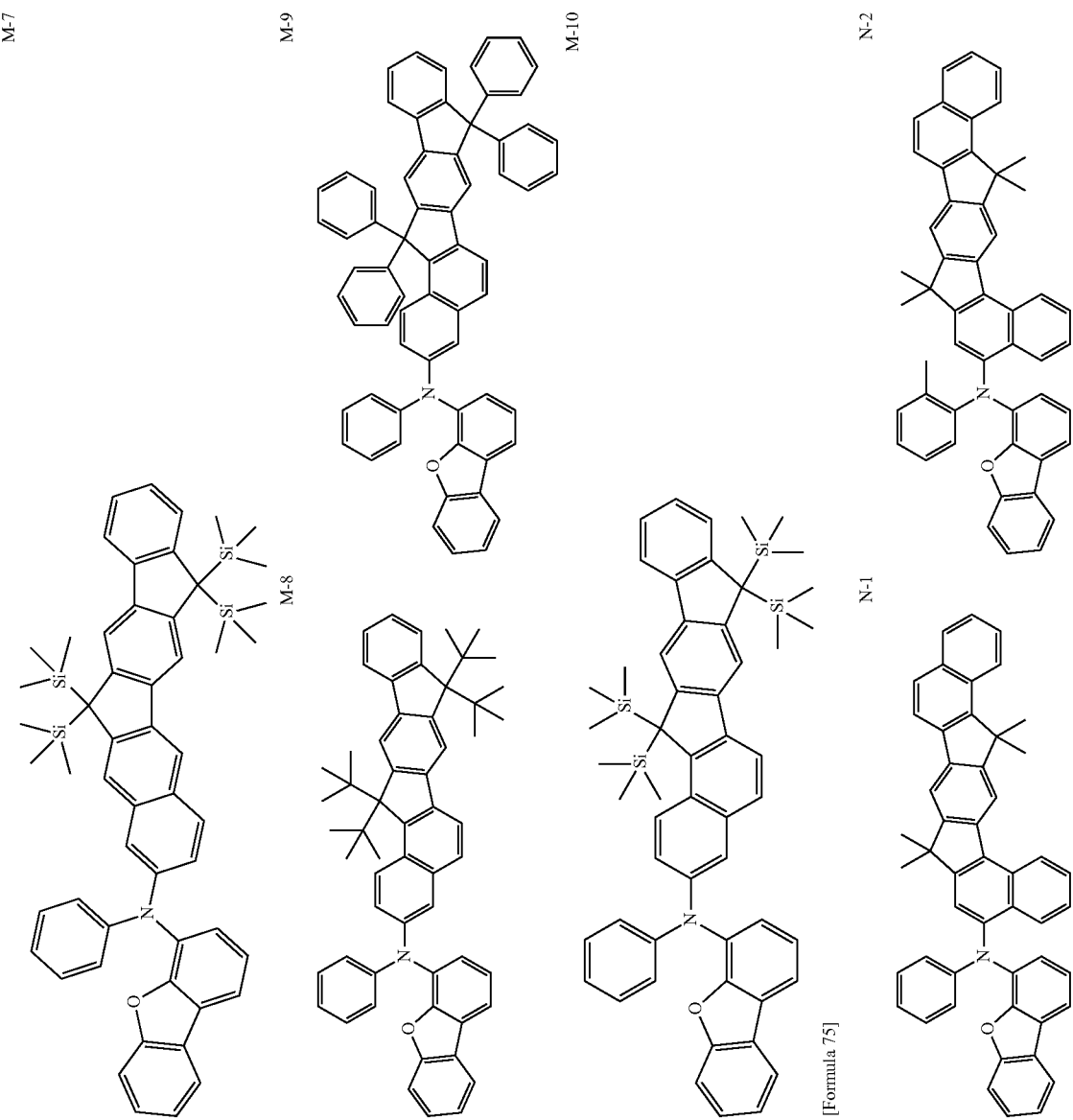

-continued
N-3
N-4
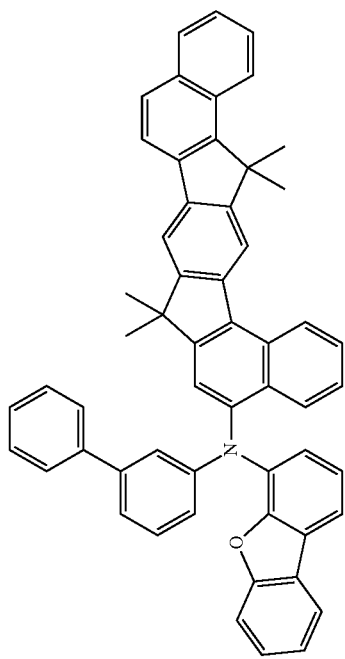
N-5
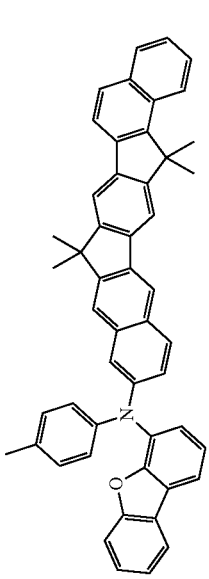
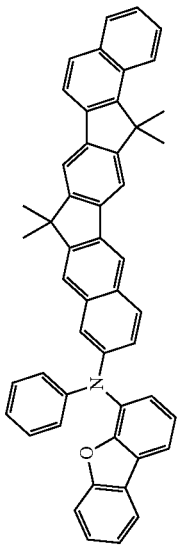
N-6
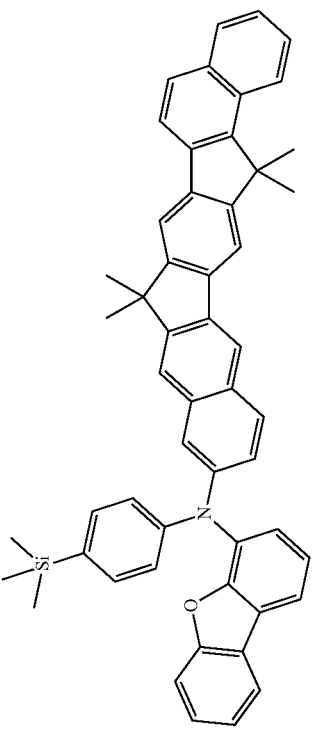

-continued
N-7
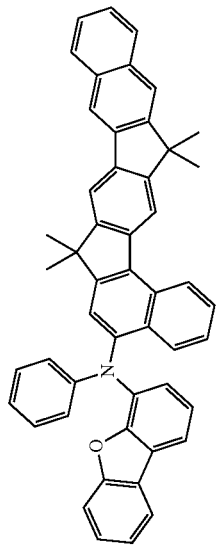
N-8
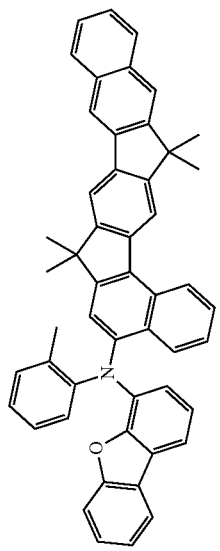
N-9
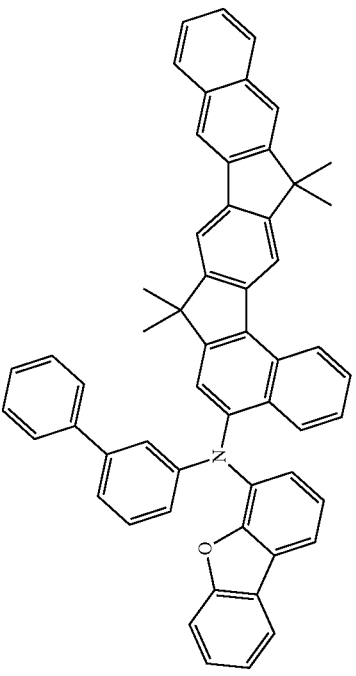
N-10
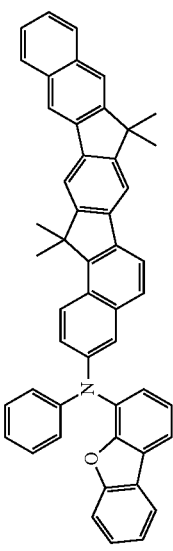
N-11
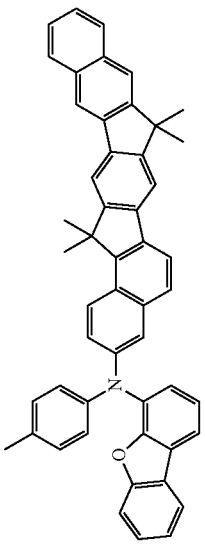
[Formula 76]

-continued
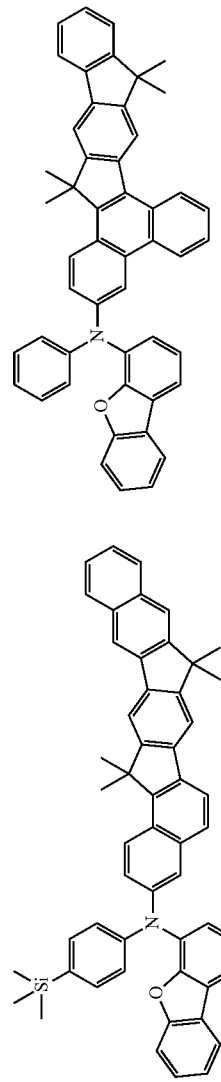
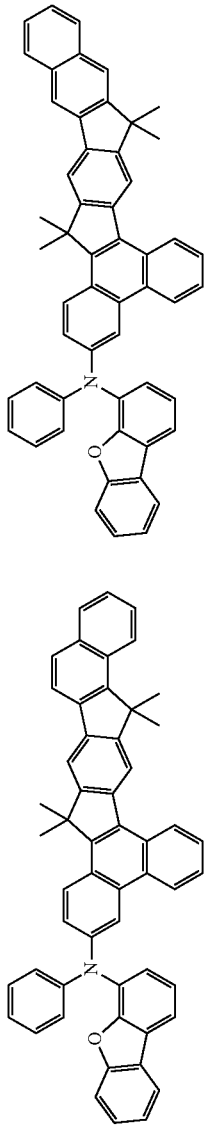
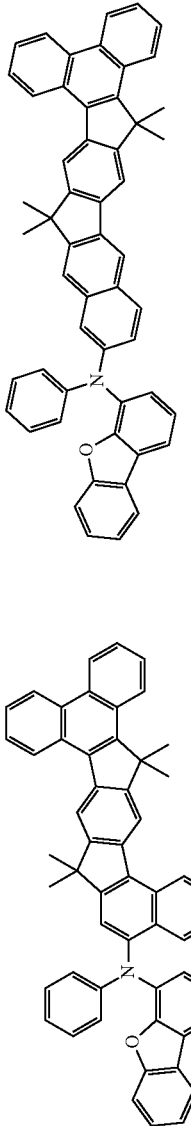
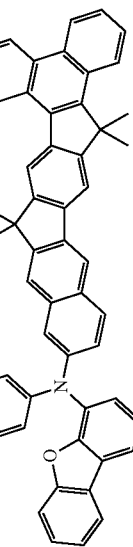
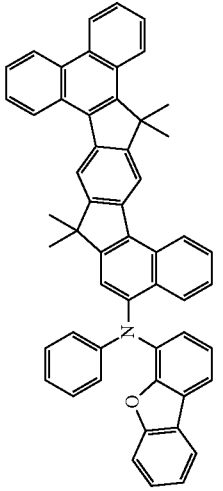
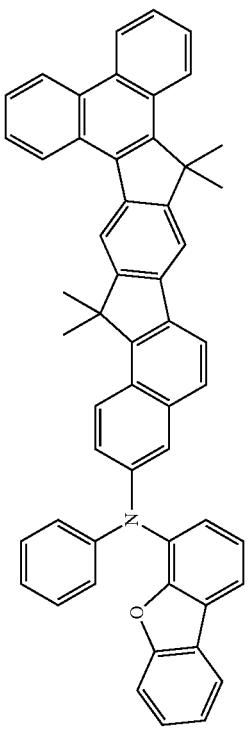

-continued
[Formula 77]
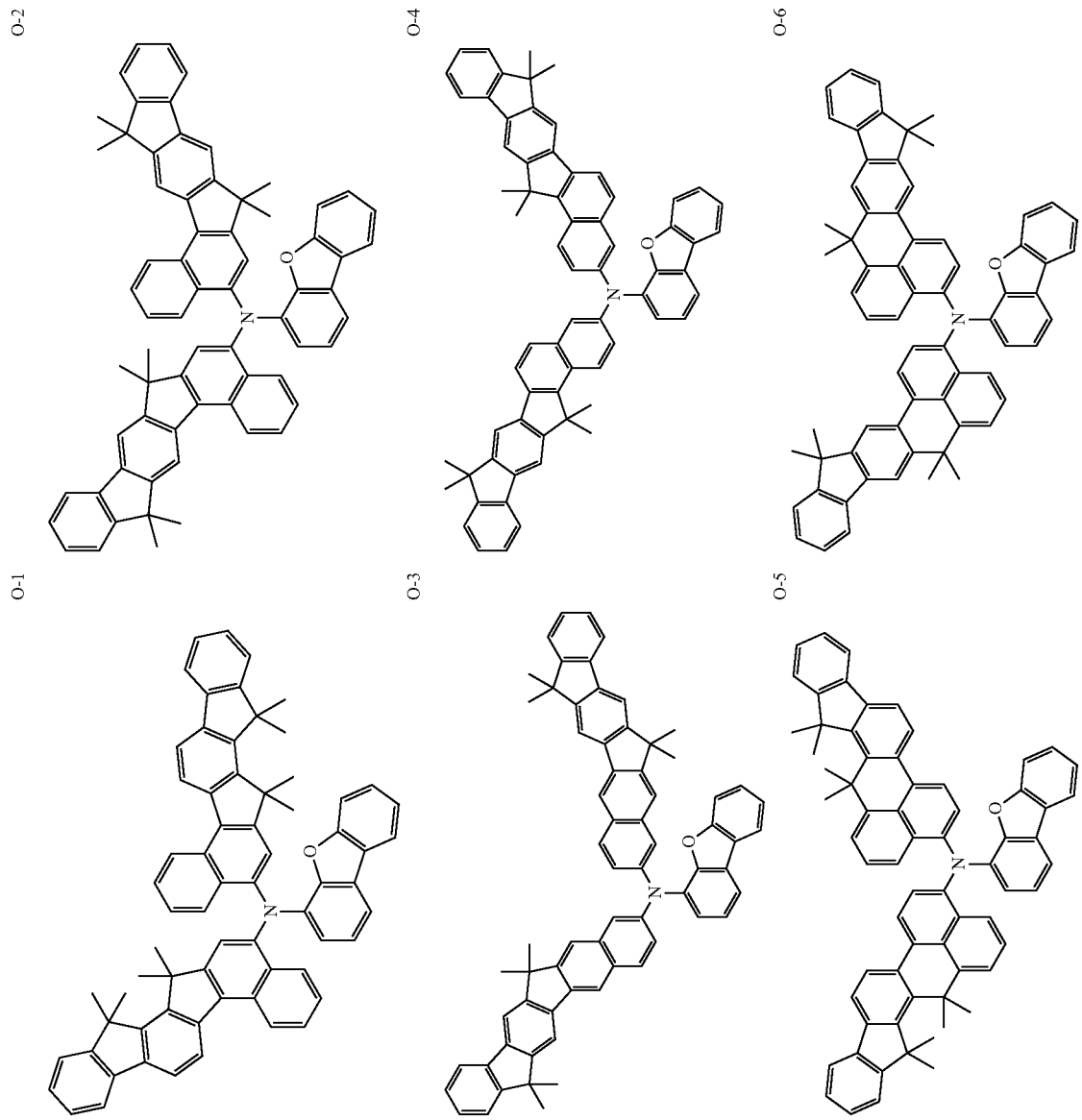

[Formula 78]
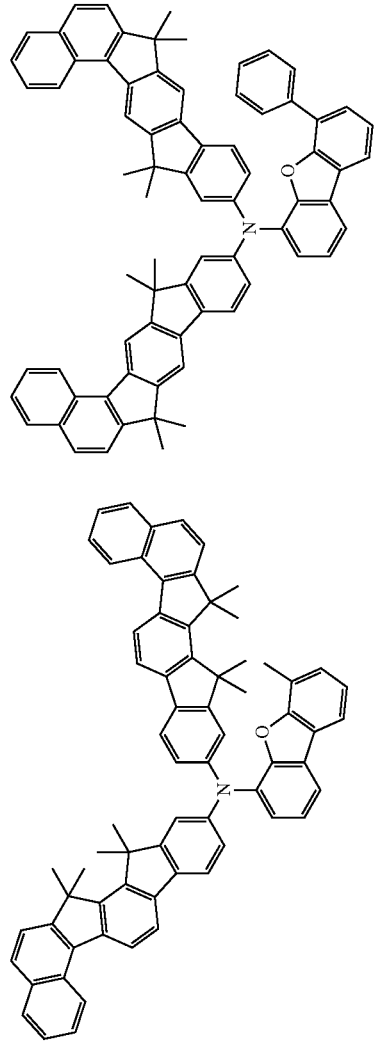
O-7
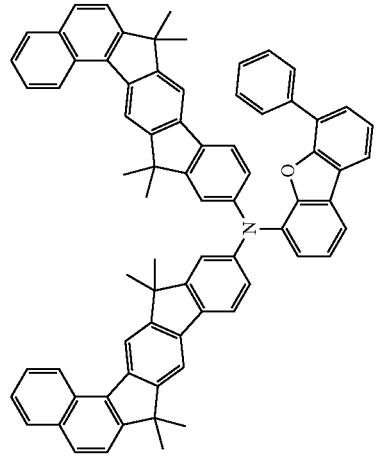
O-8
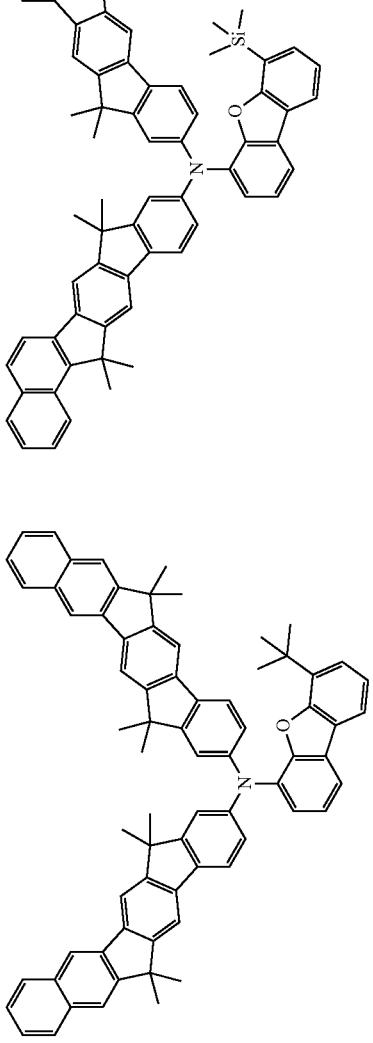
O-9
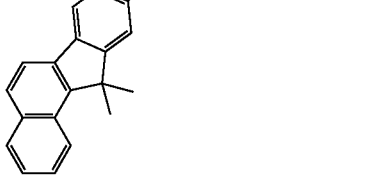
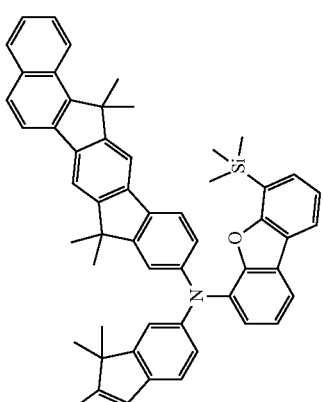
O-10

-continued
O-11
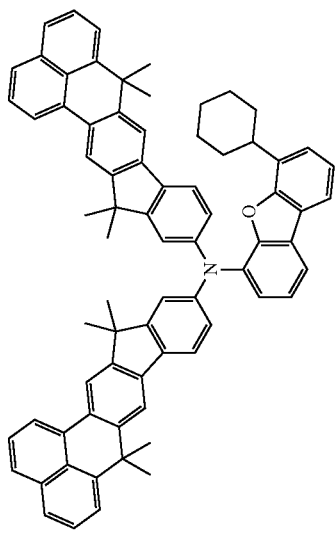
O-12
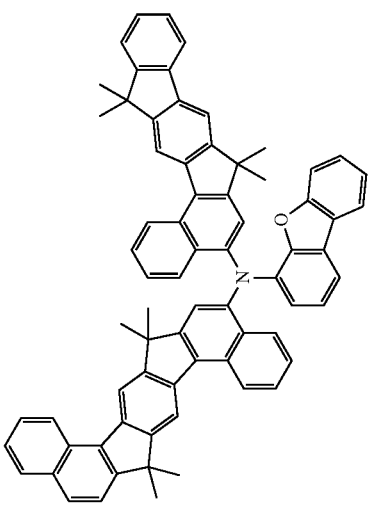
[Formula 79]
O-13
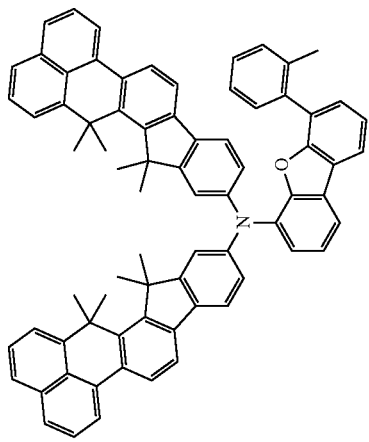
O-14
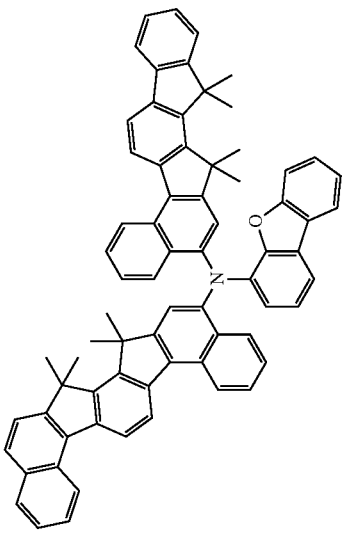

O-15
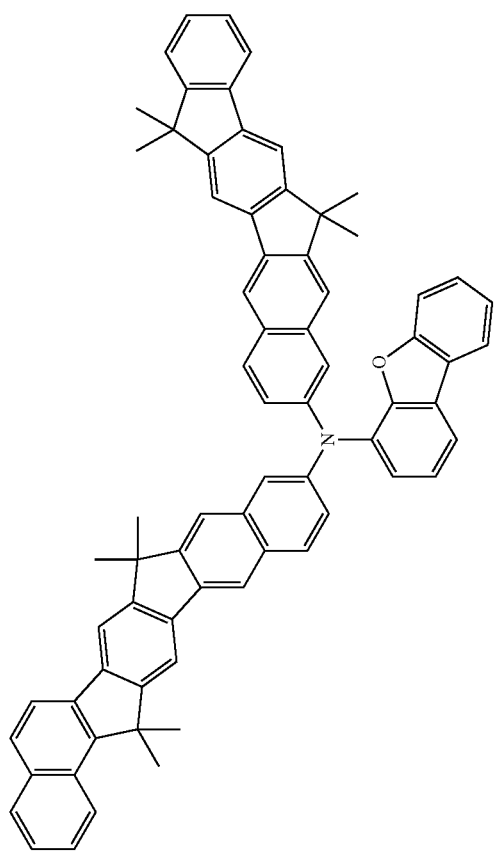
O-16
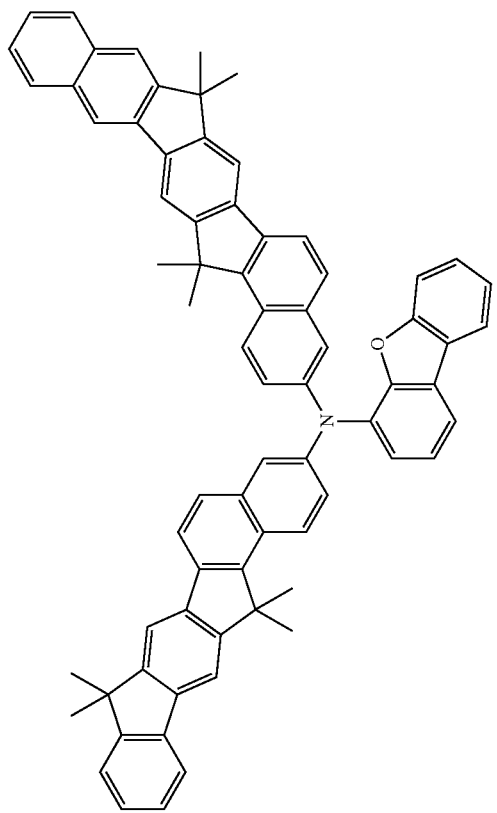

-continued
O-17
O-18
O-19
O-20
[Formula 80]
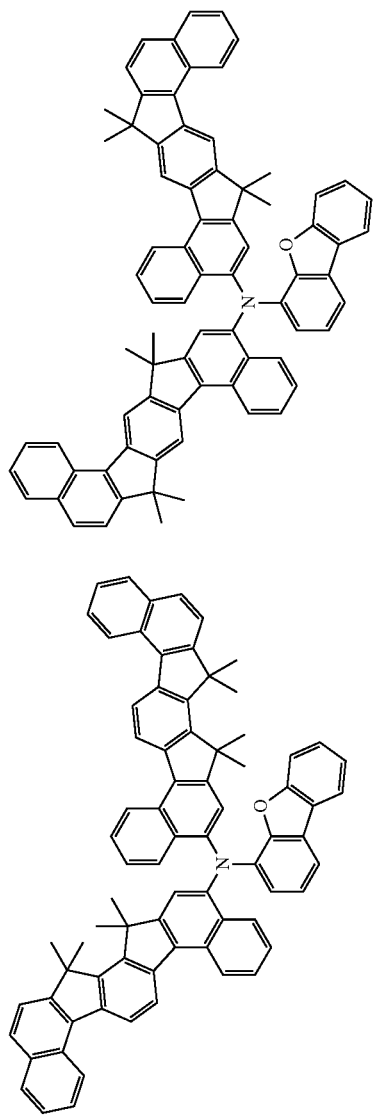
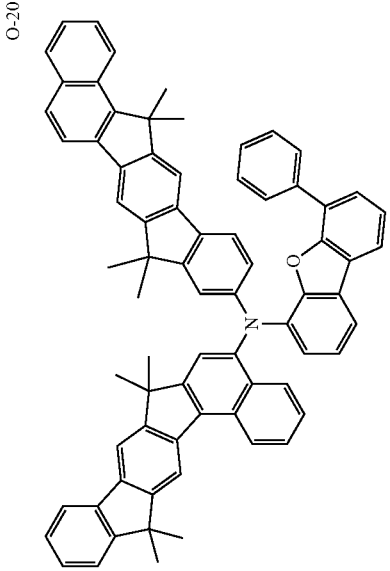
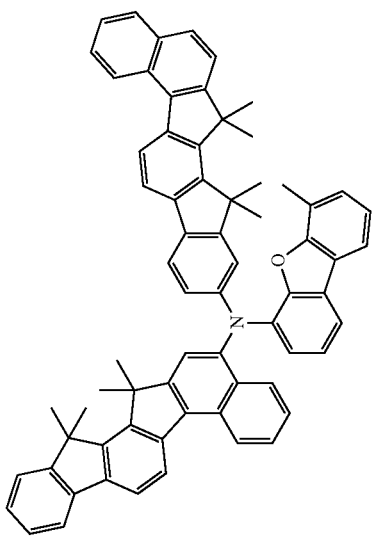

-continued
O-21
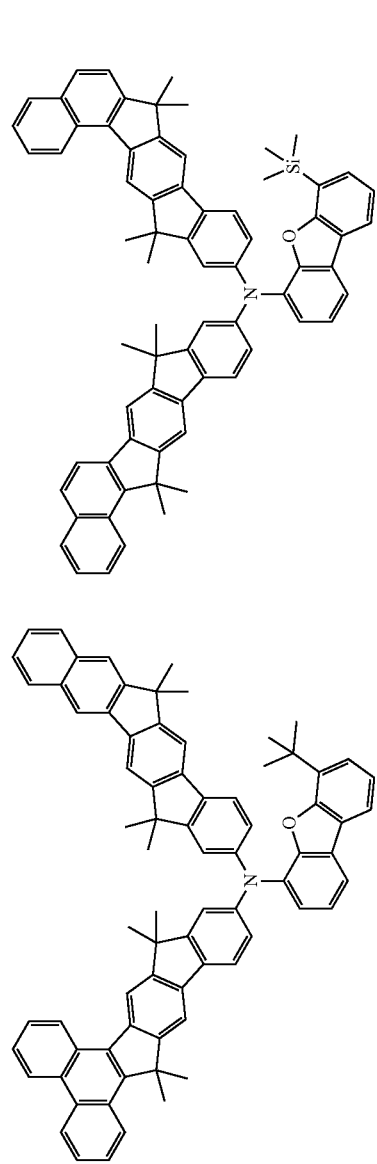
O-22
O-23
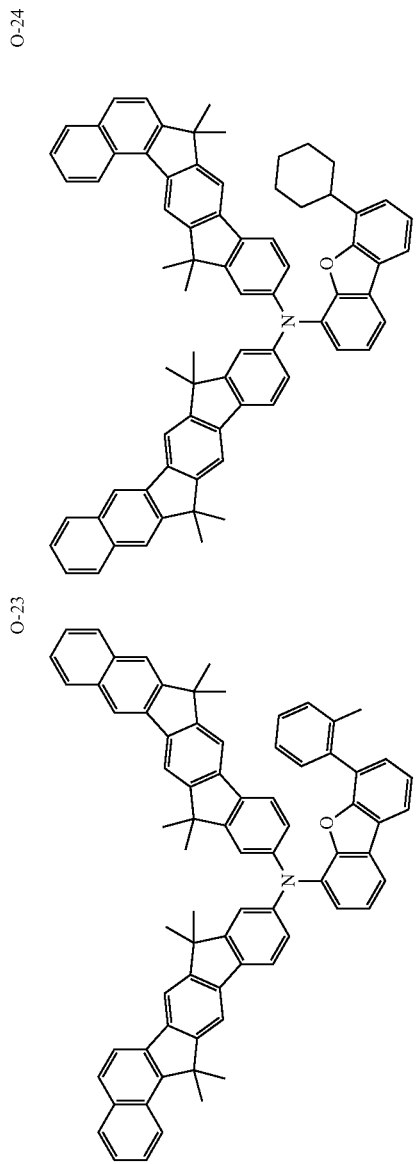
O-24

[Formula 81]
P-1
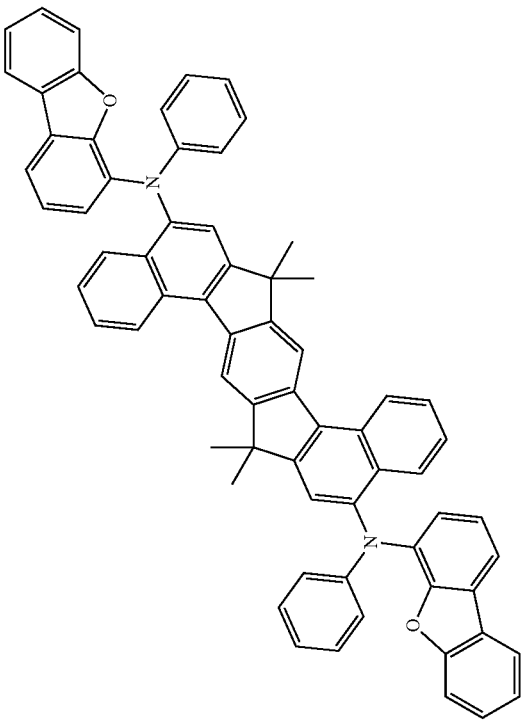
P-2
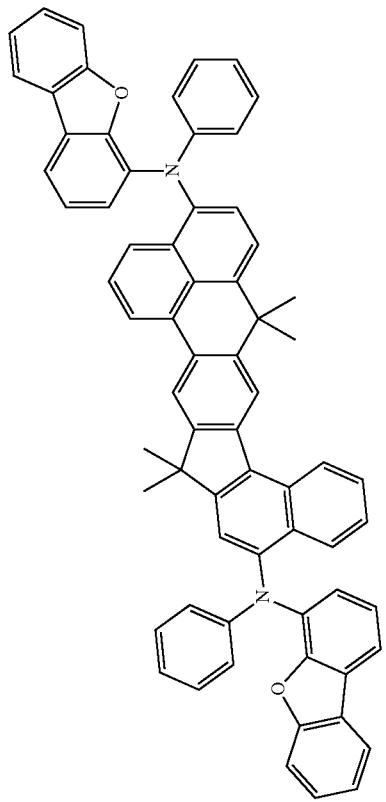

P-3
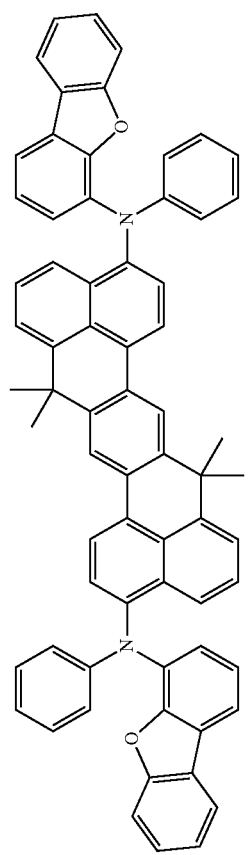
P-4
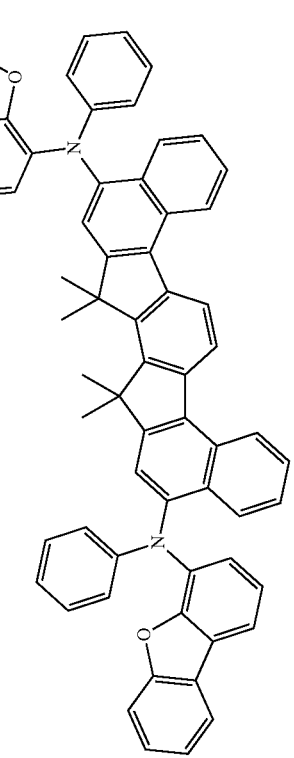
P-5
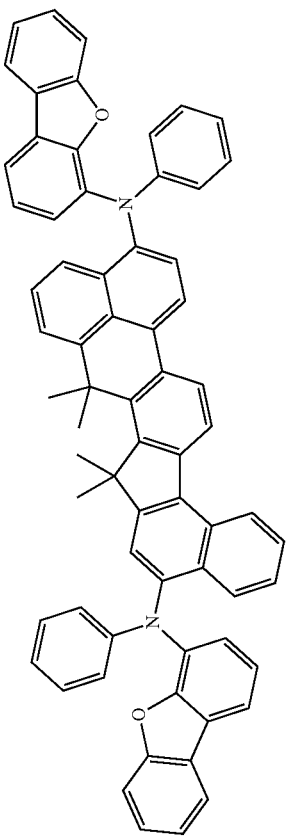

P-6
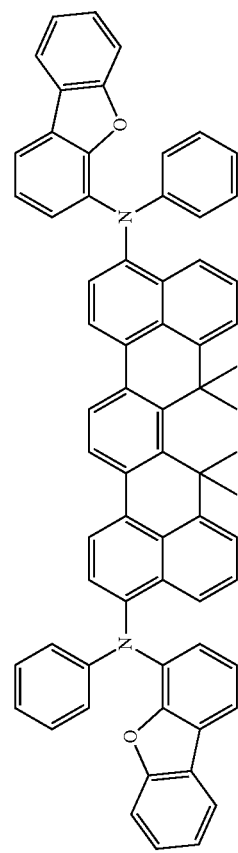
P-7
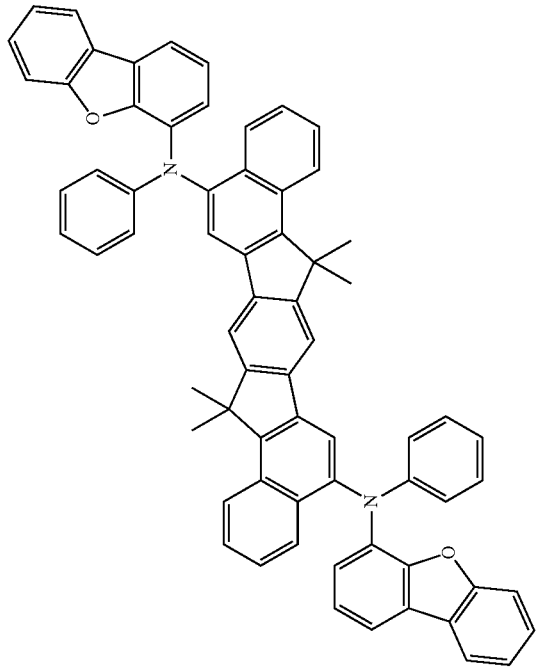
P-8
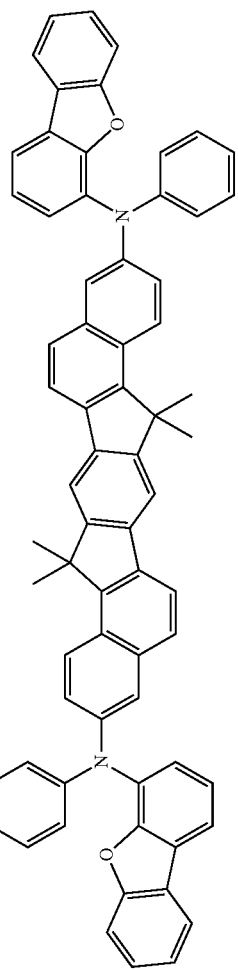

[Formula 82]
P-9
P-10
P-11
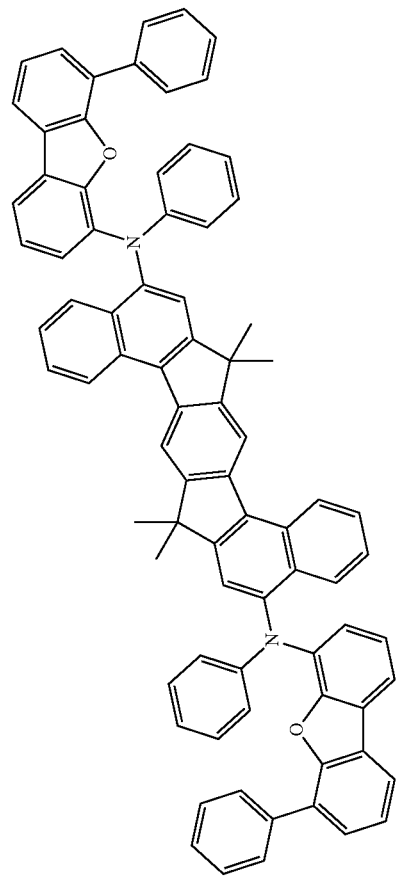
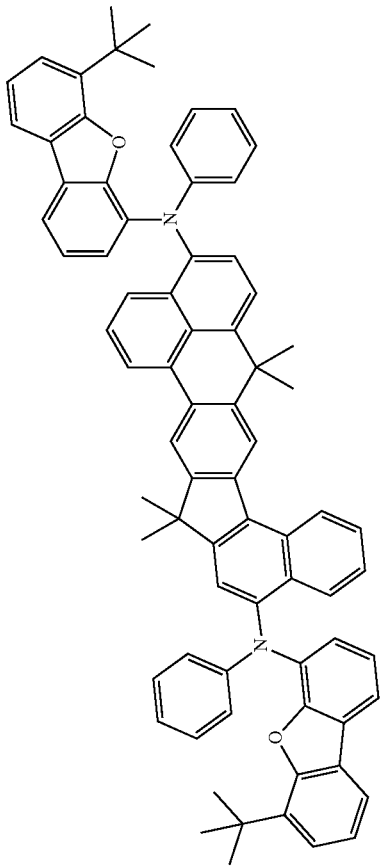
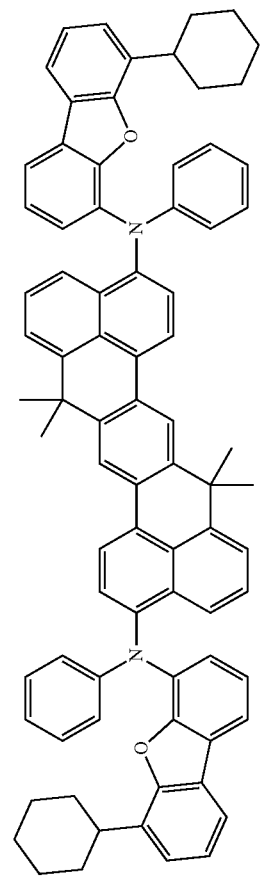

P-12
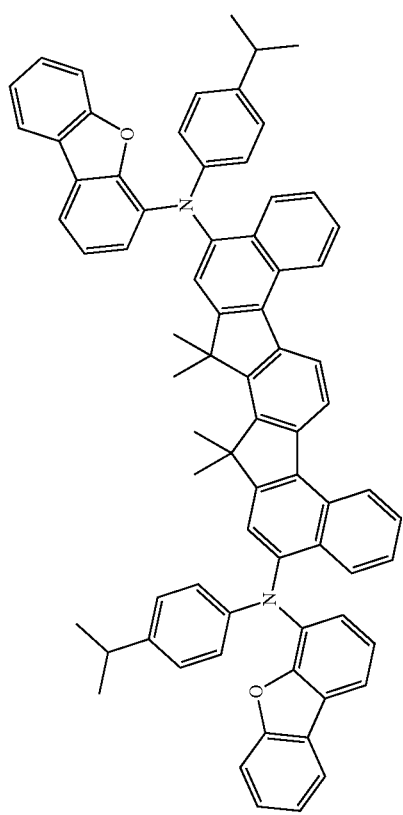
P-13
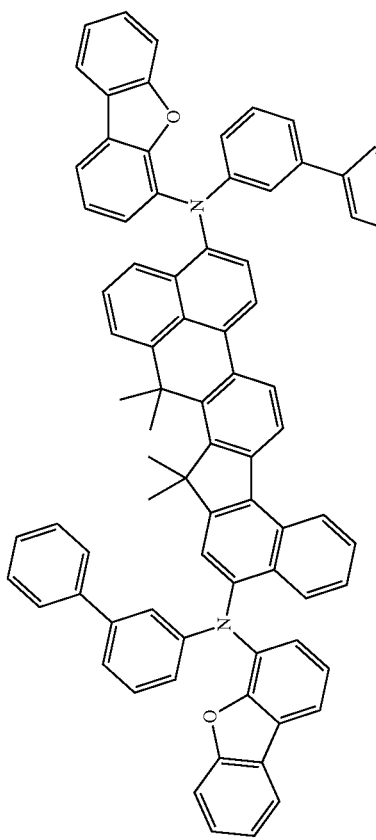
P-14
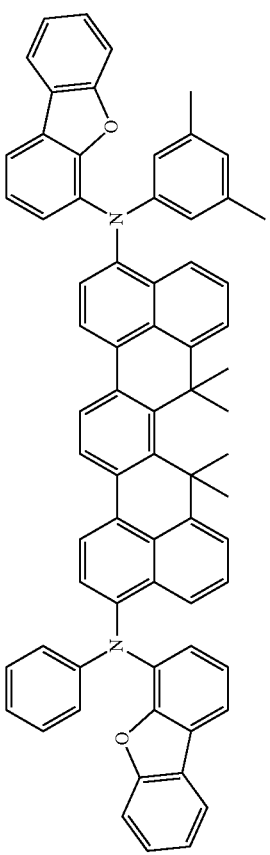

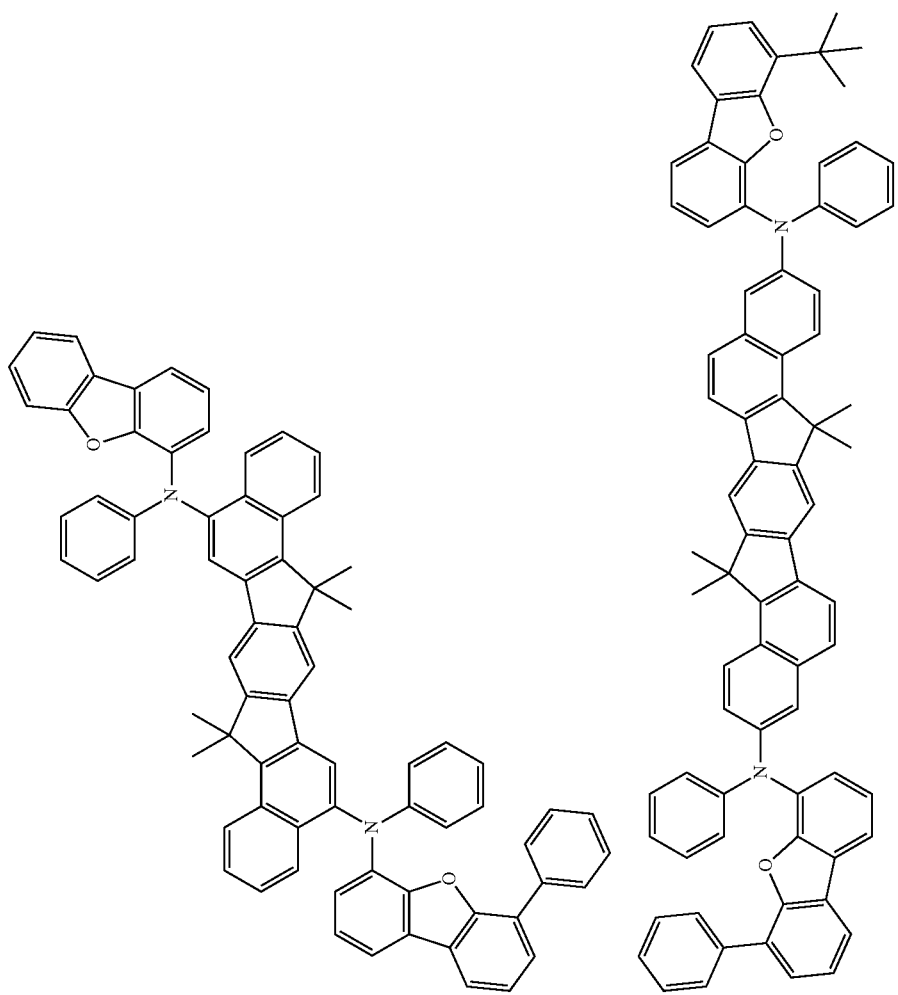

-continued
[Formula 83]
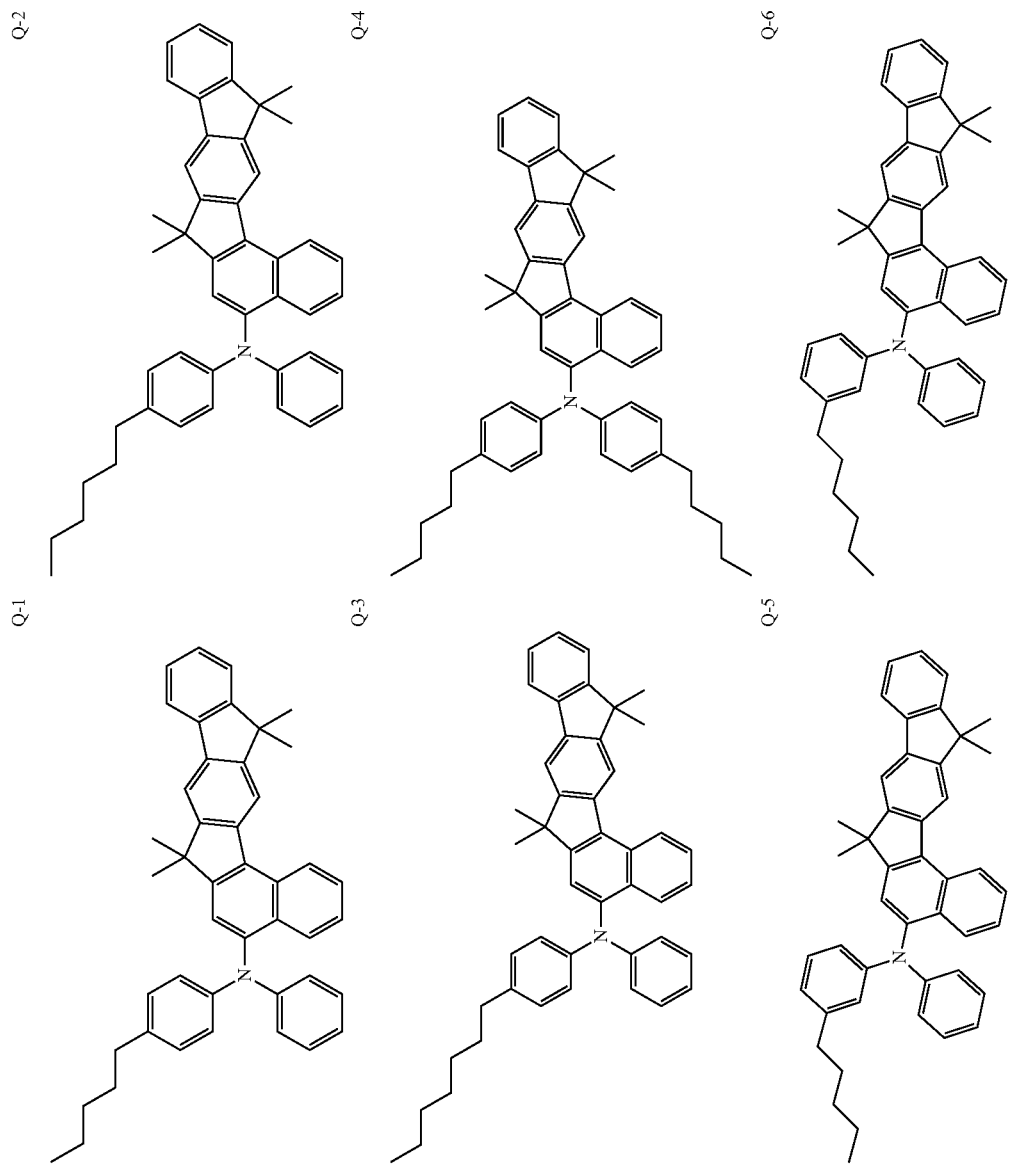

Q-7
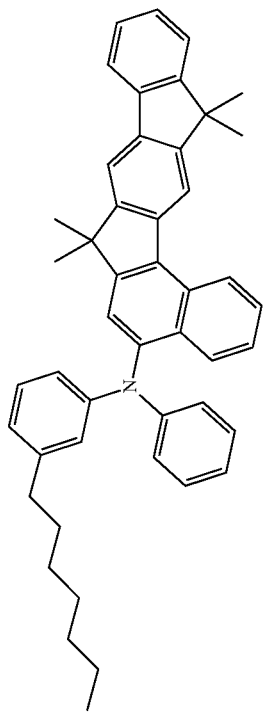
Q-8
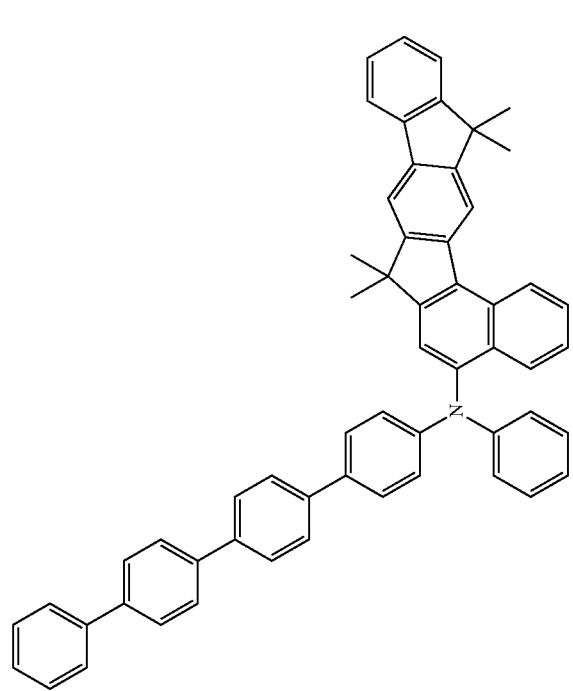
Q-9
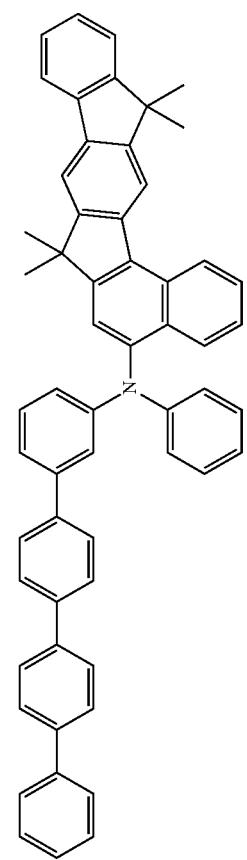
[Formula 84]

-continued
Q-10 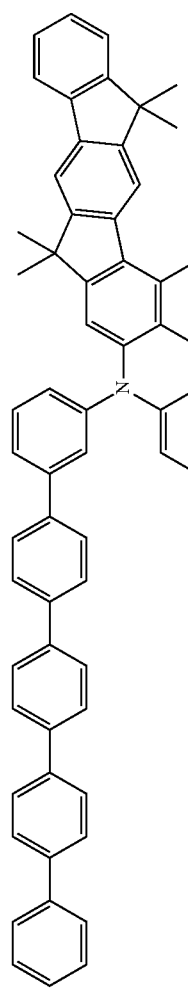
Q-11 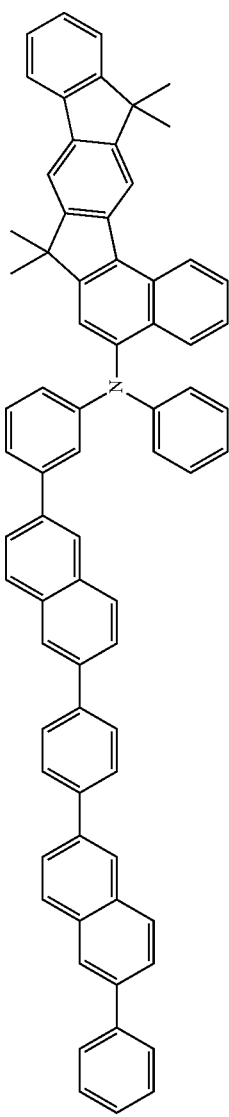
Q-12 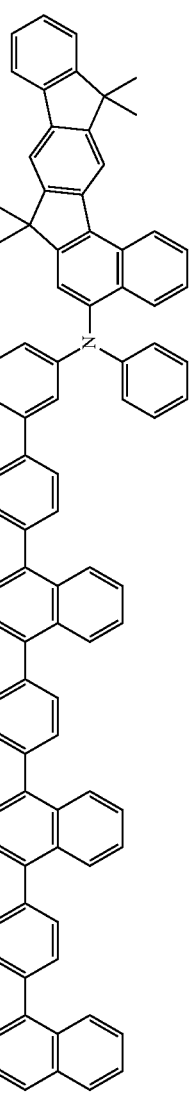

-continued
Q-13
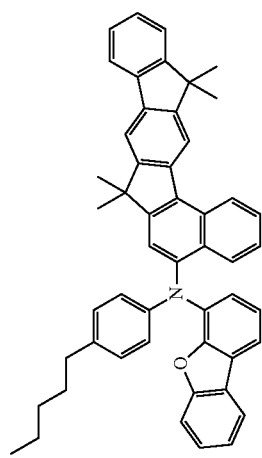
Q-14
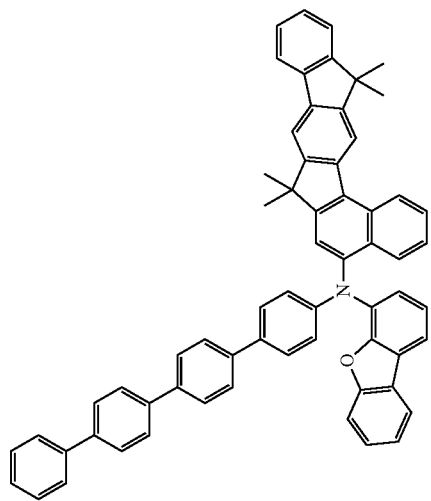
Q-15
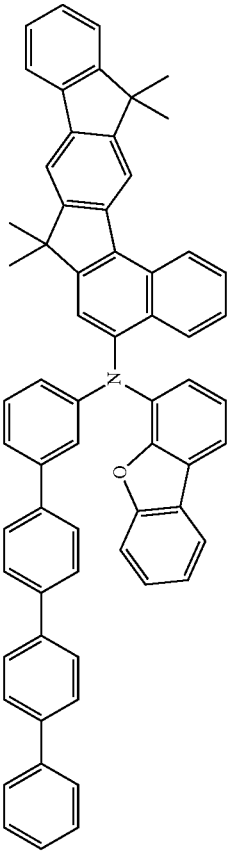
(1)
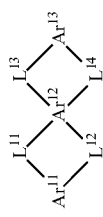
(2)
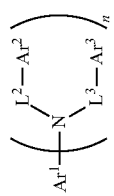
(3)
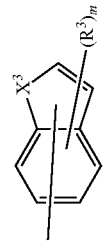

Organic EL Device Material

The compound of the first exemplary embodiment is usable as an organic EL device material. In this case, the organic EL device material may consist of the compound of the first exemplary embodiment, or may contain other material(s) in addition to the compound of the first exemplary embodiment.

Organic EL Device

Arrangement(s) of Organic EL Device

Arrangement(s) of an organic EL device of the first exemplary embodiment will be described below.

The organic EL device of the first exemplary embodiment includes a pair of electrodes and an organic layer disposed between the electrodes. The organic layer includes at least one layer formed of an organic compound. The organic layer may contain an inorganic compound.

The organic layer of the organic EL device includes at least one emitting layer. Specifically, for instance, the organic layer may consist of a single emitting layer, or may include layers usable in a typical organic EL device, such as a hole injecting layer, a hole transporting layer, an electron injecting layer, an electron transporting layer, a hole blocking layer and an electron blocking layer.

Representative arrangement examples of an organic EL device are as follows:
(a) anode/emitting layer/cathode;
(b) anode/hole injecting-transporting layer/emitting layer/cathode;
(c) anode/emitting layer/electron injecting-transporting layer/cathode;
(d) anode/hole injecting-transporting layer/emitting layer/electron injecting-transporting layer/cathode; and
(e) anode/hole injecting-transporting layer/emitting layer/blocking layer/electron injecting-transporting layer/cathode.

Among the above, the arrangement (d) is suitably usable, but the arrangement of the invention is not limited to the above arrangements.

It should be noted that the "emitting layer", which is an organic layer with a luminescent function, contains a host material and a dopant material when employing a doping system. At this time, the host material has a function to mainly promote recombination of electrons and holes and trap excitons within the emitting layer while the dopant material has a function to promote an efficient emission from the excitons obtained by the recombination. In a phosphorescent device, the host material has a function of trapping the excitons, which are generated mainly in the dopant, within the emitting layer.

The "hole injecting-transporting layer" means "at least one of a hole injecting layer and a hole transporting layer" while the "electron injecting-transporting layer" means "at least one of an electron injecting layer and an electron transporting layer." Herein, when the hole injecting layer and the hole transporting layer are provided, the hole injecting layer is preferably adjacent to the anode. When the electron injecting layer and the electron transporting layer are provided, the electron injecting layer is preferably adjacent to the cathode.

It should be noted that the electron transporting layer means an organic layer having the highest electron mobility among organic layers in an electron transporting region existing between the emitting layer and the cathode. When the electron transporting region is provided by a single layer, the single layer is the electron transporting layer. In a phosphorescent organic EL device, a blocking layer, the electron mobility of which is not necessarily high, may be provided between the emitting layer and the electron transporting layer to prevent dissipation of an excitation energy generated in the emitting layer, as shown in the arrangement (e). Therefore, the organic layer adjacent to the emitting layer is not always the electron transporting layer.

The FIGURE schematically shows an exemplary arrangement of an organic EL device of the first exemplary embodiment.

An organic EL device 1 includes a light-transmissive substrate 2, an anode 3, a cathode 4, and an organic layer 10 provided between the anode 3 and the cathode 4.

The organic layer 10 includes an emitting layer 5 containing a host material and a dopant material. The organic layer 10 also includes a hole transporting layer 6 provided between the emitting layer 5 and the anode 3. The organic layer 10 also includes an electron transporting layer 7 provided between the emitting layer 5 and the cathode 4.

Emitting Layer

The emitting layer is a layer containing a highly luminescent substance, and a variety of materials are usable to form the emitting layer. For instance, the highly luminescent substance may be a fluorescent compound emitting fluorescence or a phosphorescent compound emitting phosphorescence. The fluorescent compound is capable of emission from a singlet excited state. The phosphorescent compound is capable of emission from a triplet excited state.

To form the emitting layer, the above highly luminescent substance (the dopant material) may be dispersed in another substance (the host material). A variety of substances are usable as the substance where the highly luminescent substance is to be dispersed. Specifically, a substance having the lowest unoccupied orbital level (LUMO level) higher than that of the highly luminescent substance and the highest occupied orbital level (HOMO level) lower than that of the highly luminescent substance is preferably usable.

In the first exemplary embodiment, the dopant material is dispersed in the host material.

Dopant Material

In the first exemplary embodiment, the compound represented by the formula (1) is preferably usable as the dopant material.

In the compound represented by the formula (1), $Ar^1$ has the structure represented by the formula (2), and, further, $Ar^3$ has the structure represented by the formula (3). The compound of the first exemplary embodiment thus emits pure-blue light when used in the organic EL device.

The compound represented by the formula (1) has a long alkyl chain when having the structure represented by the formula (1a). This is because R' in the formula (1a) has a structure where an integral number of 4 to 20 of $CR^{101a}R^{102a}$ are bonded.

A typical compound having an extended alkyl chain has been known. However, the alkyl chain of the structure represented by the formula (1a) is longer than that of the typical compound, and the use of such a compound having a long alkyl chain as a dopant material has not been considered. The compound represented by the formula (1) has a high orientation due to a long-extended alkyl chain represented by the formula (1a). When the compound represented by the formula (1) is used as the dopant material, the luminous efficiency of the organic EL device is expected to be improved due to the high orientation of the compound.

The compound represented by the formula (1) has a structure where a conjugated system is extended long when having the structure represented by the formula (11a). This is because Ar in the formula (11a) has a structure where an integral number of 5 to 20 of substituted or unsubstituted divalent aromatic hydrocarbon groups having 6 to 18 ring carbon atoms or substituted or unsubstituted divalent heterocyclic groups having 5 to 15 ring atoms are bonded.

Although a typical compound having an extended conjugated system has been known, the conjugated system of the structure represented by the formula (11a) is longer than that of the typical compound. The use of such a compound having a long conjugated system as a dopant material has not been considered. The compound represented by the formula (1) has a high orientation due to a long-extended conjugated system represented by the formula (11a). When the compound represented by the formula (1) is used as the dopant material, the luminous efficiency of the organic EL device is expected to be improved due to the high orientation of the compound.

It should be noted that when the emitting layer contains the compound of the first exemplary embodiment as the dopant material, the content of the compound of the first exemplary embodiment in the emitting layer is preferably in a range from 0.1 mass % to 20 mass %, more preferably in a range from 1 mass % to 10 mass %.

Host Material

As the substance (the host material) where the highly luminescent substance is to be dispersed, the following substances 1) to 4) are usable: 1) metal complexes such as an aluminum complex, beryllium complex and zinc complex; 2) heterocyclic compounds such as an oxadiazole derivative, benzimidazole derivative and phenanthroline derivative; 3) fused aromatic compounds such as a carbazole derivative, anthracene derivative, phenanthrene derivative, pyrene derivative and chrysene derivative; and 4) aromatic amine compounds such as a triarylamine derivative and fused polycyclic aromatic amine derivative.

In the first exemplary embodiment, an anthracene derivative represented by a formula (100) below is preferably used as the host material.

[Formula 85]

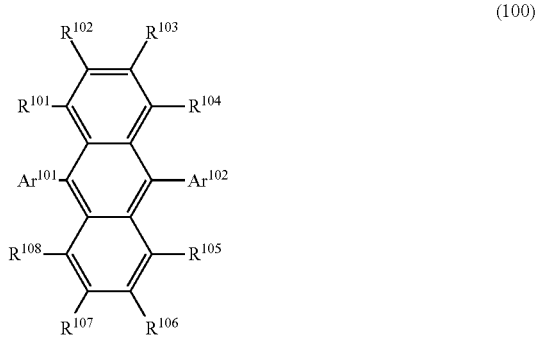

(100)

In the formula (100), $Ar^{101}$ and $Ar^{102}$ each independently represent a substituted or unsubstituted monocyclic group having 5 to 30 ring atoms, substituted or unsubstituted fused ring group having 10 to 30 ring atoms, chain group formed by bonding two groups selected from the group consisting of the monocyclic group and the fused ring group, or chain group formed by bonding three groups selected from the group consisting of the monocyclic group and the fused ring group.

The monocyclic group or groups and the fused ring group or groups in the chain group may be mutually the same or different, and the groups in the chain group may be bonded to each other to form a ring.

In the formula (100), $R^{101}$ to $R^{108}$ each independently represent a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, a substituted or unsubstituted arylthio group having 6 to 30 ring carbon atoms, a substituted or unsubstituted monocyclic group having 5 to 30 ring atoms, a substituted or unsubstituted fused ring group having 10 to 30 ring atoms, a chain group formed by bonding two groups selected from the group consisting of the monocyclic group and the fused ring group, or a chain group formed by bonding three groups selected from the group consisting of the monocyclic group and the fused ring group.

Adjacent ones of $R^{101}$ to $R^{108}$ may be bonded to each other to form a ring or not bonded. $R^{101}$ and $R^{108}$ may be bonded to a carbon atom of an anthracene ring to form a ring or not bonded.

$Ar^{101}$ may be bonded to at least any one of adjacent $R^{101}$ to $R^{108}$ to form a ring or not bonded. $Ar^{102}$ may be bonded to at least any one of adjacent $R^{104}$ and $R^{105}$ to form a ring or not bonded. At least one of $Ar^{101}$ and $Ar^{102}$ may be bonded to a carbon atom of the anthracene ring to form a ring or not bonded.

In the formula (100), the fused ring group is a group where two or more cyclic structures are fused. For instance, of the above aromatic hydrocarbon group and heterocyclic group, a group where two or more cyclic structures are fused is usable.

In the formula (100), the monocyclic group is a monocyclic group where two or more cyclic structures are not fused. For instance, of the above aromatic hydrocarbon group and heterocyclic group, a monocyclic group is usable.

The monocyclic group has 5 to 30 ring atoms, preferably 5 to 20 ring atoms. Examples of the monocyclic group include aromatic hydrocarbon groups such as a phenyl group, biphenyl group, terphenyl group and quaterphenyl group, and heterocyclic groups such as a pyridyl group, pyrazyl group, pyrimidyl group, triazinyl group, furyl group and thienyl group. Among the above, a phenyl group, biphenyl group and terphenyl group are preferable.

The fused ring group has 10 to 30 ring atoms, preferably 10 to 20 ring atoms. Examples of the fused ring group include fused aromatic cyclic groups such as a naphthyl group, phenanthryl group, anthryl group, chrysenyl group, benzoanthryl group, benzophenanthryl group, triphenylenyl group, benzochrysenyl group, indenyl group, fluorenyl group, 9,9-dimethylfluorenyl group, benzofluorenyl group, dibenzofluorenyl group, fluoranthenyl group and benzofluoranthenyl group, and fused heterocyclic groups such as a benzofuranyl group, benzothiophenyl group, indolyl group, dibenzofuranyl group, dibenzothiophenyl group, carbazolyl group, quinolyl group and phenanthrolinyl group. Among the above, a naphthyl group, phenanthryl group, anthryl group, 9,9-dimethylfluorenyl group, fluoranthenyl group, benzoanthryl group, dibenzothiophenyl group, dibenzofuranyl group and carbazolyl group are preferable.

Examples of the chain group in the formula (100) provided by a combination of the above monocyclic group(s)

and fused ring group(s) include a group where a phenyl group, naphthyl group and phenyl group are bonded to be combined in this order from the anthracene ring.

Specific examples of the alkyl group, silyl group, alkoxy group, aryloxy group, aralkyl group and halogen atom for $R^{101}$ to $R^{108}$ in the formula (100) are the same as above, and the cycloalkyl group is the same as above.

Preferred examples of the substituents meant by "substituted or unsubstituted" for $Ar^{101}$ and $Ar^{102}$ and $R^{101}$ to $R^{18}$ in the formula (100) include a monocyclic group, fused ring group, alkyl group, cycloalkyl group, silyl group, alkoxy group, cyano group and halogen atom (in particular, fluorine). A monocyclic group and a fused ring group are particularly preferable. Specific preferred substituents are the same as the groups for the formula (100) as well as the above groups.

In the formula (100), a hydrogen atom includes isotopes having different numbers of neutrons, i.e., protium, deuterium and tritium.

The anthracene derivative represented by the formula (100) is preferably any one selected from the following anthracene derivatives (A), (B) and (C) depending on an arrangement and a desired property of an organic EL device where the anthracene derivative is to be used.

Anthracene Derivative (A)

The anthracene derivative (A) is an anthracene derivative where $Ar^{101}$ and $Ar^{102}$ in the formula (100) each represent a substituted or unsubstituted fused ring group having 10 to 30 ring atoms. In the anthracene derivative (A), $Ar^{101}$ and $Ar^{102}$ may represent the same substituted or unsubstituted fused ring group, or may represent different substituted or unsubstituted fused ring groups. When $Ar^{101}$ and $Ar^{102}$ are different, substitution sites may be different.

The anthracene derivative (A) is particularly preferably an anthracene derivative where $Ar^{101}$ and $Ar^{102}$ in the formula (100) represent different substituted or unsubstituted fused ring groups.

For the anthracene derivative (A), specific preferred examples of the fused ring group represented by $Ar^{101}$ and $Ar^{102}$ in the formula (100) are the same as above. Particularly, a naphthyl group, phenanthryl group, benzoanthryl group, 9,9-dimethylfluorenyl group and dibenzofuranyl group are preferable.

Anthracene Derivative (B)

The anthracene derivative (B) is an anthracene derivative where one of $Ar^{101}$ and $Ar^{102}$ in the formula (100) represents a substituted or unsubstituted aromatic hydrocarbon group having 5 to 30 ring atoms, and the other one thereof represents a substituted or unsubstituted fused ring group having 10 to 30 ring atoms.

For the anthracene derivative (B), it is preferable that $Ar^{102}$ represents one selected from a naphthyl group, phenanthryl group, benzoanthryl group, 9,9-dimethylfluorenyl group and dibenzofuranyl group, and $Ar^{101}$ represents an unsubstituted phenyl group or a phenyl group substituted by at least one of the above monocyclic groups and fused ring groups.

For the anthracene derivative (B), specific preferred examples of the monocyclic group and fused ring group are the same as above.

For the anthracene derivative (B), it is also preferable that $Ar^{102}$ represents a substituted or unsubstituted fused ring group having 10 to 30 ring atoms, and $Ar^{101}$ represents an unsubstituted phenyl group. In this case, the fused ring group is particularly preferably a phenanthryl group, 9,9-dimethylfluorenyl group, dibenzofuranyl group or benzoanthryl group.

Anthracene Derivative (C)

The anthracene derivative (C) is an anthracene derivative where $Ar^{101}$ and $Ar^{102}$ in the formula (100) each individually represent a substituted or unsubstituted monocyclic group having 5 to 30 ring atoms.

For the anthracene derivative (C), it is preferable that $Ar^{101}$ and $Ar^{102}$ each individually represent a substituted or unsubstituted phenyl group.

For the anthracene derivative (C), it is further preferable that $Ar^{101}$ represents an unsubstituted phenyl group, and $Ar^{102}$ represents the monocyclic group, or that $Ar^{101}$ and $Ar^{102}$ each independently represent a phenyl group having at least one of the above monocyclic groups and the fused ring groups as a substituent.

Specific preferred examples of the monocyclic group and the fused ring group as the substituent for $Ar^{101}$ and $Ar^{102}$ in the formula (100) are the same as above. The aromatic hydrocarbon group as the substituent is further preferably a phenyl group or biphenyl group. The fused ring group as the substituent is further preferably a naphthyl group, phenanthryl group, 9,9-dimethylfluorenyl group, dibenzofuranyl group or benzoanthryl group.

A structure of the anthracene derivative represented by the formula (100) may be a structure represented by a formula (100A) below. It should be noted that the invention is not limited to these structures of the anthracene derivative.

[Formula 86]

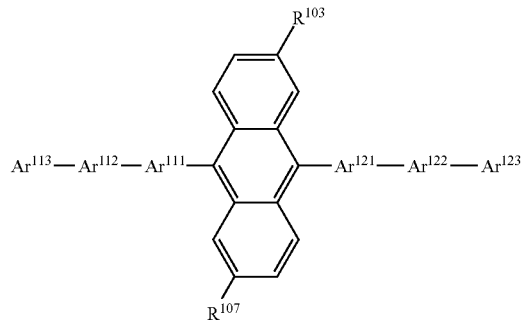

(100A)

In the formula (100A), $R^{103}$ to $R^{107}$ each independently represent a hydrogen atom, a halogen atom, a cyano group, a substituted or unsubstituted monocyclic group having 5 to 30 ring atoms, a substituted or unsubstituted fused ring group having 10 to 30 ring atoms, a chain group formed by bonding two groups selected from the group consisting of the monocyclic group and the fused ring group, a chain group formed by bonding three groups selected from the group consisting of the monocyclic group and the fused ring group, a substituted or unsubstituted alkyl group having 1 to 30 carbon atoms, a substituted or unsubstituted cycloalkyl group having 3 to 30 ring carbon atoms, a substituted or unsubstituted alkoxy group having 1 to 30 carbon atoms, a substituted or unsubstituted aralkyl group having 7 to 30 carbon atoms, a substituted or unsubstituted aryloxy having 6 to 30 ring carbon atoms, or a substituted or unsubstituted silyl group.

In the formula (100A), $Ar^{121}$ and $Ar^{111}$ each independently represent a substituted or unsubstituted monocyclic divalent residue having 5 to 30 ring atoms, or a substituted or unsubstituted fused-ring divalent residue having 10 to 30 ring atoms.

In the formula (100A), $Ar^{122}$ and $Ar^{112}$ each independently represent a single bond, a substituted or unsubstituted monocyclic divalent residue having 5 to 30 ring atoms, or a substituted or unsubstituted fused-ring divalent residue having 10 to 30 ring atoms.

In the formula (100A), $Ar^{123}$ and $Ar^{113}$ each independently represent a hydrogen atom, a substituted or unsubstituted monocyclic group having 5 to 30 ring atoms, or a substituted or unsubstituted fused ring group having 10 to 30 ring atoms.

[Formula 87]

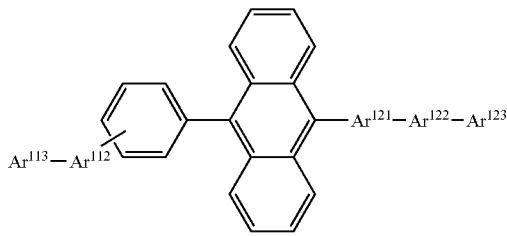

(100B)

In the formula (100B), $Ar^{121}$ represents a substituted or unsubstituted monocyclic divalent residue having 5 to 30 ring atoms, or a substituted or unsubstituted fused-ring divalent residue having 10 to 30 ring atoms.

In the formula (100B), $Ar^{122}$ and $Ar^{112}$ each independently represent a single bond, a substituted or unsubstituted monocyclic divalent residue having 5 to 30 ring atoms, or a substituted or unsubstituted fused-ring divalent residue having 10 to 30 ring atoms.

In the formula (100B), $Ar^{123}$ and $Ar^{113}$ each independently represent a hydrogen atom, a substituted or unsubstituted monocyclic group having 5 to 30 ring atoms, or a substituted or unsubstituted fused ring group having 10 to 30 ring atoms.

[Formula 88]

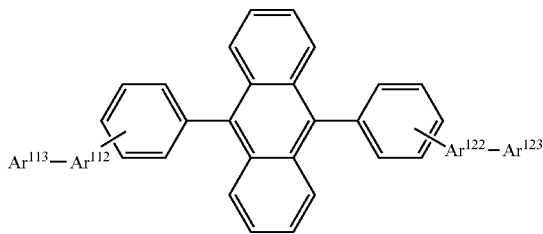

(100C)

In the formula (100C), $Ar^{122}$ represents a substituted or unsubstituted monocyclic divalent residue having 5 to 30 ring atoms, or a substituted or unsubstituted fused-ring divalent residue having 10 to 30 ring atoms.

In the formula (100C), $Ar^{112}$ represents a single bond, a substituted or unsubstituted monocyclic divalent residue having 5 to 30 ring atoms, or a substituted or unsubstituted fused-ring divalent residue having 10 to 30 ring atoms.

In the formula (100C), $Ar^{123}$ and $Ar^{113}$ each independently represent a hydrogen atom, a substituted or unsubstituted monocyclic group having 5 to 30 ring atoms, or a substituted or unsubstituted fused ring group having 10 to 30 ring atoms.

[Formula 89]

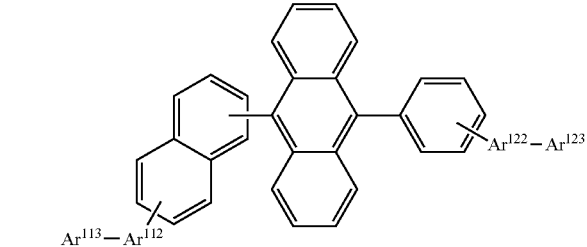

(100D)

In the formula (100D), $Ar^{122}$ represents a substituted or unsubstituted monocyclic divalent residue having 5 to 30 ring atoms, or a substituted or unsubstituted fused-ring divalent residue having 10 to 30 ring atoms.

In the formula (100D), $Ar^{112}$ represents a single bond, a substituted or unsubstituted monocyclic divalent residue having 5 to 30 ring atoms, or a substituted or unsubstituted fused-ring divalent residue having 10 to 30 ring atoms.

In the formula (100D), $Ar^{123}$ and $Ar^{113}$ each independently represent a hydrogen atom, a substituted or unsubstituted monocyclic group having 5 to 30 ring atoms, or a substituted or unsubstituted fused ring group having 10 to 30 ring atoms.

[Formula 90]

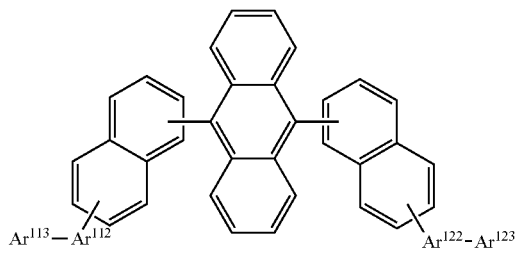

(100E)

In the formula (100E), $Ar^{122}$ and $Ar^{112}$ each independently represent a single bond, a substituted or unsubstituted monocyclic divalent residue having 5 to 30 ring atoms, or a substituted or unsubstituted fused-ring divalent residue having 10 to 30 ring atoms.

In the formula (100E), $Ar^{123}$ and $Ar^{113}$ each independently represent a hydrogen atom, a substituted or unsubstituted monocyclic group having 5 to 30 ring atoms, or a substituted or unsubstituted fused ring group having 10 to 30 ring atoms.

Preferred examples of the substituents meant by "substituted or unsubstituted" for $Ar^{111}$ to $Ar^{113}$ and $Ar^{121}$ to $Ar^{123}$ in the formulae (100A) to (100E) include a monocyclic group, fused ring group, alkyl group, cycloalkyl group, silyl group, alkoxy group, cyano group and halogen atom (in particular, fluorine). A monocyclic group and a fused ring group are particularly preferable, and specific preferred substituents are the same as the groups for the formula (100) as well as the above groups.

Examples of a material usable in the emitting layer along with the compound of the first exemplary embodiment, other than the material represented by the formula (100), include a fused polycyclic aromatic compound, a derivative of a fused polycyclic aromatic compound, an organic metal complex, a triaryl benzofluorene compound, a styryl benzofluorene compound, a stilbene derivative, a coumarin derivative, a pyrane derivative, an oxazone derivative, a benzothiazole derivative, a benzoxazole derivative, a benzimidazole derivative, a pyrazine derivative, a cinnamic acid derivative, a diketopyrolopyrrol derivative, an acridone derivative, and a quinacridone derivative. Examples of the fused polycyclic aromatic compound include naphthalene, phenanthrene, rubrenen, anthracene, tetracene, pyrene, perylene, chrysene, decacyclene, coronene, tetraphenylcyclopentadiene, pentaphenylcyclopentadiene, fluorene and spirofluorene. Examples of the organic metal complex include tris(8-quinolinolate)aluminum. The above materials usable with the amine compound of the first exemplary embodiment are not exclusive.

Substrate

A substrate is used as a support for the electroluminescence device. Examples of the substrate include a glass substrate, quartz substrate and plastic substrate. A flexible substrate is also usable. The flexible substrate, which is a substrate that is bendable (flexible), may be a plastic substrate of polycarbonate, polyarylate, polyethersulfone, polypropylene, polyester, polyvinyl fluoride or polyvinyl chloride. In addition, an inorganic vapor deposition film is also usable.

Anode

Metal, alloy, an electrically conductive compound and a mixture thereof, which have a large work function, specifically, of 4.0 eV or more, is preferably usable as the anode formed on the substrate. Specific examples of the material for the anode include indium tin oxide (ITO), indium tin oxide containing silicon or silicon oxide, indium zinc oxide, tungsten oxide, indium oxide containing zinc oxide and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), and nitrides of a metal material (e.g., titanium nitride) are usable.

The above materials are typically deposited to be a film by sputtering. For instance, indium zinc oxide can be deposited to be a film by sputtering using a target that is obtained by adding zinc oxide in an amount from 1 mass % to 10 mass % to indium oxide. Moreover, for instance, indium oxide containing tungsten oxide and zinc oxide can be deposited to be a film by sputtering using a target that is obtained by adding tungsten oxide in an amount from 0.5 mass % to 5 mass % and zinc oxide in an amount from 0.1 mass % to 1 mass % to indium oxide. In addition, vapor deposition, coating, ink jet printing, spin coating and the like may be used for forming a film.

Of EL layers formed on the anode, a hole injecting layer formed adjacent to the anode is formed of a composite material that facilitates injection of holes irrespective of the work function of the anode. Accordingly, a material usable as an electrode material (e.g., metal, alloy, an electrically conductive compound, a mixture thereof, and elements belonging to Groups 1 and 2 of the periodic table of the elements) is usable as the material for the anode.

The elements belonging to Groups 1 and 2 of the periodic table of the elements, which are materials having a small work function, namely, an alkali metal such as lithium (Li) and cesium (Cs) and an alkaline earth metal such as magnesium (Mg), calcium (Ca) and strontium (Sr), an alloy thereof (e.g., MgAg, AlLi), a rare earth metal such as europium (Eu) and ytterbium (Yb), and an alloy thereof are also usable as the material for the anode. When the anode is formed of the alkali metal, alkaline earth metal or alloy thereof, vapor deposition and sputtering are usable. Further, when the anode is formed of silver paste and the like, coating, ink jet printing and the like are usable.

Hole Injecting Layer

A hole injecting layer is a layer containing a highly hole-injectable substance. Examples of the highly hole-injectable substance include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

In addition, the highly hole-injectable substance may also be an aromatic amine compound (i.e., a low-molecular organic compound), examples of which include 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl(abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1).

Moreover, a high-molecular compound (e.g., an oligomer, dendrimer and polymer) is also usable as the highly hole-injectable substance. Examples of the high-molecular compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamido] (abbreviation: PTPDMA), and poly[N,N'-bis(4-butylphenyl)-N,N'-bis(phenyl)benzidine] (abbreviation: Poly-TPD). Furthermore, examples of the high-molecular compound include a high-molecular compound added with an acid such as poly(3,4-ethylene dioxythiophene)/poly(styrene sulfonic acid) (PEDOT/PSS), and polyaniline/poly(styrene sulfonic acid) (PAni/PSS).

Hole Transporting Layer

A hole transporting layer is a layer containing a highly hole-transportable substance. An aromatic amine compound, carbazole derivative, anthracene derivative and the like are usable for the hole transporting layer. Specific examples of a material for the hole transporting layer include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ cm$^2$/Vs or more.

A carbazole derivative such as CBP, CzPA and PCzPA and an anthracene derivative such as t-BuDNA, DNA, DPAnth are usable for the hole transporting layer. Moreover, a high-molecular compound such as poly(N-vinylcarbazole) (abbreviation: PVK) and poly(4-vinyltriphenylamine) (abbreviation: PVTPA) is also usable.

However, any substance having a hole transporting performance higher than an electron transporting performance may be used instead of the above substances. A highly hole-transportable substance may be provided by a single layer or a laminated layer of two layers or more formed of the above substance(s).

Electron Transporting Layer

An electron transporting layer is a layer containing a highly electron-transportable substance. As the electron transporting layer, 1) a metal complex such as an aluminum complex, beryllium complex and zinc complex, 2) heteroaromatic compound such as an imidazole derivative, benzimidazole derivative, azine derivative, carbazole derivative, and phenanthroline derivative, and 3) a high-molecular compound are usable. Specifically, as a low-molecular organic compound, a metal complex such as Alq, tris(4-methyl-8-quinolinolato)aluminum (abbreviation: Almq$_3$), bis(10-hydroxybenzo[h]quinolinato)beryllium (abbreviation: BeBq$_2$), BAlq, Znq, ZnPBO and ZnBTZ are usable.

In addition to the metal complex, a heteroaromatic compound such as 2-(4-biphenyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenyl)-1,2,4-triazole (abbreviation: TAZ), 3-(4-tert-butylphenyl)-4-(4-ethylphenyl)-5-(4-biphenyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs) are usable. The above-described substances mostly have an electron mobility of $10^{-6}$ cm$^2$/Vs or more. However, any substance having an electron transporting performance higher than a hole transporting performance may be used for the electron transporting layer instead of the above substances. The electron transporting layer may be provided by a single layer or a laminated layer of two layers or more formed of the above substance(s).

Moreover, a high-molecular compound is also usable for the electron transporting layer. For instance, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)](abbreviation: PF-BPy) and the like are usable.

Electron Injecting Layer

An electron injecting layer is a layer containing a highly electron-injectable substance. Examples of a material for the electron injecting layer include an alkali metal, alkaline earth metal and a compound thereof, examples of which include lithium (Li), cesium (Cs), calcium (Ca), lithium fluoride (LiF), cesium fluoride (CsF), calcium fluoride (CaF2), and lithium oxide (LiOx). In addition, a compound containing an alkali metal, alkaline earth metal and a compound thereof in the electron transportable substance, specifically, a compound containing magnesium (Mg) in Alq and the like may be used. With this compound, electrons can be more efficiently injected from the cathode.

Alternatively, a composite material provided by mixing an organic compound with an electron donor may be used for the electron injecting layer. The composite material exhibits excellent electron injecting performance and electron transporting performance since the electron donor generates electrons in the organic compound. In this arrangement, the organic compound is preferably a material exhibiting an excellent transporting performance of the generated electrons. Specifically, for instance, the above-described substance for the electron transporting layer (e.g., the metal complex and heteroaromatic compound) is usable. The electron donor may be any substance exhibiting an electron donating performace to the organic compound. Specifically, an alkali metal, alkaline earth metal and a rare earth metal are preferable, examples of which include lithium, cesium, magnesium, calcium, erbium and ytterbium. Moreover, an alkali metal oxide and alkaline earth metal oxide are preferable, examples of which include lithium oxide, calcium oxide, and barium oxide. Further, Lewis base such as magnesium oxide is also usable. Furthermore, tetrathiafulvalene (abbreviation: TTF) is also usable.

Cathode

Metal, alloy, an electrically conductive compound, a mixture thereof and the like, which have a small work function, specifically, of 3.8 eV or less, is preferably usable as a material for the cathode. Specific examples of the material for the cathode include the elements belonging to Groups 1 and 2 of the periodic table of the elements, namely, an alkali metal such as lithium (Li) and cesium (Cs) and an alkaline earth metal such as magnesium (Mg), calcium (Ca) and strontium (Sr), an alloy thereof (e.g., MgAg, AlLi), a rare earth metal such as europium (Eu) and ytterbium (Yb), and alloy thereof.

When the cathode is formed of the alkali metal, alkaline earth metal or alloy thereof, vapor deposition and sputtering are usable. Moreover, when the anode is formed of silver paste and the like, coating, ink jet printing and the like are usable.

By providing an electron injecting layer, various conductive materials such as Al, Ag, ITO, graphene and indium tin oxide containing silicon or silicon oxide are usable for forming the cathode irrespective of the magnitude of the work function. The conductive materials can be deposited to be a film by sputtering, ink jet printing, spin coating and the like.

Method of Forming Layers in Organic EL Device

The method of forming each of the layers in the organic EL device is not particularly limited. Conventionally known methods such as vacuum deposition and spin coating may be employed for forming the layers. The organic layer in the organic EL device may be formed by any one of known coating methods such as vacuum deposition, molecular beam epitaxy (MBE method), and coating methods using a solution such as a dipping, spin coating, casting, bar coating, roll coating and ink jet printing. In particular, the emitting layer of the first exemplary embodiment is further favorably formed by any one of the above coating methods.

Thicknesses of Layers in Organic EL Device

A film thickness of the emitting layer is preferably in a range of 5 nm to 50 nm, more preferably in a range of 7 nm to 50 nm and most preferably in a range of 10 nm to 50 nm. When the emitting layer has a thickness of 5 nm or more, the emitting layer is easily formable and chromaticity is easily adjustable. When the emitting layer has a thickness of 50 nm or less, an increase in the drive voltage is suppressible.

Thicknesses of other organic layer(s) are not particularly limited, but are preferably in a typical range from several nm to 1 μm. When the thicknesses fall within the above range, defects such as pin holes due to an excessively thinned film can be prevented, and an increase in the drive voltage due to an excessively thickened film can be suppressed to prevent deterioration of the efficiency.

Electronic Apparatus

The organic EL device of the first exemplary embodiment is favorably usable for electronic apparatuses such as a display unit and a light-emitting unit. Examples of the display unit include a television, a mobile phone and a personal computer. Examples of the light-emitting unit include an illuminator and a vehicle light.

Second Exemplary Embodiment

A compound of a second exemplary embodiment is structurally different from the compound of the first exemplary embodiment. The second exemplary embodiment is the same as the first exemplary embodiment in terms of the other aspects. For instance, similarly to the compound of the first exemplary embodiment, the compound of the second exemplary embodiment is also usable for an organic EL device as an organic EL device material. The organic EL device is usable in an electronic apparatus.

The compound of the second exemplary embodiment is represented by a formula (1x) below.

[Formula 91]

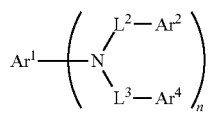 (1x)

In the structure of the compound of the second exemplary embodiment represented by the formula (1x), $Ar^1$, $Ar^2$, $L^2$, $L^3$ and n are respectively the same as $Ar^1$, $Ar^2$, $L^2$, $L^3$ and n in the first exemplary embodiment, and the preferable properties are also applicable.

The compound of the second exemplary embodiment is the same as the compound of the first exemplary embodiment except that $Ar^4$ bonded to $L^3$ is structurally different from $Ar^3$ bonded to $L^3$.

$Ar^4$ in the formula (1x) is represented by a formula (1a) or (11a) below.

[Formula 92]

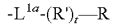 (1a)

[Formula 93]

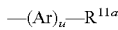 (11a)

The formulae (1a) and (11a) of the second exemplary embodiment are respectively the same as the formulae (1a) and (11a) of the first exemplary embodiment, and the preferable properties are also applicable. In the second exemplary embodiment, for instance, a group represented by the formula (1a) is similarly preferably represented by a formula (1b) or (1c) below.

[Formula 94]

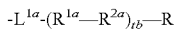 (1b)

[Formula 95]

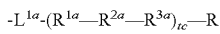 (1c)

The formulae (1b) and (1c) of the second exemplary embodiment are respectively the same as the formulae (1b) and (1c) of the first exemplary embodiment, and the preferable properties are also applicable.

In the second exemplary embodiment, for instance, a group represented by the formula (11a) is similarly preferably represented by a formula (11b) or (11c) below.

[Formula 96]

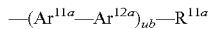 (11b)

[Formula 97]

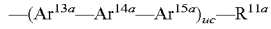 (11c)

The formulae (11b) and (11c) of the second exemplary embodiment are respectively the same as the formulae (11b) and (11c) of the first exemplary embodiment, and the preferable properties are also applicable.

In the second exemplary embodiment, $Ar^1$ in the formula (1x) preferably has a skeleton represented by any one selected from the group consisting of the formulae (1-1) to (1-22) of the first exemplary embodiment.

In the second exemplary embodiment, n in the formula (1x) is 2, $Ar^1$ preferably has a skeleton represented by any one selected from the group consisting of the formulae (1-31) to (1-34) of the first exemplary embodiment, and $Ar^1$ preferably has a skeleton represented by the formula (1-31). In the second exemplary embodiment, $X^{11}$ and $X^{12}$ in the formulae (1-1) to (1-22) and (1-31) to (1-34) are similarly preferably represented by the formula (2a) of the first exemplary embodiment.

Third Exemplary Embodiment

A compound of a third exemplary embodiment is structurally different from the compound of the first exemplary embodiment. The third exemplary embodiment is the same as the first exemplary embodiment in terms of the other aspects. For instance, similarly to the compound of the first exemplary embodiment, the compound of the third exemplary embodiment is also usable for an organic EL device as an organic EL device material. The organic EL device is usable in an electronic apparatus.

The compound of the third exemplary embodiment is represented by a formula (1y) below.

[Formula 98]

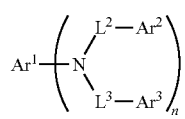 (1y)

In the structure of the compound of the third exemplary embodiment represented by the formula (1y), $Ar^2$, $L^2$, $L^3$ and n are respectively the same as $Ar^2$, $L^2$, $L^3$ and n in the first exemplary embodiment, and the preferable properties are also applicable.

$Ar^1$ is represented by a formula (2) below.

[Formula 99]

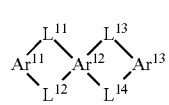 (2)

In the formula (23), $Ar^{11}$, $Ar^{12}$ and $Ar^{13}$ each independently represent a substituted or unsubstituted aromatic hydrocarbon group having 6 to 30 ring carbon atoms. One of L and $L^{12}$ represents a single bond for bonding $Ar^{11}$ and Ar$^{12}$, and the other one thereof represents a linking group represented by a formula (2f) below. One of L$^{13}$ and L$^{14}$ represents a single bond for bonding Ar$^{12}$ and Ar$^{13}$, and the other one thereof represents a linking group represented by the formula (2f) below.

[Formula 100]

(2f)

In the formula (2f), R$^{21}$ and R$^{22}$ each independently represent a substituted or unsubstituted alkylsilyl group having 3 to 30 carbon atoms, or a substituted or unsubstituted arylsilyl group having 6 to 60 ring carbon atoms.

The compound of the third exemplary embodiment is the same as the compound of the first exemplary embodiment except that Ar$^1$ represented by the formula (2), unlike Ar$^1$ of the compound of the first exemplary embodiment, has a linking group represented by the formula (2f).

Modifications of Embodiment(s)

It should be noted that the invention is not limited to the above exemplary embodiment but may include any modification and improvement as long as such modification and improvement are compatible with the invention.

The emitting layer is not limited to a single layer, but may be provided as laminate by a plurality of emitting layers. When the organic EL device includes a plurality of emitting layers, it is only required that at least one of the emitting layers includes the compound represented by the formula (1) or the formula (21). The others of the emitting layers may be a fluorescent emitting layer or a phosphorescent emitting layer.

When the organic EL device includes the plurality of emitting layers, the plurality of emitting layers may be adjacent to each other or a so-called tandem organic EL device in which a plurality of emitting units are laminated through an intermediate layer.

In the invention, the emitting layer may also preferably contain an assistance substance for assisting injection of charges.

When the emitting layer is formed of a host material that exhibits a wide energy gap, a difference in ionization potential (Ip) between the host material and the hole injecting/transporting layer etc. becomes so large that injection of the holes into the emitting layer becomes difficult, which may cause a rise in a driving voltage required for providing sufficient luminance.

In the above instance, introducing a hole-injectable or hole-transportable assistance substance for assisting injection of charges in the emitting layer can contribute to facilitation of the injection of the holes into the emitting layer and to reduction of the driving voltage.

As the assistance substance for assisting the injection of charges, for instance, a general hole injecting material, a general hole transporting material or the like can be used.

Specific examples of the assistance substance for assisting the injection of charges include a triazole derivative, oxadiazole derivative, imidazole derivative, polyarylalkane derivative, pyrazoline derivative, pyrazolone derivative, phenylene dibenzofluorene compound, aryl benzofluorene compound, amino-substituted chalcone derivative, oxazole derivative, fluorenone derivative, hydrazone derivative, stilbene derivative, silazane derivative, polysilane copolymer, aniline copolymer, and conductive high-molecular oligomer (in particular, thiophene oligomer).

The hole injecting material, which is exemplified by the above, is preferably any one of a porphyrin compound, aromatic tertiary amine compound and styryl amine compound, among which an aromatic tertiary amine compound is particularly preferable.

In addition, for instance, 4,4'-bis(N-(1-naphthyl)-N-phenylamino)biphenyl (hereinafter, abbreviated as NPD) having two fused aromatic rings in a molecule, or 4,4',4"-tris(N-(3-methylphenyl)-N-phenylamino)triphenylamine (hereinafter, abbreviated as MTDATA) in which three triphenylamine units are bonded in a starburst may also be used.

In addition, for instance, a hexaazatriphenylene derivative is also favorably usable as the hole injecting material.

In addition, inorganic compounds such as p-type Si and p-type SiC are also usable as the hole-injecting material.

In the above exemplary embodiments, the compound according to the invention is used as the dopant material in the emitting layer. However, the compound according to the invention is usable not only in the emitting layer but also in the other organic layers such as the hole injecting layer, the hole transporting layer, the electron injecting layer and the electron transporting layer.

EXAMPLES

Next, the invention will be described in further detail with reference to Example(s) and Comparative Example(s). However, the invention is not limited by the description of Example(s).

Synthesis Example 1: Synthesis of Compound 1

[Formula 101]

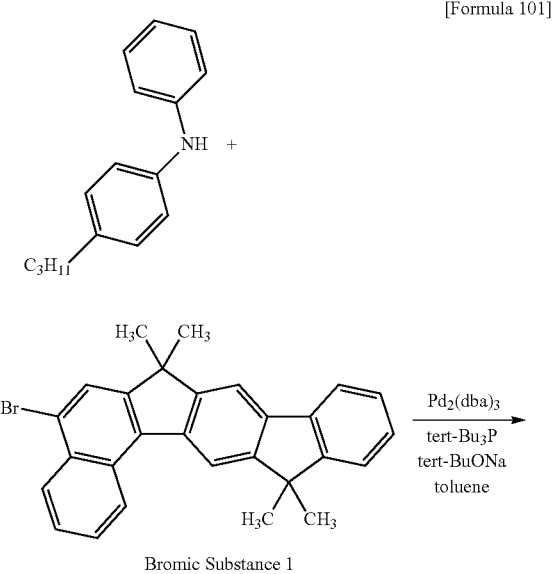

Bromic Substance 1

-continued

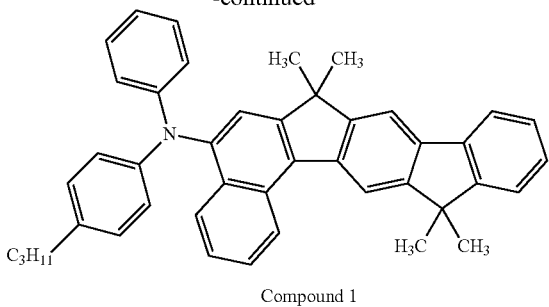

Compound 1

Under an argon gas stream, a bromic substance 1 (1.1 g), phenyl(4-pentylphenyl)amine (0.65 g), Pd$_2$(dba)$_3$ (140 mg), tert-Bu$_3$P (2.746M toluene solution) (100 μl), and tert-BuONa (0.75 g) were added in a dehydrated toluene solution (100 ml), and agitated at 120 degrees C. for five hours. After the mixture was cooled down, a resulting precipitation was washed with toluene, methanol, water, acetone and acetic ether to obtain a partially purified product. The partially purified product was purified by silica-gel chromatography and then further purified by re-precipitation. Toluene was used as an eluent for the silica-gel chromatography. A mixed solvent of toluene and methanol was used for the re-precipitation. As a result of the purification, 1 g of a compound 1 was obtained. It should be noted that the compound was identified by a field desorption mass spectrometry (FD-MS) analysis.

FDMS, calcd for C$_{45}$H$_{43}$N=597, found m/z=597(M$^+$).

Synthesis Example 2: Synthesis of Compound 2

[Formula 102]

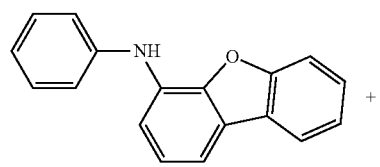

Amine Compound 2

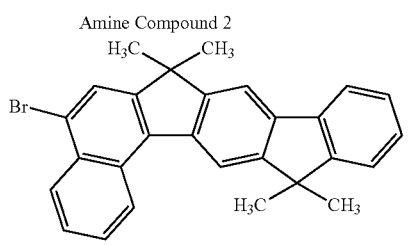

Bromic Substance 1

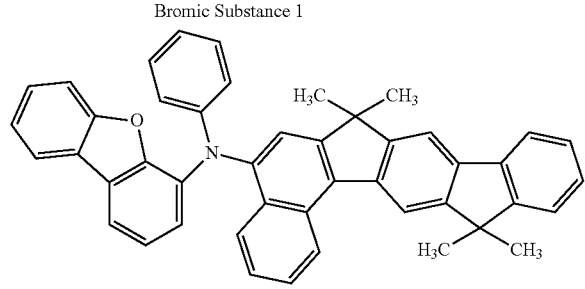

Compound 2

A synthesis example 2 was the same as the synthesis example 1 except that an amine compound 2 (0.68 g) was used in place of the phenyl(4-pentylphenyl)amine (0.65 g) used in the synthesis example 1. As a result of the synthesis, a compound 2 was obtained.

FDMS, calcd for C$_{46}$H$_{35}$NO=617, found m/z=617(M$^+$).

Synthesis Example 3: Synthesis of Compound 3

[Formula 103]

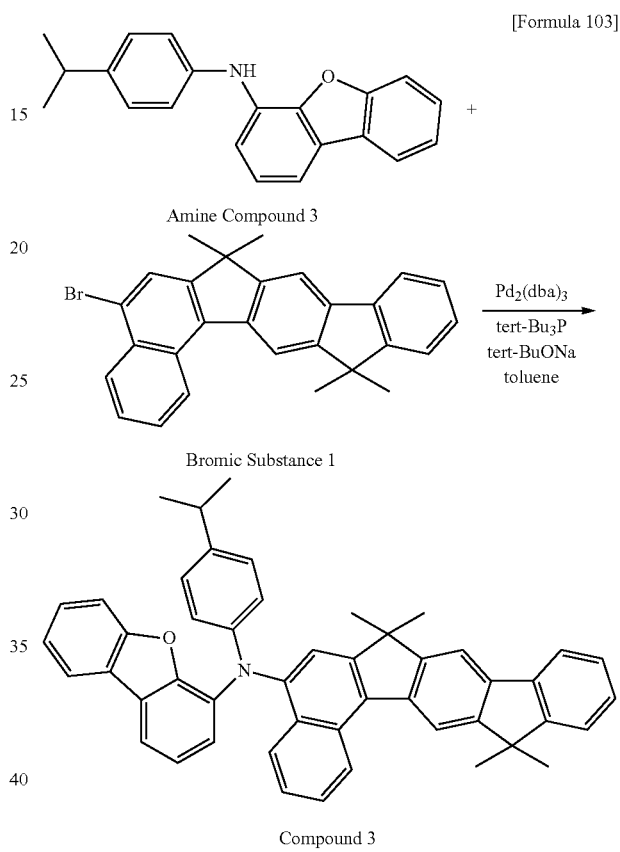

Compound 3

A synthesis example 3 was the same as the synthesis example 1 except that an amine compound 3 (0.82 g) was used in place of the phenyl(4-pentylphenyl)amine (0.65 g) used in the synthesis example 1. As a result of the synthesis, a compound 3 was obtained.

FDMS, calcd for C$_{49}$H$_{41}$NO=659, found m/z=659(M+).

Synthesis Example 4: Synthesis of Compound 4

[Formula 104]

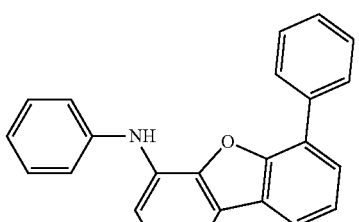

Amine Compound 4

-continued

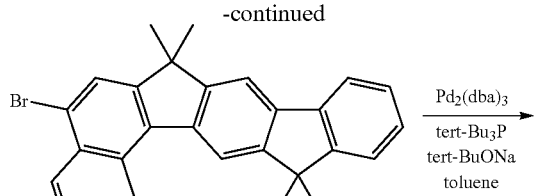

Bromic Substance 1

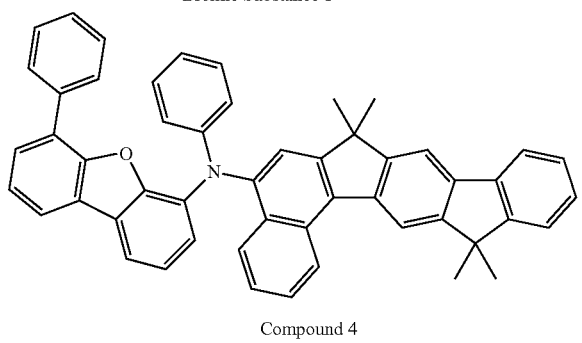

Compound 4

A synthesis example 4 was the same as the synthesis example 1 except that an amine compound 4 (0.91 g) was used in place of the phenyl(4-pentylphenyl)amine (0.65 g) used in the synthesis example 1. As a result of the synthesis, a compound 4 was obtained.

FDMS, calced for $C_{49}H_{41}NO=693$, found m/z=693(M+).

Synthesis Example 5: Synthesis of Compound 5

[Formula 105]

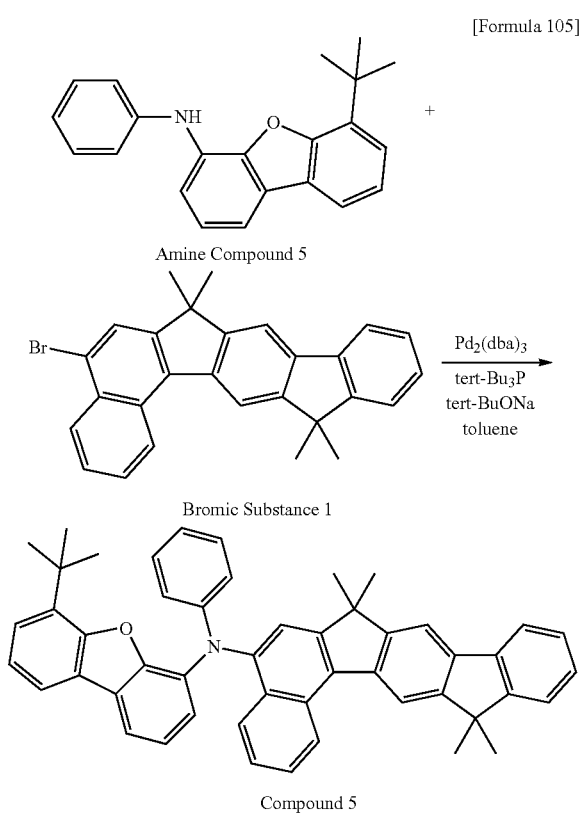

A synthesis example 5 was the same as the synthesis example 1 except that an amine compound 5 (0.86 g) was used in place of the phenyl(4-pentylphenyl)amine (0.65 g) used in the synthesis example 1. As a result of the synthesis, a compound 5 was obtained.

FDMS, calced for $C_{49}H_{41}NO=673$, found m/z=673(M+).

Example 1

A glass substrate (size: 25 mm×75 mm×1.1 mm thick) having an ITO transparent electrode line (manufactured by GEOMATEC Co., Ltd.) was ultrasonic-cleaned in isopropyl alcohol for five minutes, and then UV/ozone-cleaned for 30 minutes. A thickness of the ITO transparent electrode was 130 nm.

The cleaned glass substrate having the ITO transparent electrode line was mounted on a substrate holder of a vacuum deposition apparatus. Initially, the following compound HI-1 was vapor-deposited on a surface of the glass substrate where the ITO transparent electrode line was provided to cover the ITO transparent electrode line, thereby forming a 5-nm-thick HI-1 film. A hole injecting layer was thus provided.

The following compound HT-1 was then vapor-deposited as a first hole transporting material on the hole injecting layer to form an 80-nm-thick HT-1 film. A first hole transporting layer was thus provided.

The following compound HT-2 was then vapor-deposited on the first hole transporting layer to form a 15-nm-thick HT-2 film. A second hole transporting layer was thus provided.

A compound BH-1 (a host material) and the compound 2 (a dopant material) were co-deposited on the second hole transporting layer to form a 25-nm-thick co-deposited film. The concentration of the compound 2 in the co-deposited film was 5.0 mass %. This co-deposited film serves as an emitting layer.

The following compound ET-1 was then vapor-deposited on the emitting layer to form a 20-nm-thick ET-1 film. A first electron transporting layer was thus provided.

The following compound ET-2 was then vapor-deposited on the first electron transporting layer to form a 5-nm-thick ET-2 film. A second electron transporting layer was thus provided.

LiF was then vapor-deposited on the second electron transporting layer to form a 1-nm-thick LiF film. An electron injecting electrode (a cathode) was thus provided.

A metal Al film was then vapor-deposited on the LiF film to form an 80-nm-thick metal Al film. A metal Al cathode was thus provided.

A device arrangement of the organic EL device of Example 1 is roughly shown as follows.

ITO (130)/HI-1 (5)/HT-1 (80)/HT-2 (15)/BH-1: compound 2 (25.95%: 5%)/ET-1 (20)/ET-2 (5)/LiF (1)/Al (80)

Numerals in parentheses each represent a film thickness (unit: nm). The numerals represented by percentage in parentheses each indicate a ratio (mass %) of the compound in the layer. The same applies below.

The compounds used to manufacture the organic EL device are shown below.

[Formula 106]
HI-1
HT-1
[Formula 107]
BH-1
ET-1
ET-2
[Formula 108]
Compound 2
Compound 3
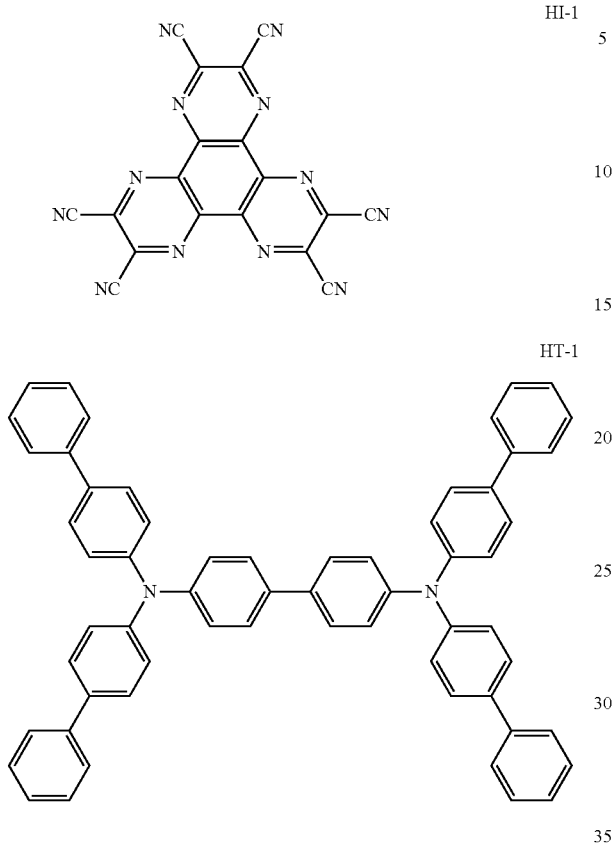
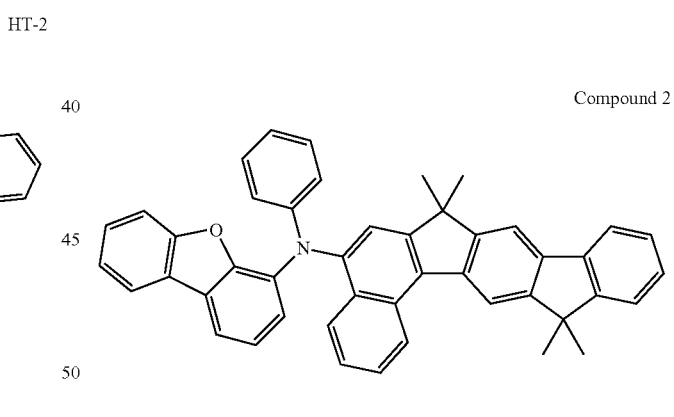
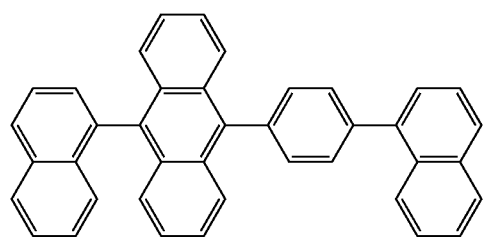
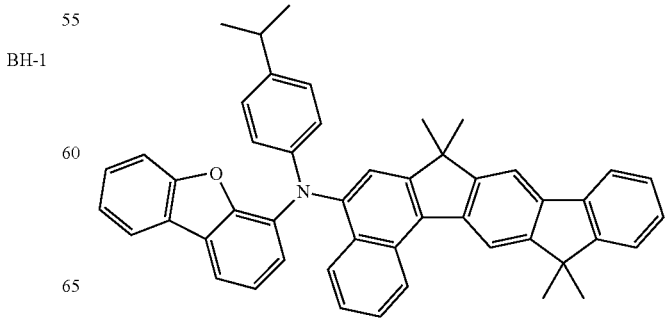

-continued

Compound 4

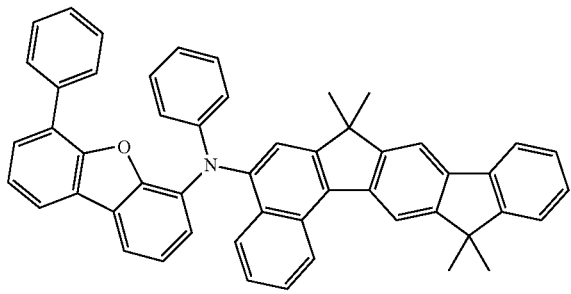

[Formula 109]

Compound 5

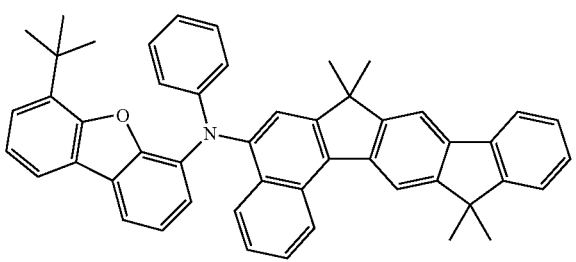

Comparative Compound

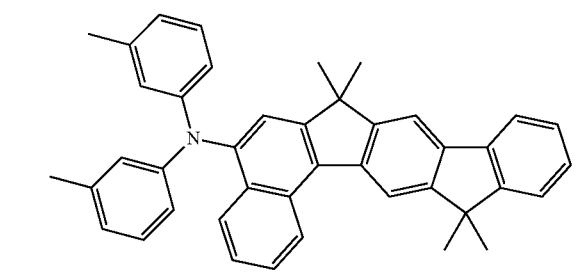

Example 2

An organic EL device of Example 2 was manufactured in the same manner as that of Example 1 except that the compound 3 was used in place of the compound 2 of Example 1.

A device arrangement of the organic EL device of Example 2 is roughly shown as follows.

ITO (130)/HI-1 (5)/HT-1 (80)/HT-2 (15)/BH-1: compound 3 (25.95%: 5%)/ET-1 (20)/ET-2 (5)/LiF (1)/Al (80)

Example 3

An organic EL device of Example 3 was manufactured in the same manner as that of Example 1 except that the compound 4 was used in place of the compound 2 of Example 1.

A device arrangement of the organic EL device of Example 3 is roughly shown as follows.

ITO (130)/HI-1 (5)/HT-1 (80)/HT-2 (15)/BH-1: compound 4 (25.95%: 5%)/ET-1 (20)/ET-2 (5)/LiF (1)/Al (80)

Example 4

An organic EL device of Example 4 was manufactured in the same manner as that of Example 1 except that the compound 5 was used in place of the compound 2 of Example 1.

A device arrangement of the organic EL device of Example 4 is roughly shown as follows.

ITO (130)/HI-1 (5)/HT-1 (80)/HT-2 (15)/BH-1: compound 5 (25.95%: 5%)/ET-1 (20)/ET-2 (5)/LiF (1)/Al (80)

Comparative Example 1

An organic EL device of Comparative Example 1 was manufactured in the same manner as that of Example 1 except that the comparative compound was used in place of the compound 2 of Example 1.

A device arrangement of the organic EL device of Comparative Example 1 is roughly shown as follows.

ITO (130)/HI-1 (5)/HT-1 (80)/HT-2 (15)/BH-1: comparative compound (25.95%: 5%)/ET-1 (20)/ET-2 (5)/LiF (1)/Al (80)

Evaluation of Organic EL Devices

Drive Voltage

Voltage was applied between the ITO transparent electrode and the metal Al cathode such that the current density was 10 mA/cm$^2$, and the voltage (unit: V) at the time was measured.

Main Peak Wavelength $\lambda_p$

Voltage was applied to each of the manufactured organic EL devices such that the current density was 10 mA/cm$^2$, and a spectral radiance spectrum was measured using a spectroradiometer CS-1000 (manufactured by Konica Minolta, Inc.). A main peak wavelength $\lambda_p$ was calculated based on the obtained spectral-radiance spectrum. It should be noted that the main peak wavelength λp was a peak wavelength where a luminous intensity is maximized according to the spectral-radiance spectrum. The results are shown in Table 1.

Lifetime LT80

Each of the manufactured organic EL devices was driven by applying voltage thereto such that a current density was 50 mA/cm$^2$, and time elapsed before the luminescence falls to 80% of the initial luminescence was measured. The time was referred to as lifetime LT80. The results are shown in Table 1.

TABLE 1

| | Dopant Material | Voltage (V) | Main Peak Wavelength $\lambda_p$ (nm) | LT80 (h) |
|---|---|---|---|---|
| Ex. 1 | Compound 2 | 3.6 | 453 | 160 |
| Ex. 2 | Compound 3 | 3.6 | 456 | 170 |
| Ex. 3 | Compound 4 | 3.6 | 452 | 160 |
| Ex. 4 | Compound 5 | 3.6 | 451 | 155 |
| Comp. 1 | Comparative Compound | 3.6 | 460 | 150 |

The organic EL devices of Examples 1 to 4, which respectively used the compounds 2 to 5 as the dopant material, each had a main peak wavelength appearing on a short-wavelength side, a high color purity, and a long lifetime LT80, as compared with the organic EL device of Comparative Example 1 using the comparative compound.

The invention claimed is:

1. A compound represented by a formula (1) below, (1)

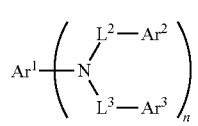

where:

n in the formula (1) is 2, and

Ar¹ in the formula (1) comprises a skeleton represented by any one selected from the group consisting of formulae (1-31) to (1-34) below,

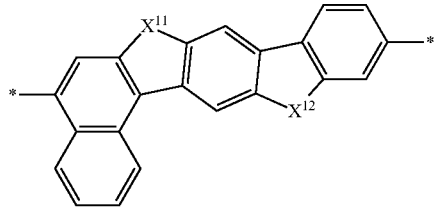
(1-31)

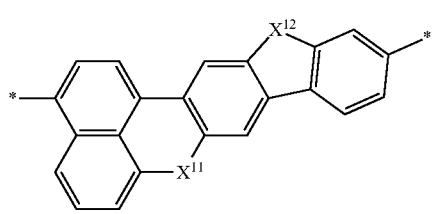
(1-32)

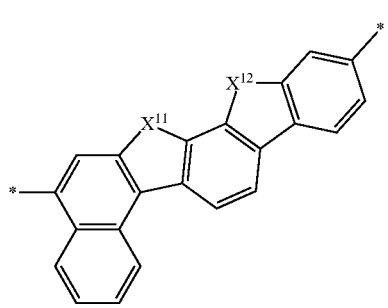
(1-33)

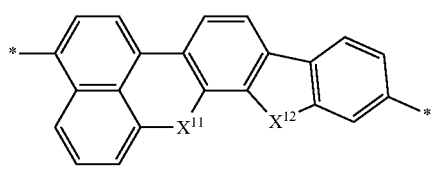
(1-34)

where: $X^{11}$ and $X^{12}$ each independently represent a linking group represented by any one of formulae (2a) to (2e) below; and at least one of * represents a position at which the skeleton is bonded to a nitrogen atom in the formula (1),

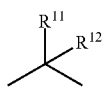
(2a)

(2b)

(2c)

(2d)

(2e)

where $R^{11}$ to $R^{15}$ each independently represent a hydrogen atom, a substituted or unsubstituted alkyl group having 1 to 30 carbon atoms, a substituted or unsubstituted aromatic hydrocarbon group having 6 to 30 ring carbon atoms, or a substituted or unsubstituted heterocyclic group having 5 to 30 ring atoms;

$L^2$ and $L^3$ in the formula (1) each independently represent a single bond or a linking group, the linking group being a substituted or unsubstituted aromatic hydrocarbon group having 6 to 30 ring carbon atoms, a substituted or unsubstituted heterocyclic group having 5 to 30 ring atoms, a multiple linking group formed by bonding two groups selected from the group consisting of the aromatic hydrocarbon group, a multiple linking group formed by bonding three groups selected from the group consisting of the aromatic hydrocarbon group, a multiple linking group formed by bonding two groups selected from the group consisting of the heterocyclic group, a multiple linking group formed by bonding three groups selected from the group consisting of the heterocyclic group, a multiple linking group formed by bonding two groups selected from the group consisting of the aromatic hydrocarbon group and the heterocyclic group, or a multiple linking group formed by bonding three groups selected from the group consisting of the aromatic hydrocarbon group and the heterocyclic group;

the aromatic hydrocarbon group or groups and the heterocyclic group or groups in the multiple linking group are mutually the same or different, and adjacent ones of the groups in the multiple linking group are optionally bonded to each other to form a ring or not bonded;

Ar² in the formula (1) represents a substituted or unsubstituted aromatic hydrocarbon group having 6 to 30 ring carbon atoms, or a substituted or unsubstituted heterocyclic group having 5 to 30 ring atoms; and Ar³ in the formula (1) is represented by a formula (3) below,

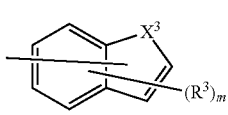
(3)

where: $X^3$ represents an oxygen atom or a sulfur atom; m is 5; $R^3$ represents a substituent bonded to a carbon atom of a ring in a structure represented by the formula (3), $R^3$ each independently representing a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, a substituted or unsubstituted arylthio group having 6 to 30 ring carbon atoms, a substituted or unsubstituted aromatic hydrocarbon group having 6 to 30 ring carbon atoms, or a substituted or unsubstituted heterocyclic group having 5 to 30 ring atoms, adjacent ones of $R^3$ optionally forming a ring or not; and a bond from the structure represented by the formula (3) is bonded to $L^3$ in the formula (1).

2. The compound according to claim 1, wherein $Ar^1$ comprises a skeleton represented by the formula (1-31).

3. The compound according to claim 1, wherein $X^{11}$ and $X^{12}$ are represented by the formula (2a).

4. The compound according to claim 1, wherein $L^3$ represents a single bond.

5. The compound according to claim 1, wherein $Ar^3$ is represented by a formula (4) below,

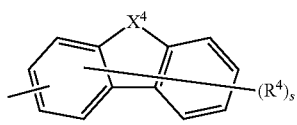

(4)

where: $X^4$ represents an oxygen atom or a sulfur atom; s is 7; $R^4$ represents a substituent bonded to a carbon atom of a ring in a structure represented by the formula (4), $R^4$ each independently representing the same as $R^3$ in the formula (3), adjacent ones of $R^4$ optionally forming a ring or not; and a bond from the structure represented by the formula (4) is bonded to $L^3$ in the formula (1).

6. The compound according to claim 5, wherein $Ar^3$ is represented by a formula (4-1) below,

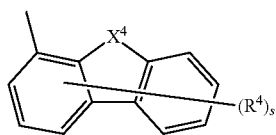

(4-1)

where: $X^4$, s and $R^4$ represent the same as $X^4$, s and $R^4$ in the formula (4), respectively; and a bond from a structure represented by the formula (4-1) is bonded to $L^3$ in the formula (1).

7. The compound according to claim 5, wherein $Ar^3$ is represented by a formula (4-2) below,

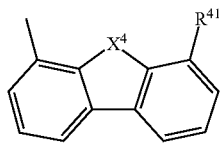

(4-2)

where: $X^4$ represents the same as $X^4$ in the formula (4); and $R^{41}$ represents a hydrogen atom, an alkyl group having 1 to 20 carbon atoms, or a substituted or unsubstituted aromatic hydrocarbon group having 1 to 30 carbon atoms; and a bond from a structure represented by the formula (4-2) is bonded to $L^3$ in the formula (1).

8. The compound according to claim 5, wherein $X^4$ represents an oxygen atom.

9. The compound according to claim 1, wherein
$R^{11}$ to $R^{15}$ in the formulae (2a) to (2e) each independently represent a substituted or unsubstituted aromatic hydrocarbon group having 6 to 30 ring carbon atoms, or a substituted or unsubstituted heterocyclic group having 5 to 30 ring atoms, $R^3$ in the formula (3) each independently represent a hydrogen atom, a halogen atom, a hydroxyl group, a cyano group, a substituted or unsubstituted arylsilyl group having 6 to 60 ring carbon atoms, a substituted or unsubstituted aryloxy group having 6 to 30 ring carbon atoms, a substituted or unsubstituted arylamino group having 6 to 60 ring carbon atoms, a substituted or unsubstituted arylthio group having 6 to 30 ring carbon atoms, a substituted or unsubstituted aromatic hydrocarbon group having 6 to 30 ring carbon atoms, a substituted or unsubstituted heterocyclic group having 5 to 30 ring atoms, or a group represented by a formula (1a) below, and at least one of a substituent of substituted $Ar^2$ and plural $R^3$ is represented by the formula (1a) below, $$-L^{1a}-(R')_t-R \qquad (1a)$$

where: $L^{1a}$ represents a single bond or a linking group, the linking group being a divalent group selected from the group consisting of a substituted or unsubstituted aromatic hydrocarbon group having 6 to 18 ring carbon atoms, and a substituted or unsubstituted heterocyclic group having 5 to 15 ring atoms; R' represents $CR^{101a}R^{102a}$; R, $R^{101a}$ and $R^{102a}$ each independently represent a hydrogen atom, a halogen atom, a hydroxyl group, a cyano group, a substituted or unsubstituted arylsilyl group having 6 to 60 ring carbon atoms, a substituted or unsubstituted aryloxy group having 6 to 30 ring carbon atoms, a substituted or unsubstituted arylamino group having 6 to 60 ring carbon atoms, a substituted or unsubstituted arylthio group having 6 to 30 ring carbon atoms, a substituted or unsubstituted aromatic hydrocarbon group having 6 to 18 ring carbon atoms, or a substituted or unsubstituted heterocyclic group having 5 to 15 ring atoms; $R^{101a}$ and $R^{102a}$ are optionally bonded to each other to form a ring or not bonded; t is an integer of 4 to 20; plural R' are mutually the same or different; adjacent ones of R' are optionally bonded to each other to form a ring or not bonded; adjacent ones of $L^{1a}$ and R' are optionally bonded to each other to form a ring or not bonded; adjacent ones of R' and R are optionally bonded to each other to form a ring or not bonded; and when the formula (1) comprises two or more groups represented by the formula (1a), the substituents represented by the formula (1a) are mutually the same or different.

10. The compound according to claim 5, wherein
$R^{11}$ to $R^{15}$ in the formulae (2a) to (2e) each independently represent a substituted or unsubstituted aromatic hydrocarbon group having 6 to 30 ring carbon atoms, or a substituted or unsubstituted heterocyclic group having 5 to 30 ring atoms, $R^4$ in the formula (4) each independently represent a hydrogen atom, a halogen atom, a hydroxyl group, a cyano group, a substituted or unsubstituted arylsilyl group having 6 to 60 ring carbon atoms, a substituted or unsubstituted aryloxy group having 6 to 30 ring carbon atoms, a substituted or unsubstituted arylamino group having 6 to 60 ring carbon atoms, a substituted or unsubstituted arylthio group having 6 to 30 ring carbon atoms, a substituted or unsubstituted aromatic hydrocarbon group having 6 to 30 ring carbon atoms, a substituted or unsubstituted heterocyclic group having 5 to 30 ring atoms, or a group represented by a formula (1a) below, and at least one of a substituent of substituted $Ar^2$ and plural $R^4$ is represented by the formula (1a) below,

$$-L^{1a}\text{-}(R')_t\text{—}R \quad (1a)$$

where: $L^{1a}$ represents a single bond or a linking group, the linking group being a divalent group selected from the group consisting of a substituted or unsubstituted aromatic hydrocarbon group having 6 to 18 ring carbon atoms, and a substituted or unsubstituted heterocyclic group having 5 to 15 ring atoms; R' represents $CR^{101a}R^{102a}$; R, $R^{101a}$ and $R^{102a}$ each independently represent a hydrogen atom, a halogen atom, a hydroxyl group, a cyano group, a substituted or unsubstituted arylsilyl group having 6 to 60 ring carbon atoms, a substituted or unsubstituted aryloxy group having 6 to 30 ring carbon atoms, a substituted or unsubstituted arylamino group having 6 to 60 ring carbon atoms, a substituted or unsubstituted arylthio group having 6 to 30 ring carbon atoms, a substituted or unsubstituted aromatic hydrocarbon group having 6 to 18 ring carbon atoms, or a substituted or unsubstituted heterocyclic group having 5 to 15 ring atoms; $R^{101a}$ and $R^{102a}$ are optionally bonded to each other to form a ring or not bonded; t is an integer of 4 to 20; plural R' are mutually the same or different; adjacent ones of R' are optionally bonded to each other to form a ring or not bonded; adjacent ones of $L^{1a}$ and R' are optionally bonded to each other to form a ring or not bonded; adjacent ones of R' and R are optionally bonded to each other to form a ring or not bonded; and when the formula (1) comprises two or more groups represented by the formula (1a), the substituents represented by the formula (1a) are mutually the same or different.

11. The compound according to claim 9, wherein the group represented by the formula (1a) is a substituent represented by a formula (1b) below,

$$-L^{1a}\text{-}(R^{1a}\text{—}R^{2a})_{tb}\text{—}R \quad (1b)$$

where: $L^{1a}$ and R represent the same as $L^{1a}$ and R in the formula (1a), respectively; $R^{1a}$ and $R^{2a}$ each independently represent the same as R' in the formula (1a); tb represents repetition of $—R^{1a}—R^{2a}—$, and is an integer of 2 to 10; adjacent ones of $R^{1a}$ and $R^{2a}$ are optionally bonded to each other to form a ring or not bonded; adjacent ones of $R^{2a}$ and R are optionally bonded to each other to form a ring or not bonded; and adjacent ones of $R^{1a}$ and $L^1$ are optionally bonded to each other to form a ring or not bonded.

12. The compound according to claim 9, wherein the group represented by the formula (1a) is a substituent represented by a formula (1c) below,

$$-L^{1a}\text{-}(R^{1a}\text{—}R^{2a}\text{—}R^{3a})_{tc}\text{—}R \quad (1c)$$

where: $L^{1a}$ and R represent the same as $L^{1a}$ and R in the formula (1a), respectively; $R^{1a}$, $R^{2a}$ and $R^{3a}$ each independently represent the same as R' in the formula (1a); tc represents repetition of $—R^{1a}—R^{2a}—R^{3a}—$, and is an integer of 2 to 6; adjacent ones of $R^{1a}$ and $R^{2a}$ are optionally bonded to each other to form a ring or not bonded; adjacent ones of $R^{2a}$ and $R^{3a}$ are optionally bonded to each other to form a ring or not bonded; adjacent ones of $R^{3a}$ and R are optionally bonded to each other to form a ring or not bonded; and adjacent ones of $R^{1a}$ and $L^1$ are optionally bonded to each other to form a ring or not bonded.

13. The compound according to claim 9, wherein R' in the formula (1a) represents a methylene group.

14. The compound according to claim 1, wherein $R^3$ in the formula (3) represents a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, a substituted or unsubstituted arylthio group having 6 to 30 ring carbon atoms, a substituted or unsubstituted aromatic hydrocarbon group having 6 to 30 ring carbon atoms, a substituted or unsubstituted heterocyclic group having 5 to 30 ring atoms, or a group represented by a formula (11a) below, and at least one of a substituent of substituted $Ar^2$ and plural $R^3$ is represented by the formula (11a) below,

$$—(Ar)_u\text{—}R^{11a} \quad (11a)$$

where: Ar represents a substituted or unsubstituted divalent aromatic hydrocarbon group having 6 to 18 ring carbon atoms, or a substituted or unsubstituted divalent heterocyclic group having 5 to 15 ring atoms; u is an integer of 3 to 20; plural Ar are mutually the same or different; adjacent ones of Ar are optionally bonded to each other to form a ring or not bonded; adjacent ones of Ar and $R^{11a}$ are optionally bonded to each other to form a ring or not bonded; and $R^{11a}$ represents a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms.

15. The compound according to claim 5, wherein $R^4$ in the formula (4) represents a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, a substituted or unsubstituted arylthio group having 6 to 30 ring carbon atoms, a substituted or unsubstituted aromatic hydrocarbon group having 6 to 30 ring carbon atoms, a substituted or unsubstituted heterocyclic group having 5 to 30 ring atoms, or a group represented by a formula (11a) below, and at least one of a substituent of substituted $Ar^2$ and plural $R^4$ is represented by the formula (11a) below,

—(Ar)$_u$—R$^{11a}$         (11a)

where: Ar represents a substituted or unsubstituted divalent aromatic hydrocarbon group having 6 to 18 ring carbon atoms, or a substituted or unsubstituted divalent heterocyclic group having 5 to 15 ring atoms; u is an integer of 3 to 20; plural Ar are mutually the same or different; adjacent ones of Ar are optionally bonded to each other to form a ring or not bonded; adjacent ones of Ar and R$^{11a}$ are optionally bonded to each other to form a ring or not bonded; and R$^{11a}$ represents a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms.

16. The compound according to claim 14, wherein the group represented by the formula (11a) is represented by a formula (11b) below,

—(Ar$^{11a}$—Ar$^{12a}$)$_{ub}$—R$^{11a}$         (11b)

where: R$^{11a}$ represents the same as R$^{11a}$ in the formula (11a); Ar$^{11a}$ and Ar$^{12a}$ each independently represent a substituted or unsubstituted divalent aromatic hydrocarbon group having 6 to 18 ring carbon atoms, or a substituted or unsubstituted divalent heterocyclic group having 5 to 15 ring atoms; and ub represents repetition of —Ar$^{11a}$—Ar$^{12a}$—, and is an integer of 2 to 10.

17. The compound according to claim 14, wherein the group represented by the formula (11a) is represented by a formula (11c) below,

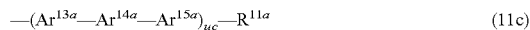

—(Ar$^{13a}$—Ar$^{14a}$—Ar$^{15a}$)$_{uc}$—R$^{11a}$         (11c)

where: R$^{11a}$ represents the same as R$^{11a}$ in the formula (11a); Ar$^{13a}$, Ar$^{14a}$ and Ar$^{15a}$ each independently represent a substituted or unsubstituted divalent aromatic hydrocarbon group having 6 to 18 ring carbon atoms, or a substituted or unsubstituted divalent heterocyclic group having 5 to 15 ring atoms; and uc represents repetition of —Ar$^{13a}$—Ar$^{14a}$—Ar$^{15a}$—, and is an integer of 2 to 6.

18. The compound according to claim 14, wherein Ar in the formula (11a) represents a structure selected from the group consisting of structures represented by formulae (Ar-1-1) to (Ar-1-23) below,

Ar-1-1

Ar-1-2

Ar-1-3

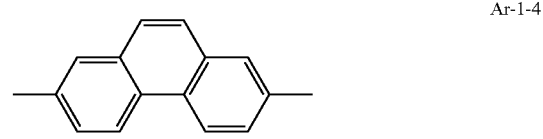
Ar-1-4

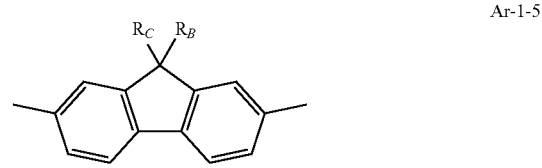
Ar-1-5

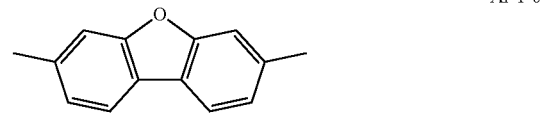
Ar-1-6

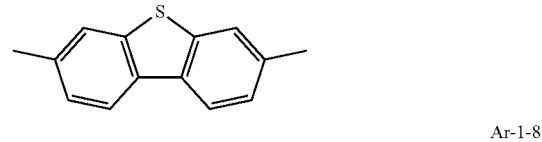
Ar-1-7

Ar-1-8

Ar-1-9

Ar-1-10

Ar-1-11

Ar-1-12

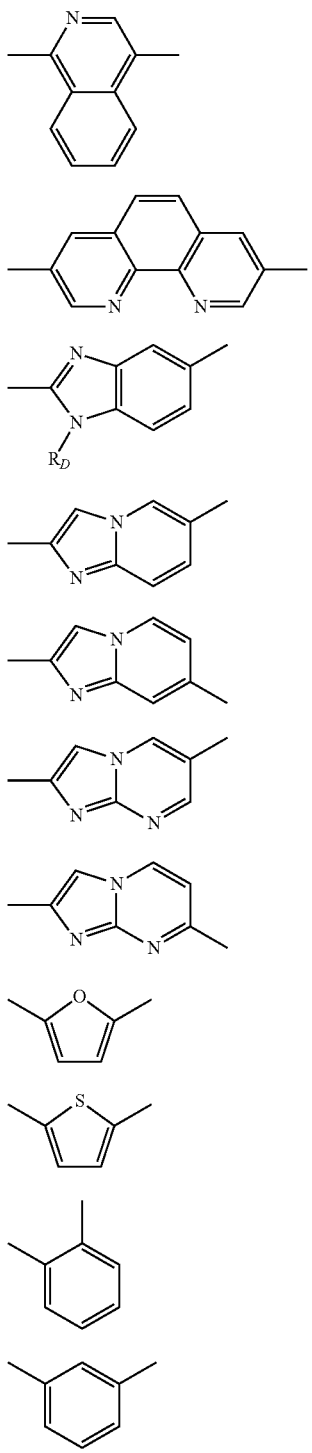

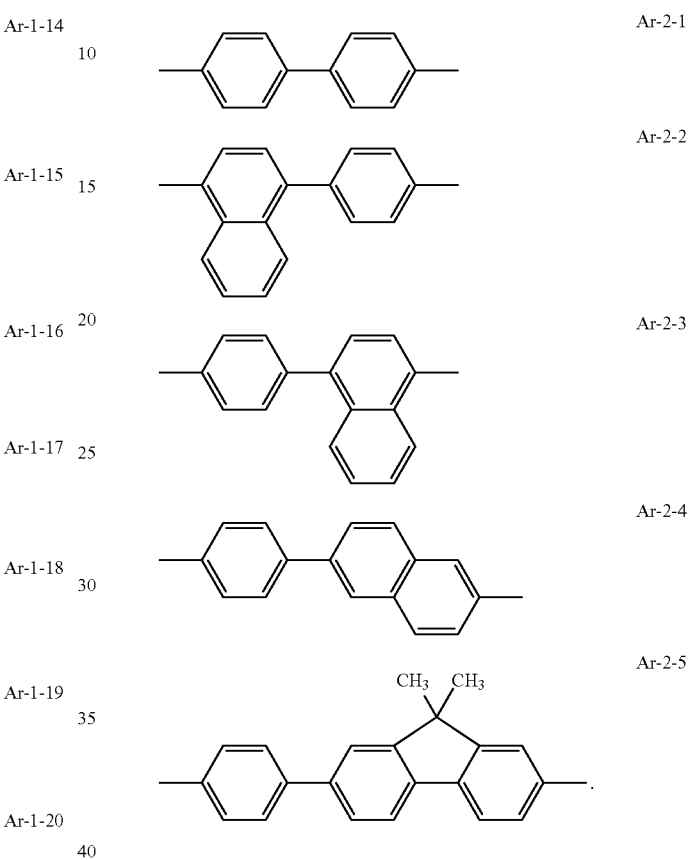

20. The compound according to claim 16, wherein
a moiety represented by —Ar$^{11a}$—Ar$^{12a}$— in the substituent represented by the formula (11b) has a structure selected from the group consisting of structures represented by formulae (Ar-2-1) to (Ar-2-5) below, where: R$_B$ and R$_C$ in the formula (Ar-1-5) represent an unsubstituted methyl group or an unsubstituted phenyl group; and R$_D$ in the formula (Ar-1-15) represents an unsubstituted methyl group or an unsubstituted phenyl group.

19. The compound according to claim 18, wherein
Ar in the formula (11a) represents a structure represented by the formula (Ar-1-1).

21. The compound according to claim 17, wherein
a moiety represented by —Ar$^{13a}$—Ar$^{14a}$—Ar$^{15a}$— in the substituent represented by the formula (11c) has a structure selected from the group consisting of structures represented by formulae (Ar-3-1) to (Ar-3-11) below,

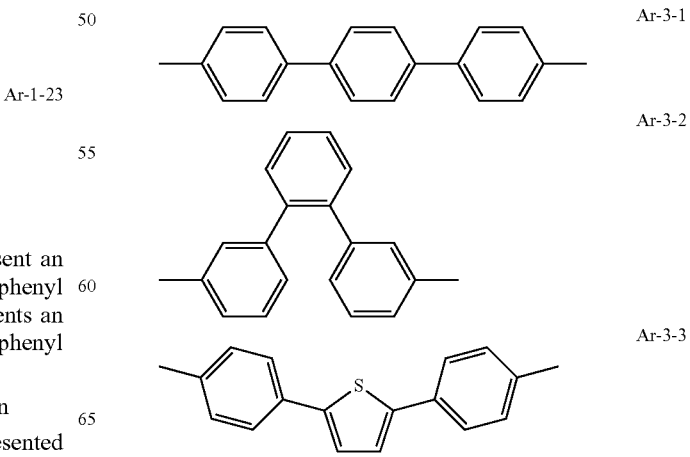

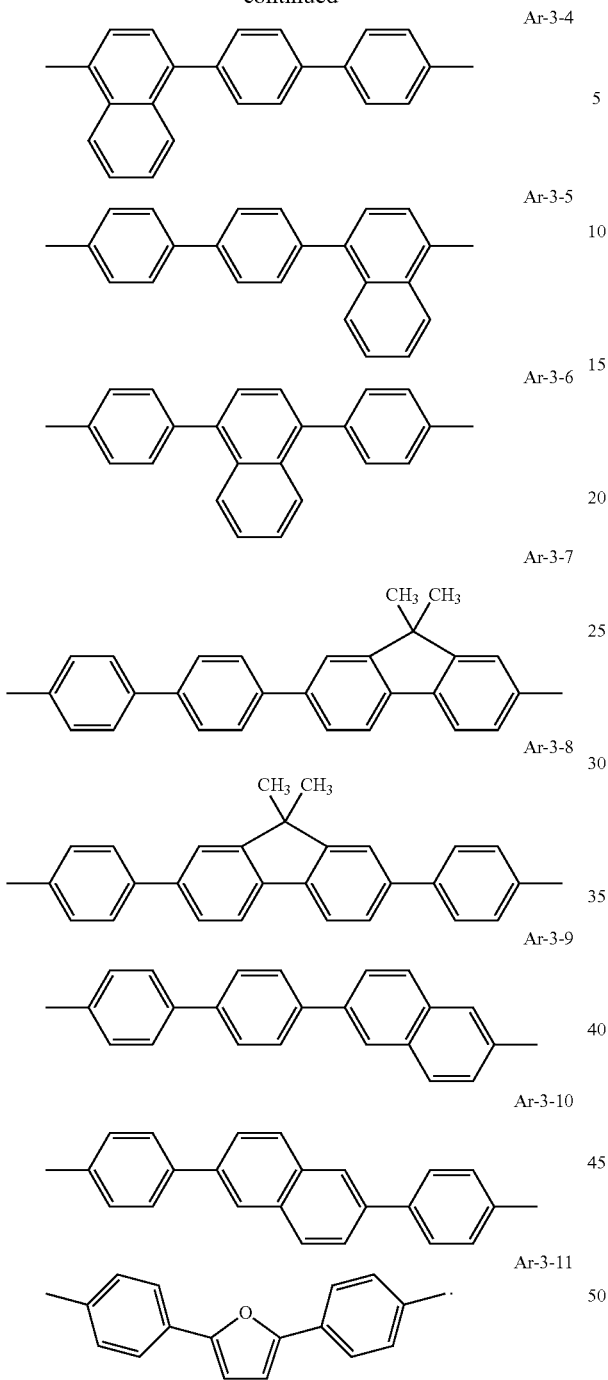

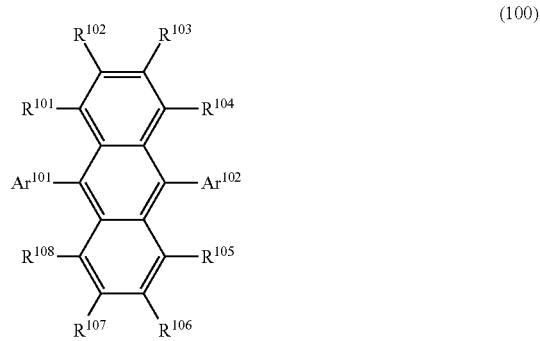

22. An organic electroluminescence device material comprising the compound according to claim 1.

23. An organic electroluminescence device comprising:
a cathode;
an anode; and
at least one organic layer provided between the cathode and the anode, the organic layer comprising the compound according to claim 1.

24. The organic electroluminescence device according to claim 23, wherein
the organic layer comprises an emitting layer, and
the emitting layer comprises the compound.

25. The organic electroluminescence device according to claim 24, wherein
the emitting layer comprises an anthracene derivative represented by a formula (100) below, where: $Ar^{101}$ and $Ar^{102}$ each independently represent a substituted or unsubstituted monocyclic group having 5 to 30 ring atoms, a substituted or unsubstituted fused ring group having 10 to 30 ring atoms, a chain group formed by bonding two groups selected from the group consisting of the monocyclic group and the fused ring group, or a chain group formed by bonding three groups selected from the group consisting of the monocyclic group and the fused ring group; the monocyclic group or groups and the fused ring group or groups in the chain group are mutually the same or different, and the groups in the chain group are optionally bonded to each other to form a ring; $R^{101}$ to $R^{108}$ each independently represent a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, a substituted or unsubstituted arylthio group having 6 to 30 ring carbon atoms, a substituted or unsubstituted monocyclic group having 5 to 30 ring atoms, a substituted or unsubstituted fused ring group having 10 to 30 ring atoms, a chain group formed by bonding two groups selected from the group consisting of the monocyclic group and the fused ring group, or a chain group formed by bonding three groups selected from the group consisting of the monocyclic group and the fused ring group; adjacent ones of $R^{101}$ to $R^{108}$ are optionally bonded to each other to form a ring or not bonded; $R^{101}$ to $R^{108}$ are optionally bonded to a carbon atom of an anthracene ring to form a ring or not bonded; $Ar^{101}$ is optionally bonded to at least any one of adjacent $R^{101}$ and $R^{108}$ to form a ring or not bonded; $Ar^{102}$ is optionally bonded to at least any one of adjacent $R^{104}$ and $R^{105}$ to form a ring or not bonded; and at least one of $Ar^{101}$ and $Ar^{102}$ is optionally bonded to a carbon atom of the anthracene ring to form a ring or not bonded.

26. The organic electroluminescence device according to claim 25, wherein
in the formula (100), $Ar^{101}$ and $Ar^{102}$ each independently represent a substituted or unsubstituted fused ring group having 10 to 30 ring carbon atoms.

27. The organic electroluminescence device according to claim 25, wherein
in the formula (100), one of $Ar^{101}$ and $Ar^{102}$ represents a substituted or unsubstituted monocyclic group having 5 to 30 ring carbon atoms, and the other one thereof represents a substituted or unsubstituted fused ring group having 10 to 30 ring carbon atoms.

28. The organic electroluminescence device according to claim 27, wherein
in the formula (100), $Ar^{102}$ is selected from among a naphthyl group, phenanthryl group, benzoanthryl group, and dibenzofuranyl group, and
$Ar^{101}$ represents an unsubstituted phenyl group, or a phenyl group substituted by at least one of the monocyclic group and the fused ring group.

29. The organic electroluminescence device according to claim 27, wherein
in the formula (100), $Ar^{102}$ represents a substituted or unsubstituted fused ring group having 10 to 30 ring carbon atoms, and $Ar^{101}$ represents an unsubstituted phenyl group.

30. The organic electroluminescence device according to claim 25, wherein
in the formula (100), $Ar^{101}$ and $Ar^{102}$ each independently represent a substituted or unsubstituted monocyclic group having 5 to 30 ring carbon atoms.

31. The organic electroluminescence device according to claim 30, wherein
in the formula (100), $Ar^{101}$ and $Ar^{102}$ each independently represent a substituted or unsubstituted phenyl group.

32. The organic electroluminescence device according to claim 30, wherein
in the formula (100), $Ar^{101}$ represents an unsubstituted phenyl group, and $Ar^{102}$ represents a phenyl group comprising at least one of the monocyclic group and the fused ring group as a substituent.

33. The organic electroluminescence device according to claim 30, wherein
in the formula (100), $Ar^{101}$ and $Ar^{102}$ each independently represent a phenyl group comprising at least one of the monocyclic group and the fused ring group as a substituent.

34. An electronic apparatus comprising the organic electroluminescence device according to claim 23.

35. The compound according to claim 1, wherein
$Ar^2$ in the formula (1) is selected from among a substituted or unsubstituted phenyl group, a substituted or unsubstituted biphenyl group, a substituted or unsubstituted terphenyl group, a substituted or unsubstituted naphthyl group, a substituted or unsubstituted anthryl group, a substituted or unsubstituted phenanthryl group, a substituted or unsubstituted fluorenyl group, a substituted or unsubstituted pyrenyl group, a substituted or unsubstituted chrysenyl group, a substituted or unsubstituted fluoranthenyl group, a substituted or unsubstituted benzo[a]anthryl group, a substituted or unsubstituted benzo[c]phenanthryl group, a substituted or unsubstituted triphenylenyl group, a substituted or unsubstituted benzo[k]fluoranthenyl group, a substituted or unsubstituted benzo[g]chrysenyl group, a substituted or unsubstituted benzo[b]triphenylenyl group, a substituted or unsubstituted picenyl group, and a substituted or unsubstituted perylenyl group.

36. The compound according to claim 1, wherein
$Ar^2$ in the formula (1) is selected from among a substituted or unsubstituted phenyl group, a substituted or unsubstituted biphenyl group, and a substituted or unsubstituted naphthyl group, and
when $Ar^2$ has a substituent, the substituent is an alkyl group.

37. The compound according to claim 1, wherein
$Ar^2$ in the formula (1) represents a substituted or unsubstituted phenyl group, and
when $Ar^2$ has a substituent, the substituent is an alkyl group.

38. The compound according to claim 1, wherein
$Ar^2$ in the formula (1) represents a substituted or unsubstituted aromatic hydrocarbon group having 6 to 20 ring carbon atoms.

39. The compound according to claim 1, wherein
$Ar^2$ in the formula (1) represents a substituted or unsubstituted aromatic hydrocarbon group having 6 to 12 ring carbon atoms.

40. The organic electroluminescence device according to claim 24, wherein
the emitting layer comprises the compound as a dopant material.

41. The organic electroluminescence device according to claim 40, wherein
the compound emits blue light.

42. The organic electroluminescence device according to claim 40, wherein
the compound emits pure-blue light.

* * * * *